US012753397B2

(12) United States Patent
Liang et al.

(10) Patent No.: US 12,753,397 B2
(45) Date of Patent: Oct. 6, 2026

(54) PRIME EDITOR SYSTEM FOR IN VIVO GENOME EDITING

(71) Applicant: UNIVERSITY OF MASSACHUSETTS, Boston, MA (US)

(72) Inventors: Shun-Qing Liang, Shrewsbury, MA (US); Pengpeng Liu, Worcester, MA (US); Wen Xue, Natick, MA (US); Scot Wolfe, Winchester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 914 days.

(21) Appl. No.: 17/909,264

(22) PCT Filed: Feb. 4, 2022

(86) PCT No.: PCT/US2022/015260
§ 371 (c)(1),
(2) Date: Sep. 2, 2022

(87) PCT Pub. No.: WO2022/170058
PCT Pub. Date: Aug. 11, 2022

(65) Prior Publication Data

US 2023/0374476 A1 Nov. 23, 2023

Related U.S. Application Data

(60) Provisional application No. 63/146,198, filed on Feb. 5, 2021.

(51) Int. Cl.
*C12N 9/22* (2006.01)
*A61P 1/16* (2006.01)
*C12N 9/12* (2006.01)

(52) U.S. Cl.
CPC .................. *C12N 9/22* (2013.01); *A61P 1/16* (2018.01); *C12N 9/1276* (2013.01); *C07K 2319/80* (2013.01); *C12N 2310/20* (2017.05)

(58) Field of Classification Search
CPC .... C12N 9/22; C12N 9/1276; C12N 2310/20; A61P 1/16; C07K 2319/80
See application file for complete search history.

(56) References Cited

U.S. PATENT DOCUMENTS

2015/0211023 A1 7/2015 Shiboleth et al.
2019/0010490 A1 1/2019 Cowan et al.

FOREIGN PATENT DOCUMENTS

WO WO/2020/127831 6/2020
WO WO/2020/191171 9/2020
WO WO-2020191171 A1 * 9/2020

OTHER PUBLICATIONS

Aida, T. et al. (2020) "Prime editing primarily induces undesired outcomes in mice," *bioRxiv*, 2020.2008.2006.239723.

Anzalone, A. V. et al. (2019) "Search-and-replace genome editing without double-strand breaks or donor DNA," *Nature* 576(7785), 149-157.

Blankenberg, D. et al. (2010) "Manipulation of FASTQ data with Galaxy," *Bioinformatics* 26(14), 1783-1785.

Bolukbasi, M. F. et al. (2018) "Orthogonal Cas9-Cas9 chimeras provide a versatile platform for genome editing," *Nature Communications* 9(1), 4856.

Carlson, J. A. et al. (1989) "Accumulation of PiZ alpha 1-antitrypsin causes liver damage in transgenic mice," *Journal of Clinical Investigation* 83(4), 1183-1190.

Carrington, M. et al. (1997) "Novel Alleles of the Chemokine-Receptor Gene CCR5," *American Journal of Human Genetics* 61(6), 1261-1267.

Certo, M. T. et al. (2011) "Tracking genome engineering outcome at individual DNA breakpoints," *Nature Methods* 8, 671-676.

Cong, L. et al. (2013) "Multiplex Genome Engineering Using CRISPR/Cas Systems," *Science* (*New York, N.Y.*) 339(6121), 819-823.

Dean, M. et al. (1996) "Genetic Restriction of HIV-1 Infection and Progression to AIDS by a Deletion Allele of the CKR5 Structural Gene," *Science* 273(5283), 1856-1862.

Doudna, J. A. et al. (2014) "Genome editing. The new frontier of genome engineering with CRISPR-Cas9," *Science* 346(6213), Article No. 1258096.

Esvelt, K. M. et al. (2013) "Orthogonal Cas9 Proteins for RNA-Guided Gene Regulation and Editing," *Nature Methods* 10(11), 1116-1121.

Gaudelli, N. M. et al. (2017) "Programmable base editing of A•T to G•C in genomic DNA without DNA cleavage," *Nature* 551(7681), 464-471.

Geurts, M. H. et al. (2021) "Evaluating CRISPR-based prime editing for cancer modeling and CFTR repair in organoids," *Life Science Alliance* 4(10), e202000940.

Giannoukos, G. et al. (2018) "UDiTaS™, a genome editing detection method for indels and genome rearrangements," *BMC Genomics* 19(1), 212.

Iyer, S. et al. (2019) "Efficient Homology-directed Repair With Circular ssDNA Donors," *bioRxiv*, 864199.

Jinek, M. et al. (2012) "A programmable dual-RNA-guided DNA endonuclease in adaptive bacterial immunity," *Science* 337(6096), 816-821.

(Continued)

*Primary Examiner* — David Steadman
*Assistant Examiner* — Scott E. Mulder
(74) *Attorney, Agent, or Firm* — Medlen & Carroll, LLP

(57) ABSTRACT

The present applications discloses an NLS-optimized SpCas9-based prime editor that improves genome editing efficiency exemplified by endogenous loci in cultured cell lines. Using this genome modification system, tumor formation can be initiated through somatic cell editing in the adult mouse. Furthermore, a dual adeno-associated vims (AAVs) is utilized for the delivery of a split-intein prime editor for correction of in vivo pathogenic mutations.

8 Claims, 27 Drawing Sheets

Specification includes a Sequence Listing.

(56) References Cited

OTHER PUBLICATIONS

Kleinstiver, B. P. et al. (2015) "Broadening the targeting range of *Staphylococcus aureus* CRISPR-Cas9 by modifying PAM recognition," *Nature Biotechnology* 33 (12), 1293-1298.
Koblan, L. W. et al. (2018) "Improving cytidine and adenine base editors by expression optimization and ancestral reconstruction," *Nature Biotechnology* 36(9), 843-846.
Levy, J. M. et al. (2020) "Cytosine and adenine base editing of the brain, liver, retina, heart and skeletal muscle of mice via adeno-associated viruses," *Nature Biomedical Engineering* 4(1), 97-110.
Lin, Q. et al. (2020) "Prime genome editing in rice and wheat," *Nature Biotechnology* 38(5), 582-585.
Liu, F. et al. (1999) "Hydrodynamics-based transfection in animals by systemic administration of plasmid DNA," *Gene Therapy* 6, 1258-1266.
Liu, P. et al. (2017) "A functional mammalian target of rapamycin complex 1 signaling is indispensable for c-Myc-driven hepatocarcinogenesis," *Hepatology* 66(1), 167-181.
Liu, R. et al. (1996) "Homozygous Defect in HIV-1 Coreceptor Accounts for Resistance of Some Multiply-Exposed Individuals to HIV-1 Infection," *Cell* 86(3), 367-377.
Liu, Y. et al. (2020) "Efficient generation of mouse models with the prime editing system," *Cell Discovery* 6(1), 27.
Loring, H. S. et al. (2015) "Current status of gene therapy for α-1 antitrypsin deficiency," *Expert Opinion on Biological Therapy* 15(3), 329-336.
Maddalo, D. et al. (2014) "In vivo engineering of oncogenic chromosomal rearrangements with the CRISPR/Cas9 system," *Nature* 516(7531), 423-427.
Makkerh, J. P. S. et al. (1996) "Comparative mutagenesis of nuclear localization signals reveals the importance of neutral and acidic amino acids," *Current Biology* 6(8), 1025-1027.
Marquardt, J. U. et al. (2015) "Functional and genetic deconstruction of the cellular origin in liver cancer," *Nature Reviews. Cancer* 15(11), 653-667.
Mir, A. et al. (2018) "Heavily and fully modified RNAs guide efficient SpyCas9-mediated genome editing," *Nature Communications* 9(1), 2641.
Miura, K. (2020) "Measurements of Intensity Dynamics at the Periphery of the Nucleus," in *Bioimage Data Analysis Workflows* (Miura, K., et al., Eds.), pp 9-32, Springer International Publishing, Cham.
Panier, S. et al. (2014) "Double-strand break repair: 53BP1 comes into focus," *Nature Reviews Molecular Cell Biology* 15(1), 7-18.
Pickar-Oliver, A. et al. (2019) "The next generation of CRISPR-Cas technologies and applications," *Nature Reviews Molecular Cell Biology* 20(8), 490-507.
Porteus, M. H. (2019) "A New Class of Medicines through DNA Editing," *New England Journal of Medicine* 380(10), 947-959.
Ran, F. A. et al. (2015) "In vivo genome editing using *Staphylococcus aureus* Cas9," *Nature* 520(7546), 186-191.
Ray, M. et al. (2015) "Quantitative Tracking of Protein Trafficking to the Nucleus Using Cytosolic Protein Delivery by Nanoparticle-Stabilized Nanocapsules," *Bioconjugate Chemistry* 26(6), 1004-1007.
Rees, H. A. et al. (2018) "Base editing: precision chemistry on the genome and transcriptome of living cells," *Nature Reviews Genetics* 19(12), 770-788.
Schene, I. F. et al. (2020) "Prime editing for functional repair in patient-derived disease models," *Nature Communications* 11(1), 5352.
Song, C.-Q. et al. (2020) "Adenine base editing in an adult mouse model of tyrosinaemia," *Nature Biomedical Engineering* 4(1), 125-130.
Suzuki, K. et al. (2016) "In vivo genome editing via CRISPR/Cas9 mediated homology-independent targeted integration," *Nature* 540(7631), 144-149.
Walton, R. T. et al. (2020) "Unconstrained genome targeting with near-PAMless engineered CRISPR-Cas9 variants," *Science* 368(6488), 290-296.
Wright, A. V. et al. (2015) "Rational design of a split-Cas9 enzyme complex" *Proceedings of the National Academy of Sciences of the United States of America* 112(10), 2984-2989.
Wu, Y. et al. (2019) "Highly efficient therapeutic gene editing of human hematopoietic stem cells," *Nature Medicine* 25(5), 776-783.
Xue, W. et al. (2014) "CRISPR-mediated direct mutation of cancer genes in the mouse liver," *Nature* 514, 380-384.
Yao, X. et al. (2017) "CRISPR/Cas9—Mediated Precise Targeted Integration In Vivo Using a Double Cut Donor with Short Homology Arms," *eBioMedicine* 20, 19-26.
Yin, H. et al. (2016) "Therapeutic genome editing by combined viral and non-viral delivery of CRISPR system components in vivo," *Nature Biotechnology* 34, 328-333.
Zafra, M. P. et al. (2018) "Optimized base editors enable efficient editing in cells, organoids and mice," *Nature Biotechnology* 36(9), 888-893.
Zettler, J. et al. (2009) "The naturally split Npu DnaE intein exhibits an extraordinarily high rate in the protein trans-splicing reaction," *FEBS Letters* 583(5), 909-914.
Zhang, J. et al. (2013) "PEAR: a fast and accurate Illumina Paired-End reAd mergeR," *Bioinformatics* 30(5), 614-620.
Zucman-Rossi, J. et al. (2015) "Genetic Landscape and Biomarkers of Hepatocellular Carcinoma," *Gastroenterology* 149(5), 1226-1239. e1224.
PCT International Search Report of International Application No. PCT/US2022/015260 dated Jul. 1, 2022.

* cited by examiner

FIG. 1C
FIG. 1D
c
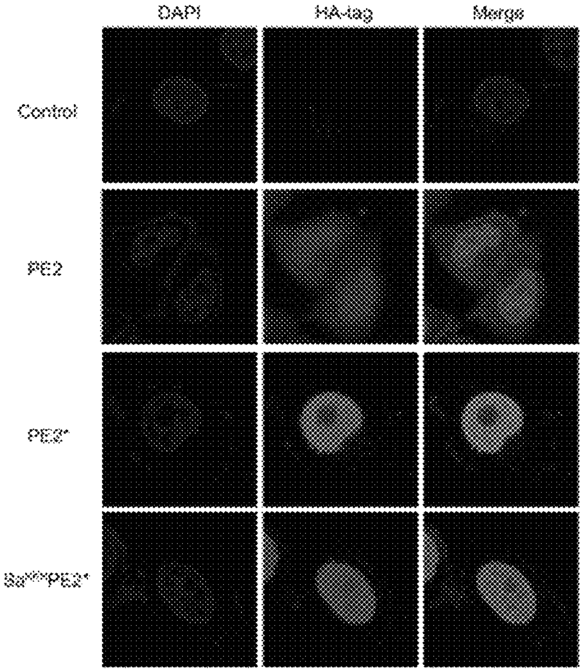
d
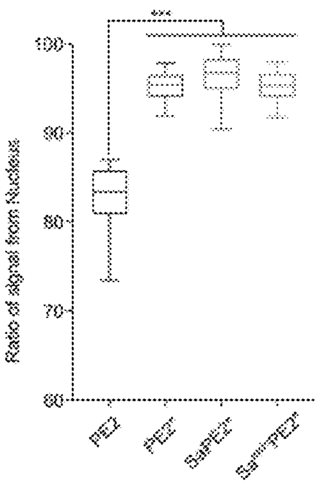

SEQ ID NO: 86

SEQ ID NO: 87

SEQ ID NO: 88

SEQ ID NO: 89

SEQ ID NO: 90

SEQ ID NO: 91

Fig. 4A
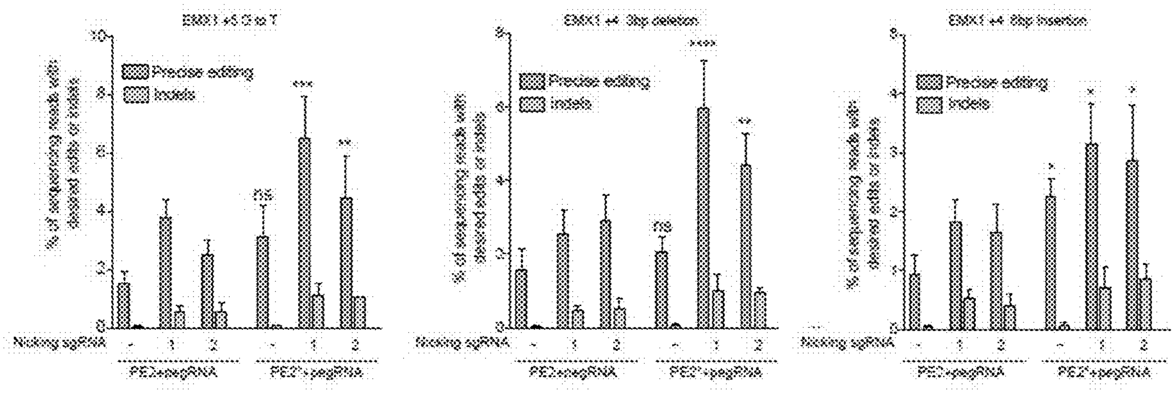
Fig. 4B
Fig. 4C
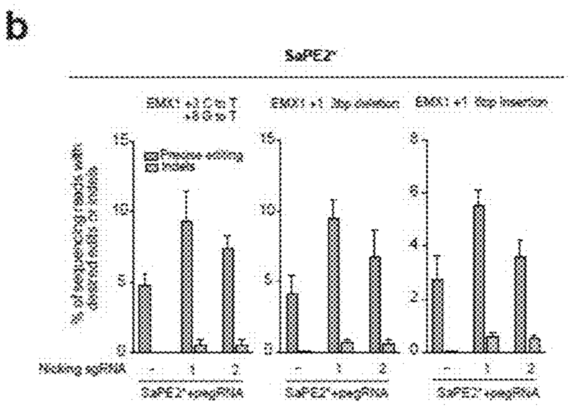
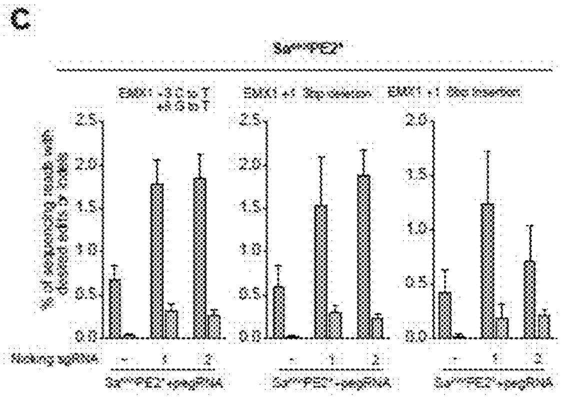

CCR5 Delta32 Deletion

SEQ ID NO: 111

SEQ ID NO: 112

SEQ ID NO: 124

SEQ ID NO: 125

SEQ ID NO: 126

SEQ ID NO: 127

SEQ ID NO: 128

K342E correction (via dual AAV)

PRIME EDITOR SYSTEM FOR IN VIVO GENOME EDITING

CROSS REFERENCE TO RELATED APPLICATIONS

This application is a Continuation that claims priority to PCT/US22/15260 filed Feb. 4, 2022, which claims priority of U.S. Provisional Application Ser. No. 63/146,198 filed Feb. 5, 2021, now expired, the contents of which are incorporated herein in their entirety.

STATEMENT OF GOVERNMENT INTEREST

This invention was made with government support under HL137167, HL131471, HL147367, GM115911 and TR002668 awarded by the National Institutes Of Health. The government has certain rights in the invention.

REFERENCE TO AN ELECTRONIC SEQUENCE LISTING

The contents of the electronic sequence listing ("2013_ST25.txt"; Size: 83,80 bytes; Date of Creation: Sep. 2, 2022) and submitted via EFS Sep. 2, 2022, is herein incorporated by reference in its entirety.

FIELD OF THE INVENTIONS

This invention is related to the field of genetic engineering. In particular, compositions and methods that specifically and accurately repair genetic mutations that are responsible for the expression of a genetic disease. For example, a Cas9 complex modified as a prime editor and a plurality of nuclear localization signals. The therapeutic use of such modified Cas9 complexes repair genetic mutations with a higher efficiency, without repair-related indels and reduce the symptomology of a genetic disease.

BACKGROUND OF THE INVENTION

Disease-associated genetic variations, including deletions, insertions and base substitutions, require precise gene correction strategies that are both robust and flexible. Porteus, M. H., "A New Class of Medicines through DNA Editing" *N Engl J Med* 380:947-740 959 (2019). Homology-direct repair (HDR) enables precise genome editing through an exogenous donor DNA. However, HDR is inefficient in most therapeutically relevant cell types, especially in post-mitotic cells. Panier et al., "Double-strand break repair: 53BP1 comes into focus" *Nat Rev Mol Cell Biol* 15, 7-18 (2014); Suzuki et al., "In vivo genome editing via CRISPR/Cas9 mediated homology independent targeted integration" *Nature* 540:144-149 (2016); and Pickar-Oliver et al., "The next generation of CRISPR-Cas technologies and applications" *Nat Rev Mol Cell Biol* 20:490-507 (2019).

Base editing enables efficient nucleotide transitions without inducing double-strand breaks (DSBs). Rees et al., "Base editing: precision chemistry on the genome and transcriptome of living cells" *Nature Reviews Genetics* 19:770-788 (2018). However, targeted nucleotide transversions, deletions and insertions are not easily facilitated by well-established editing systems. In addition, depending on the local sequence context, base editing systems can also convert "bystander" nucleotides within the same editing window, which may be mutagenic, leading to the creation of unproductive or counter-productive alleles.

Prime editing systems potentially provide a powerful approach for the template-directed incorporation of a variety of types of alterations (nucleotide changes, insertions, deletions) into genomic DNA sequence without relying on homology directed repair (HDR). In principle, this provides a strategy for the correction of a variety of different disorders, since prime editing should not be dependent on the cell cycle for efficacy as is HDR "Panier, S. & Boulton, S. J. Double-strand break repair: 53BP1 comes into focus." *Nat Rev Mol Cell Biol* 15, 7-18 (2014). Moreover, unlike HDR and MMEJ, approaches for precise sequence insertions, prime editing does not require co-delivery of donor DNA. Yao et al., "CRISPR/Cas9-Mediated Precise Targeted Integration In Vivo Using a Double Cut Donor with Short Homology Arms" *EBioMedicine* 20:19-26 (2017). However, the length of the sequence that can be inserted is limited by the length of the encoded pegRNA. While there are many potential advantages to prime editing, the development of prime editing systems is in its initial stages, and many questions with regard to the utility of this system for genome editing remain to be addressed.

What is needed in the art are in vivo prime editors for template-based modification of genomic sequence with implications for improving the utility of disease model systems and for the eventual translation of this tool to the correction of pathogenic disorders.

SUMMARY OF THE INVENTION

This invention is related to the field of genetic engineering. In particular, compositions and methods that specifically and accurately repair genetic mutations that are responsible for the expression of a genetic disease. For example, a Cas9 complex modified as a prime editor and a plurality of nuclear localization signals. The therapeutic use of such modified Cas9 complexes repair genetic mutations with a higher efficiency, without repair-related indels and reduce the symptomology of a genetic disease.

In one embodiment, the present invention contemplates a method, comprising: a) providing: i) a patient having at least one causative mutation in an allele linked a genetic disease; ii) a fusion protein complex comprising a catalytically impaired Cas9 nickase, an engineered reverse transcriptase (RT) and a prime editing guide RNA molecule (pegRNA) comprising a primer binding site (PBS); b) administering said fusion protein to said patient; and c) editing said at least one causative mutation resulting in a conversion to a wild type allele. In one embodiment, said wild type allele is without editing-related indels. In one embodiment, the fusion protein complex comprises a split-intein prime editor protein. In one embodiment, the administering comprises the split-intein prime editor protein packaged in a dual adenovirus platform. In one embodiment, the genetic disease is alpha-1 antitrypsin deficiency (AATD). In one embodiment, the conversion comprises a G•C-to-A•T base transition in a serpina1 gene. In one embodiment, the conversion of the serpina1 gene occurs with a base conversion of 1.6-3.4 fold greater efficiency than a conventional prime editor. In one embodiment, the pathogenic disease is acquired immunodeficiency syndrome (AIDS) caused by Human immunodeficiency virus (HIV). In one embodiment, the creation of HIV resistant cells comprises a ccr5 gene deletion that is a naturally occurring variant in the human population Carrington, M. et al. "Novel Alleles of the Chemokine-Receptor Gene CCR5" *Am J Hum Genetics* 61, 1261-1267 (1997). In one embodiment, the ccr5 gene deletion comprises 32 base pairs. In one embodiment, the creation of the ccr5 gene deletion occurs with a 1.4 fold greater efficiency than a conventional prime editor. In one embodiment, said conversion occurs with a base conversion or sequence insertion that has 1.5-fold higher efficiency than a conventional prime editor. In one embodiment, said conversion occurs with a sequence deletion or sequence insertion that has a 2-fold higher efficiency than a conventional prime editor.

In one embodiment, the present invention contemplates a method, comprising: a) providing: i) a non-human mammal comprising a wild type genome; ii) a fusion protein complex comprising a catalytically impaired Cas9 nickase, an engineered reverse transcriptase (RT) and a prime editing guide RNA molecule (pegRNA) comprising a primer binding site (PBS); b) administering said fusion protein to said non-human mammal; and c) editing said wild type genome resulting in a conversion to a mutated genome. In one embodiment, the conversion comprises an insertion of a mutated allele. In one embodiment, the inserted mutated allele is oncogenic. In one embodiment, said conversion occurs with a base conversion of twelve-fold higher efficiency than homology-direct repair. In one embodiment, said conversion occurs with a deletion, insertion or point mutation of two-fold increase in efficiency than a conventional prime editor. In one embodiment, the mutated allele is within a ctnnb1 gene. In one embodiment, the ctnnb1 gene mutated allele is a S45 codon deletion. In one embodiment, the oncogenic mutated allele is 2-fold more efficient in tumor formation than a conventional prime editor. In one embodiment, the fusion protein comprises a split-intein prime editor protein. In one embodiment, the administering comprises the split-intein prime editor protein packaged in a dual adenovirus platform.

In one embodiment, the present invention contemplates a fusion protein comprising a catalytically impaired Cas9 nickase, an engineered reverse transcriptase (RT) a prime editing guide RNA molecule (pegRNA) comprising a primer binding site (PBS). In one embodiment, the catalytically impaired Cas9 nickase is nSpCas9$^{840A}$, where the "n" prefix denotes the nickase. In one embodiment, the catalytically impaired Cas9 nickase is nSaCas9$^{840A}$. In one embodiment, the catalytically impaired Cas9 nickase is nSa$^{KKH}$Cas9N$^{580A}$. In one embodiment, the fusion protein comprises a plurality of nuclear localization signal (NLS) sequences. In one embodiment, the fusion protein comprises at least three NLS sequences. In one embodiment, the fusion protein comprises four NLS sequences. In one embodiment, the plurality of NLS sequences comprise at least two BP-SV40 NLS sequences. In one embodiment, the plurality of NLS sequences comprise a vBP-SV40 NLS sequence. In one embodiment, the vBP-SV40 NLS sequence is attached to an N-terminus of the fusion protein. In one embodiment, the plurality of NLS sequences comprise a C-myc NLS sequence. In one embodiment, the C-myc NLS sequence is attached to the N-terminus of the fusion protein. In one embodiment, the reverse transcriptase is a Moloney Murine Leukemia Virus (M-MLV) reverse transcriptase. In one embodiment, the engineered reverse transcriptase comprises a plurality of mutations.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" or "approximately" as used herein, in the context of any of any assay measurements refers to +/−5% of a given measurement.

The term, "nuclear localization signal sequence" or "NLS", as used here refers to an amino acid sequence that 'tags' a protein for import into the cell nucleus by nuclear transport.

Typically, this signal includes one or more short sequences of positively charged lysines or arginines exposed on the protein surface. For example, an NLS includes but is not limited to an SV40 NLS (PKKKRKV) (SEQ ID NO: 4), a bipartite SV40 NLS (BP-SV40 NLS; KRTADGSEF-ESPKKKRKV) (SEQ ID NO: 5), a variant bipartite SV40 NLS (vBP-SV40 NLS; KRTADSSHSTPPKTKRKV) (SEQ ID NO: 6), a Nucleoplasmin NLS (KRPAATKK-AGQAKKKKLD) (SEQ ID NO: 7) or a C-myc NLS (PAAKRVKLD) (SEQ ID NO: 8).

The term "causative mutation", as used herein refers to any variation of a wild type genomic sequence which has been clinically associated with the expression of symptoms of a genetic disease.

The term "allele", as used herein refers to one of two, or more, versions of the same gene at the same place on a chromosome. It can also refer to different sequence variations for a several-hundred base-pair, or more, region of a genome that codes for a protein. Paired alleles can differ by only a single base pair.

The term "genetic disease", as used herein refers to a medical condition or disorder that has been clinically linked to an aberration in the structure or function of a particular gene. For example, the particular gene aberration may comprise a causative mutation including, but not limited to, a single polynucleotide polymorphism, a nonsense codon, an insertion or a deletion.

The term "catalytically impaired Cas9 nickase" or "nCas9", as used herein refers to a mutated Cas9 which renders the nuclease able to cleave only one strand of deoxyribonucleic acid backbone. Depending on the position of the mutation within the Cas9 protein sequence either the target or non-target strand is cleaved. In the case of a prime editor the non-target strand is selectively cleaved.

The term "engineered reverse transcriptase" as used herein, refers to a protein that converts RNA into DNA and contains specific mutations that effect its activity efficiency. One example, of a reverse transcriptase is a Moloney murine leukemia virus reverse transcriptase (M-MLV RT).

The term "reverse transcriptase template" as used herein refers to a ribonucleic acid sequence that is utilized as a substrate for a reverse transcriptase protein that is part of the fusion protein complex as contemplated herein. Such templates provide the necessary information to edit a DNA sequence to support conversions including, but not limited to, base conversions, sequence insertions or sequence deletions.

The term "primer binding site" as used herein, refers to a specific nucleic acid sequence within the pegRNA that is complementary to the 3' end of the nicked DNA strand. This allows annealing of the free 3' end of the genomic DNA for extension by the reverse transcriptase based on the template sequence encoded in the pegRNA.

The term, "prime editing guide RNA molecule" or "pegRNA molecule" as used herein, refers to a Cas9 guide RNA molecule that encodes the crRNA-tracrRNA fused to a primer binding site (PBS) and a reverse transcriptase template nucleic acid sequence. The primer binding site hybridizes to a desired genomic sequence released by the binding and cleavage of the Cas9 nickase. The 3' end of the genomic sequence is extended by the reverse transcriptase based on the reverse transcriptase template sequence.

The term "editing" as used herein, refers to a genetic manipulation of a DNA sequence. Such a manipulation includes, but is not limited to, a base conversion, a sequence insertion and/or a sequence deletion.

The term "prime editing" as used herein, is a genome editing technology by which the genome of living organisms may be modified. Prime editing manipulates the genetic information of a targeted DNA site to essentially "rewrite" the coded sequences.

The term "prime editor" or "PE" as used herein, is a fusion protein comprising a catalytically impaired Cas9 endonuclease that can nick DNA and is fused to an engineered reverse transcriptase enzyme and attached to a prime editing guide RNA (pegRNA). The pegRNA is capable of programming the nCas9 to recognize a target site with the encoded crRNA-tracrRNA (as does a conventional single guide RNA). The resulting nicked genomic DNA can be extended by the reverse transcriptase based on the pegRNA template sequence to contain a new sequence. Once one strand is recoded, cellular DNA repair pathways can cause conversion of the local DNA sequence to match the new sequence. Such manipulation includes, but is not limited to, insertions, deletions, and base-to-base conversions without the need for double strand breaks (DSBs) or donor DNA templates. For example, such prime editing may be performed by a Cas9 CRISPR platform programmed with a pegRNA, such as a catalytically impaired Cas9 nickase platform with an appropriate reverse transcriptase.

The term "conversion" as used herein, refers to any manipulation of a nucleic acid sequence that converts a mutated sequence into a wild type sequence, or a wild type sequence into a mutated sequence. For example, a converted sequence includes, but is not limited to, a base pair conversion, a nucleic acid sequence insertion or a nucleic acid sequence deletion.

The term "editing-related indels" as used herein, refers to the generation of off-target and/or unintended nucleotide sequence insertions created by a prime editor.

The term "split-intein prime editor protein" refers to a prime editor protein that has been split into amino-terminal (PE2-N) and carboxy-terminal (PE2-C) segments, which are then fused into a full length PE by a trans-splicing intein. This configuration imparts flexibility to the prime editor thereby facilitating a packaging into an adeno-associated virus (AAV).

The term "oncogenic" as used herein, refers to any compound or genetic condition that results in the development of cancer.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by 30 or so base pairs known as "spacer DNA". The spacers are short segments of DNA from a virus and may serve as a 'memory' of past exposures to facilitate an adaptive defense against future invasions (PMID 25430774). These sequences are transcribed and processed in CRISPR RNAs (crRNA).

As used herein, the term "Cas" or "CRISPR-associated (cas)" refers to genes often associated with CRISPR repeat-spacer arrays (PMID 25430774).

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek combined tracrRNA and spacer RNA (or crRNA) into a "single-guide RNA" (sgRNA) molecule that, mixed with Cas9, could find and cleave DNA targets through Watson-Crick pairing between the guide sequence within the sgRNA and the target DNA sequence (PMID 22745249).

The term "protospacer adjacent motif" (or PAM) as used herein, refers to a DNA sequence that may be required for a Cas9/sgRNA to form an R-loop to interrogate a specific DNA sequence through Watson-Crick pairing of its guide RNA with the genome. The PAM specificity may be a function of the DNA-binding specificity of the Cas9 protein (e.g., a "protospacer adjacent motif recognition domain" at the C-terminus of Cas9).

As used herein, the term "sgRNA" refers to single guide RNA used in conjunction with CRISPR associated systems (Cas). sgRNAs are a fusion of crRNA and tracrRNA and contain nucleotides of sequence complementary to the desired target site (Jinek, et al. 2012 (PMID 22745249)). Watson-Crick pairing of the sgRNA with the target site permits R-loop formation, which in conjunction with a functional PAM permits DNA cleavage or in the case of nuclease-deficient Cas9 allows binds to the DNA at that locus.

As used herein, the term "orthogonal" refers targets that are non-overlapping, uncorrelated, or independent. For example, if two orthogonal Cas9 isoforms were utilized, they would employ orthogonal sgRNAs that only program one of the Cas9 isoforms for DNA recognition and cleavage (Esvelt, et al. 2013 (PMID 24076762)). For example, this would allow one Cas9 isoform (e.g. *S. pyogenes* Cas9 or spCas9) to function as a nuclease programmed by a sgRNA that may be specific to it, and another Cas9 isoform (e.g. *N. meningitidis* Cas9 or nmCas9) to operate as a nuclease dead Cas9 that provides DNA targeting to a binding site through its PAM specificity and orthogonal sgRNA. Other Cas9s include *S. aureus* Cas9 or SaCas9 and *A. naeslundii* Cas9 or AnCas9.

The term "base pairs" as used herein, refer to specific nucleobases (also termed nitrogenous bases), that are the building blocks of nucleotide sequences that form a primary structure of both DNA and RNA. Double stranded DNA may be characterized by specific hydrogen bonding patterns, base pairs may include, but are not limited to, guanine-cytosine and adenine-thymine) base pairs.

The term "specific genomic target" as used herein, refers to any pre-determined nucleotide sequence capable of binding to a Cas9 protein contemplated herein. The target may include, but may be not limited to, a nucleotide sequence complementary to a programmable DNA binding domain or an orthogonal Cas9 protein programmed with its own guide RNA, a nucleotide sequence complementary to a single guide RNA, a protospacer adjacent motif recognition sequence, an on-target binding sequence and an off-target binding sequence.

The term "on-target binding sequence" as used herein, refers to a subsequence of a specific genomic target that may be completely complementary to a programmable DNA binding domain and/or a single guide RNA sequence.

The term "off-target binding sequence" as used herein, refers to a subsequence of a specific genomic target that may be partially complementary to a programmable DNA binding domain and/or a single guide RNA sequence.

The term "nickase" as used herein, refers to a nuclease that cleaves only a single DNA strand, either due to its natural function or because it has been engineered to cleave only a single DNA strand. Cas9 nickase variants that have either the RuvC or the HNH domain mutated provide control over which DNA strand is cleaved and which remains intact (Jinek, et al. 2012 (PMID 22745249) and Cong, et al. 2013 (PMID 23287718)).

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}$ $ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "associated with" as used herein, refers to an art-accepted causal relationship between a genetic mutation and a medical condition or disease. For example, it is art-accepted that a patient having an HTT gene comprising a tandem CAG repeat expansion mutation has, or is a risk for, Huntington's disease.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

The term “portion” when used in reference to a nucleotide sequence refers to fragments of that nucleotide sequence. The fragments may range in size from 5 nucleotide residues to the entire nucleotide sequence minus one nucleic acid residue. When used in reference to an amino acid sequence refers to fragments of that amino acid sequence. The fragment may range in size from 2 amino acid residues to the entire amino acid sequence minus one amino acid residue.

A “variant” of a protein is defined as an amino acid sequence which differs by one or more amino acids from a polypeptide sequence or any homolog of the polypeptide sequence. The variant may have “conservative” changes, wherein a substituted amino acid has similar structural or chemical properties, e.g., replacement of leucine with isoleucine. More rarely, a variant may have “nonconservative” changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A “variant” of a nucleotide is defined as a novel nucleotide sequence which differs from a reference oligonucleotide by having deletions, insertions and substitutions. These may be detected using a variety of methods (e.g., sequencing, hybridization assays etc.).

A “deletion” is defined as a change in either nucleotide or amino acid sequence in which one or more nucleotides or amino acid residues, respectively, are absent.

An “insertion” or “addition” is that change in a nucleotide or amino acid sequence which has resulted in the addition of one or more nucleotides or amino acid residues, respectively, as compared to, for example, the naturally occurring amino acid sequence.

A “substitution” results from the replacement of one or more nucleotides or amino acids by different nucleotides or amino acids, respectively.

As used herein, the terms “complementary” or “complementarity” are used in reference to “polynucleotides” and “oligonucleotides” (which are interchangeable terms that refer to a sequence of nucleotides) related by the base-pairing rules. For example, the sequence “C-A-G-T,” is complementary to the sequence “G-T-C-A.” Complementarity can be “partial” or “total.” “Partial” complementarity is where one or more nucleic acid bases is not matched according to the base pairing rules. “Total” or “complete” complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms “homology” and “homologous” as used herein in reference to nucleotide sequences refer to a degree of complementarity with other nucleotide sequences. There may be partial homology or complete homology (i.e., identity). A nucleotide sequence which is partially complementary, i.e., “substantially homologous,” to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms “homology” and “homologous” as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are “substantially homologous” may have at least 50% identity, preferably at least 75% identity, more preferably at least 85% identity, most preferably at least 95%, or 100% identity.

An oligonucleotide sequence which is a “homolog” is defined herein as an oligonucleotide sequence which exhibits greater than or equal to 50% identity to a sequence, when sequences having a length of 100 bp or larger are compared.

As used herein, the term “hybridization” is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term “hybridization complex” refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term “primer” refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. Efficient expression of recombinant DNA sequences in eukaryotic cells involves expression of signals directing the efficient termination and polyadenylation of the resulting transcript. Transcription termination signals are generally found downstream of the polyadenylation signal and are a few hundred nucleotides in length.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "binding site" as used herein, refers to any molecular arrangement having a specific tertiary and/or quaternary structure that undergoes a physical attachment or close association with a binding component. For example, the molecular arrangement may comprise a sequence of amino acids. Alternatively, the molecular arrangement may comprise a sequence a nucleic acids. Furthermore, the molecular arrangement may comprise a lipid bilayer or other biological material.

BRIEF DESCRIPTION OF THE FIGURES

FIGS. 1A-D presents a comparison of four prime editor variants; i) PE with no NLS sequences; ii) PE with a vBPSV40-NLS; iii) 2×NLS PE (PE2); and iv) PE2*

FIG. 1A: Representative immunofluorescence images subsequent to prime editor transfection into U2OS cells immunostained with a HA tag antibody to visualize subcellular localization. DNA was stained with DAPI. Scale bar, 686 100 μm.

FIG. 1B: The nuclear/cytoplasm ratio of different prime editors as determined by confocal microscopy.

FIGS. C & D: Representative immunofluorescence images and quantification in HeLa cells. ***P<0.001 by one way ANOVA with Tukey's multiple comparisons test.

FIGS. 2A-D presents exemplary data showing that a modified NLS nickase Cas9 (nCas9) PE composition enhances editing efficiency.

Figure 2A:
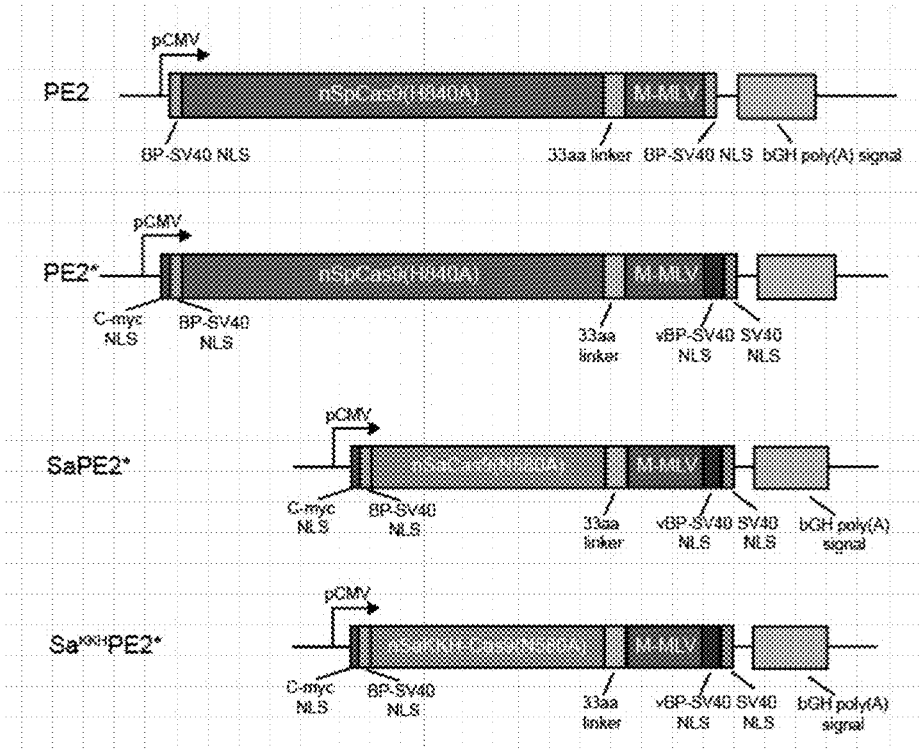

FIG. 2A: A schematic representation of: i) a 2×BP-SV40 NLS-nSpCas9 (PE2); ii) a 1×C-myc NLS, 1×BP-SV40 NLS, 1×vBP-SV40 NLS-nSpCas9, 1×SV40 NLS (PE2*); iii) a 1×C-myc NLS, 1×BP-SV40 NLS, lxvBP-SV40, 1×SV40 NLS NLS-nSaCas9 (SaPE2*); and iv) a 1×C-myc NLS, lxBP-SV40 NLS, 1×vBP-SV40, 1×SV40 NLS NLS-nSaCas9$^{KKH}$ (Sa$^{KKH}$ pE2*). M-MLV=reverse transcriptase. vBP-SV40 NLS=variant BP-SV40 NLS.

Figure 2B:
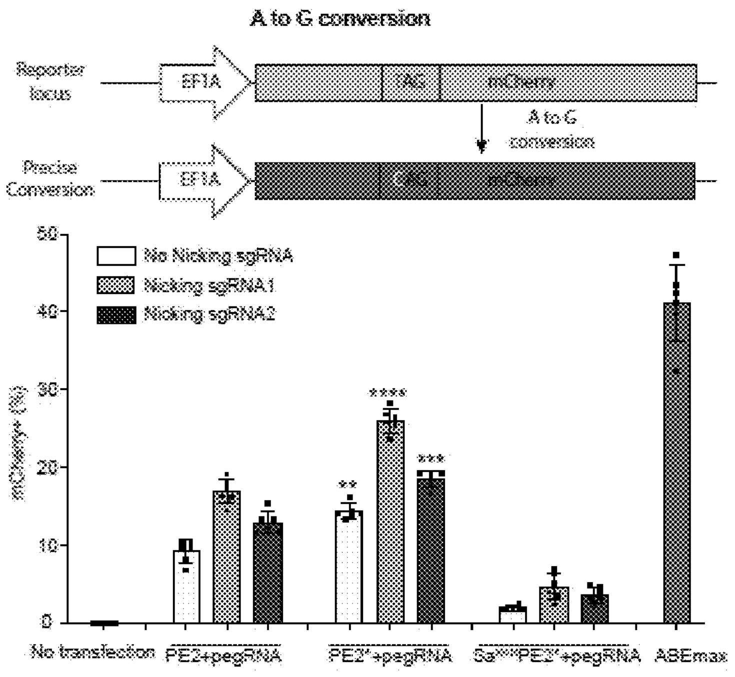

FIG. 2B: A diagram of a A•T-to-G•C conversion required to modify a stop codon into a GLN codon to restore function to an mCherry reporter in HEK293T cells (top). Frequencies of targeted A•T-to-G•C conversion by different prime editors (PE2, PE2* and Sa$^{KKH}$PE2*) were quantified by flow cytometry (bottom).

Figure 2C:
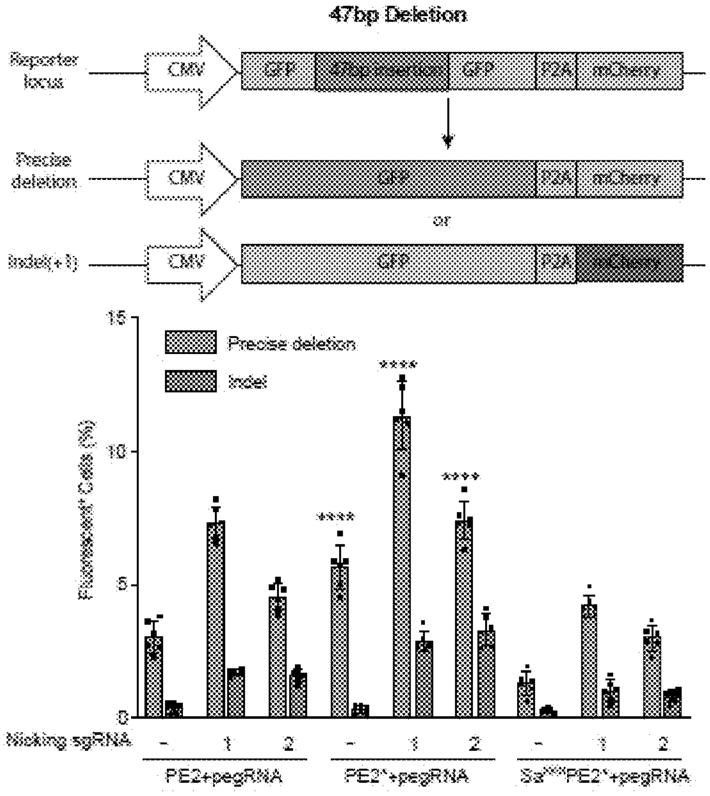

FIG. 2C: A diagram of a deletion reporter in HEK293T cells containing a broken GFP with 47-bp insertion, P2A, and out-of-frame mCherry (top). A targeted, precise deletion of 47bp restores GFP expression, whereas indels that create a particular reading frame alteration produce mCherry expression. Frequencies of precise deletion (GFP$^{+}$) and indel (mCherry$^{+}$) introduced by different prime editors (PE2, PE2*, and Sa$^{KKH}$ PE2*) were quantified by flow cytometry (bottom).

Figure 2D:
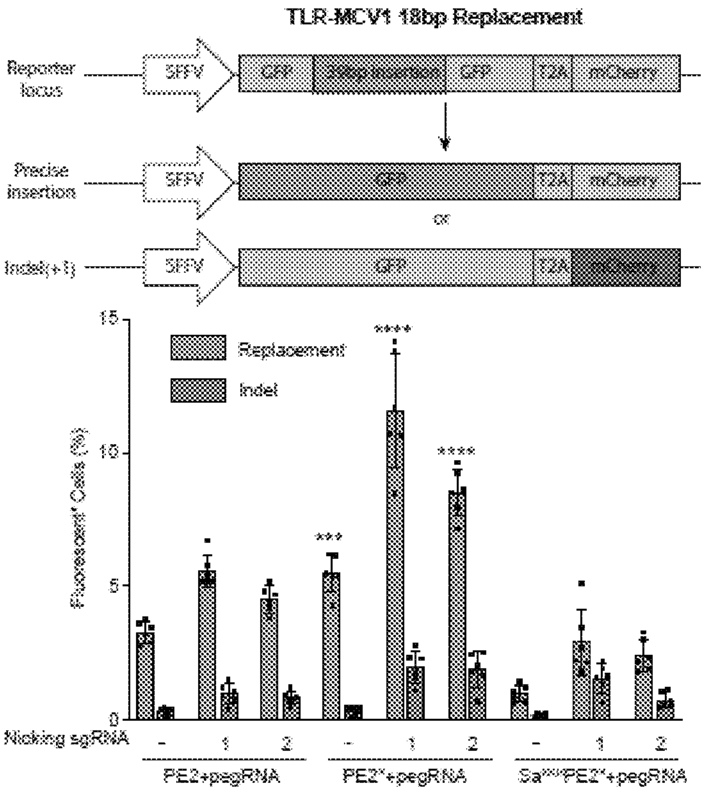

FIG. 2D: A diagram of an insertion reporter in HEK293 cells containing a broken GFP with 39-bp insertion, T2A and mCherry (top). A targeted, precise insertion of 18 bp that substitutes for a disrupting sequence restores GFP expression, whereas indels that create a particular reading frame alteration produce mCherry expression. Frequencies of targeted 18-bp replacement and indel generation by different prime editors (PE2, PE2*, and $Sa^{KKH}$ PE2*) were quantified by flow cytometry (bottom).

All expression vectors were delivered by transient transfection. The presence of sgRNAs to promote nicking of the complementary strand is indicated in each figure legend. Results were obtained from six independent experiments and presented as mean±SD. P<0.01, *P<0.001, ****P<0.0001 by one-way ANOVA with Tukey's multiple comparisons test between each PE2 and PE2* using the same nicking sgRNA.

FIGS. 3A-D presents exemplary data of Prime editing in reporter cells by PE2 and PE2*.

Figure 3A:
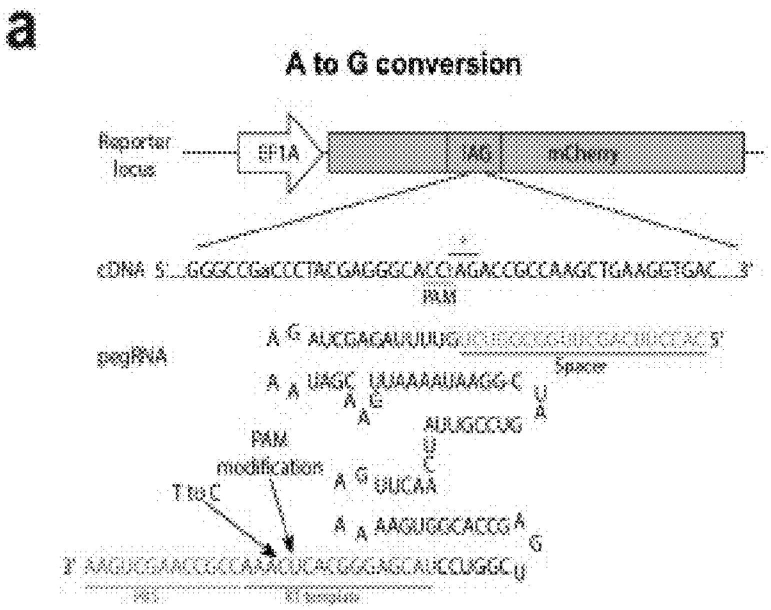

FIG. 3A: Sequence of the mCherry reporter locus and pegRNA used for repair (via A•T-to-G•C conversion) in HEK293T cells. Bar above the cDNA indicates the stop codon with the target "t" for conversion indicated in red. Two additional silent mutations are included to reduce recutting of the repaired DNA sequence.

Figure 3B:
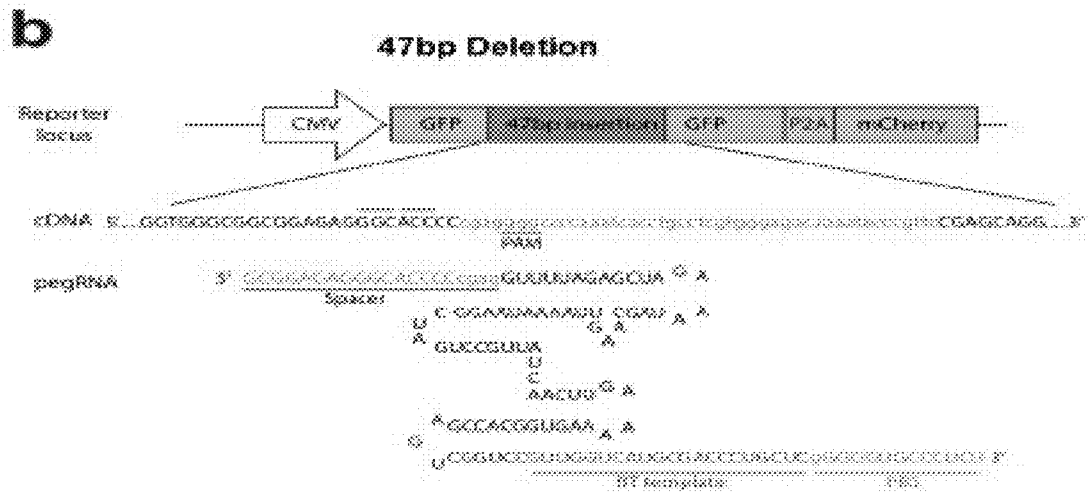

FIG. 3B: Sequence of the GFP reporter and pegRNA used for generation of a 47 bp deletion to restore function in HEK293T cells. The bars above the cDNA indicates three nucleotide blocks that correspond to codons in the GFP reporter.

Figure 3C:
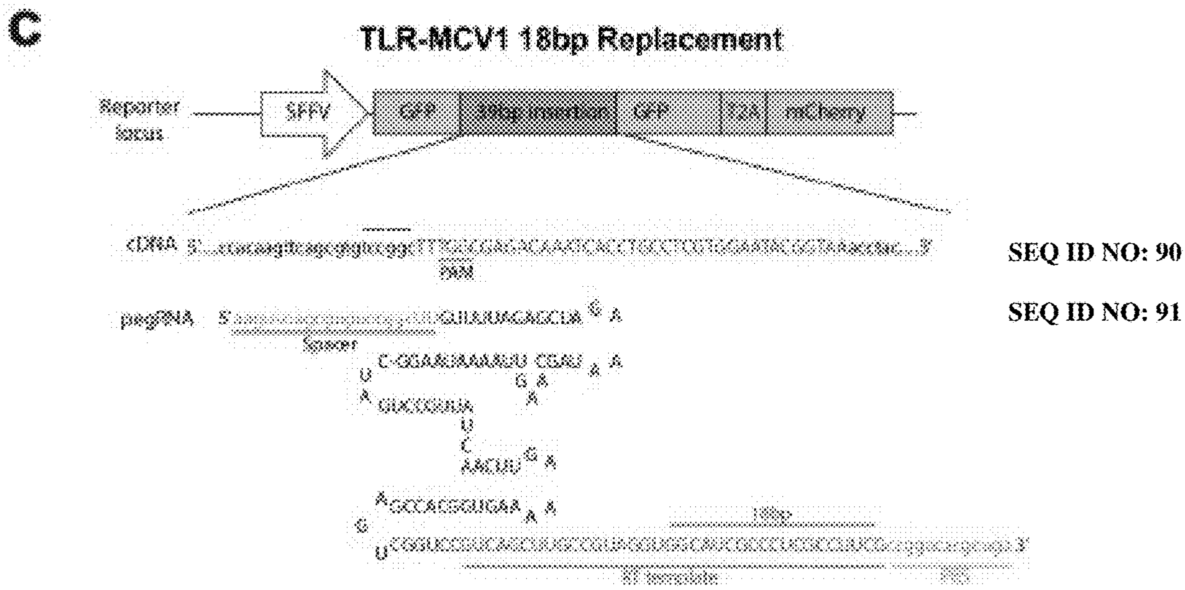

FIG. 3C: Sequence of the GFP reporter and pegRNA used for replacement of a 18 bp element to restore function. The bars above the cDNA indicates three nucleotide blocks that correspond to codons in the GFP reporter.

Figure 3D:
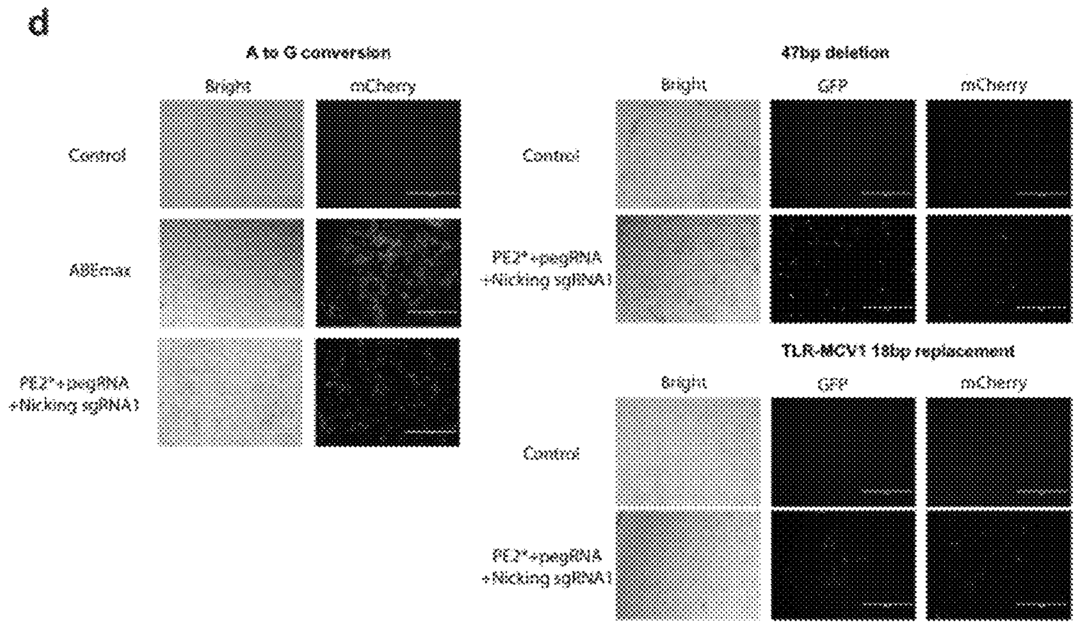

FIG. 3D: Representative images of HEK293T reporter cells transfected with control, ABEmax or PE2*. Scale bar, 400 μm.

FIGS. 4A-E presents exemplary data showing that PE2* increases editing efficiency at endogenous loci.

FIG. 4A: Comparison of editing efficiency for nucleotide conversion, targeted 3-bp deletion, and 6-bp insertion with PE2 and PE2* at EMX1 locus in HEK293T cells. Indels broadly indicate mutations to an endogenous sequence that do not result in the desired sequence alteration.

FIG. 4B: Editing efficiency for nucleotide conversion, targeted 3-bp deletion, and 6-bp insertion with Sa PE2* at EMX1 locus in HEK293T cells FIG. 4C: Editing efficiency for nucleotide conversion, targeted 3-bp deletion, and 6-bp insertion with $Sa^{KKH}$ PE2* at EMX1 locus in HEK293T cells.

Figure 4D:
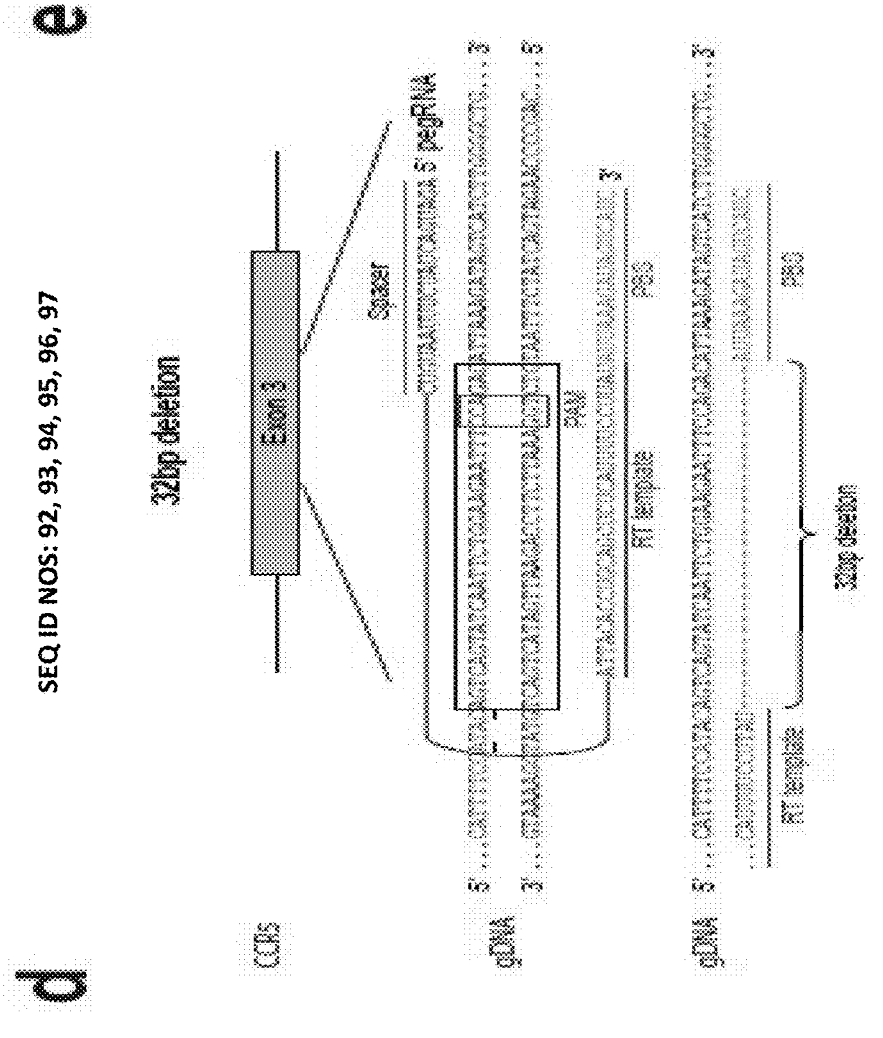

FIG. 4D: Sequence of the CCR5 locus and pegRNA used for the 32 bp deletion. Two mutations in red were included to demonstrate that sequence collapse was not a function of nuclease-induced microhomology mediated deletion and to reduce re-cutting of deletion allele. Bottom panel shows the alignment of pegRNA with the CCR5 sense strand.

Figure 4E:
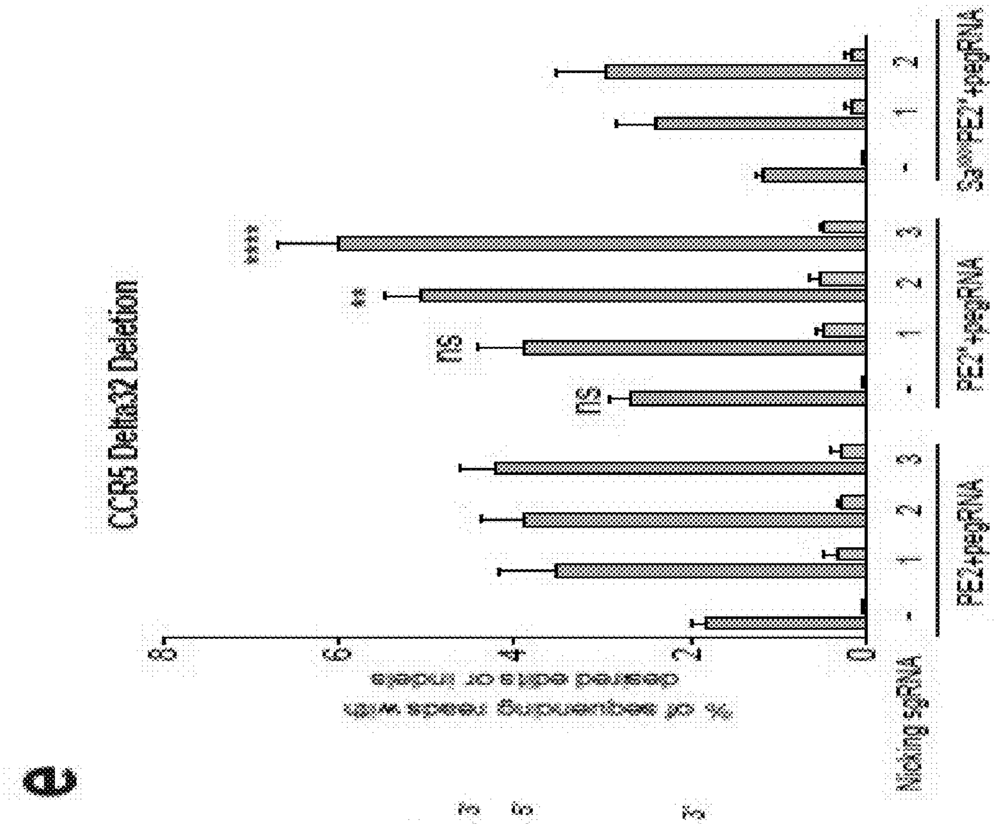

FIG. 4E: Comparison of efficiency for generating a targeted 32-bp deletion with PE2, PE2*, and $Sa^{KKH}$ PE2* within CCR5 in HeLa cells.

All expression vectors were delivered by transient transfection. The presence of sgRNAs to promote nicking of the complementary strand is indicated in each figure panel. Results were obtained from three independent experiments and presented as mean±SD. *P<0.05, P<0.01, *P<0.001, ****P<0.0001 by one-way ANOVA with Tukey's multiple comparisons test. ns, not significant.

Figure 5:
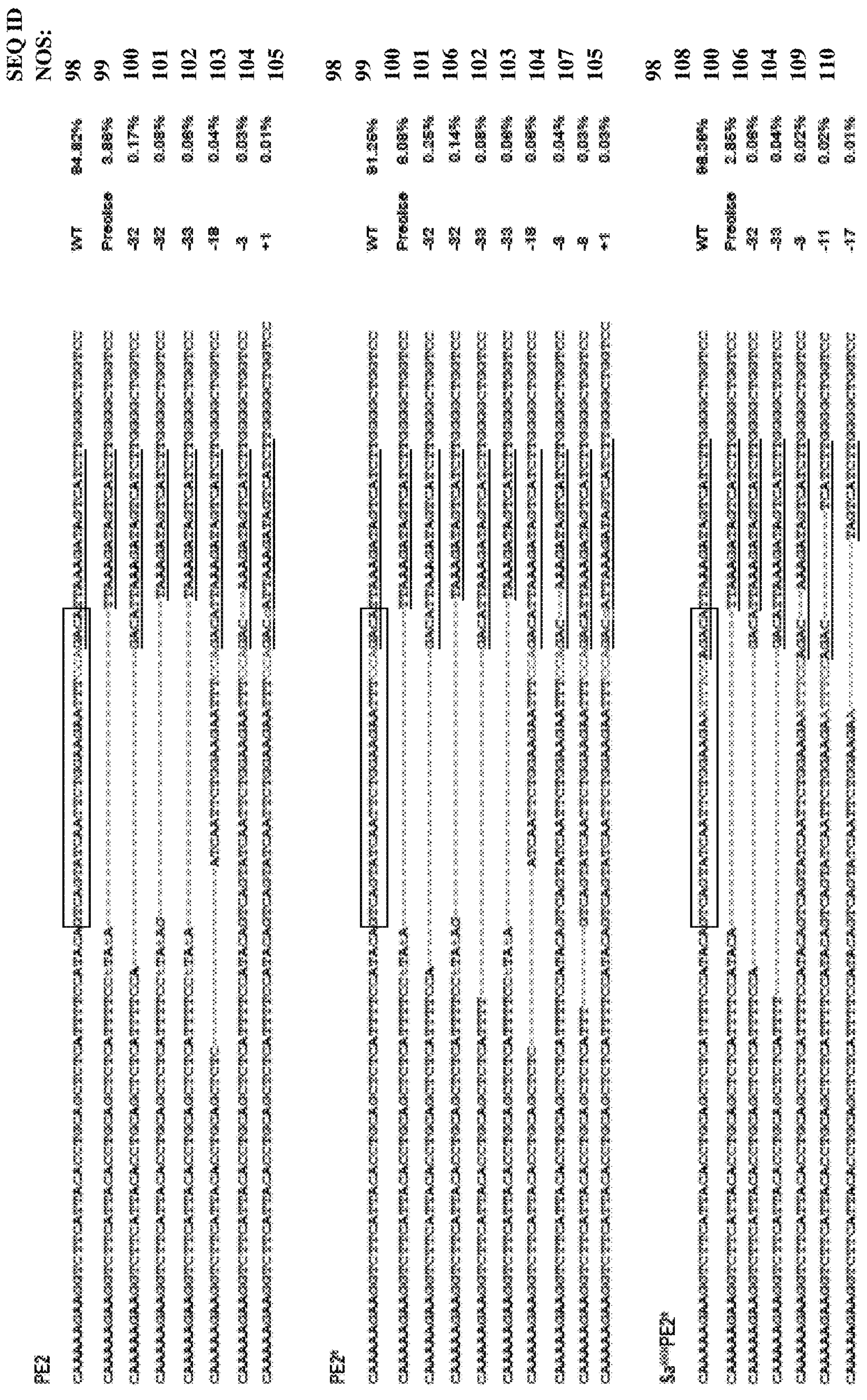

FIG. 5 presents an exemplary sequencing analysis of CCR5 prime editing by PE2, PE2* and $Sa^{KKH}$ PE2*. The percentage of common sequences in PE2, PE2* and $Sa^{KKH}$PE2* transfected cells is shown on the right (representative of n=3, determined by Illumina sequencing). The PE target site is underlined. The PAM sequences are indicated in light blue for SpCas9 and green for SaCas9KKH. The box denotes the 32 bp sequence deleted in CCR5delta32. Two "t" mutations in red were included in the PE2 and PE2* RT template sequence in accordance with FIG. 4D to demonstrate that sequence collapse was not a function of nuclease-induced microhomology mediated deletion and to reduce re-cutting of deletion allele. Deleted bases are indicated by dashes and inserted bases are in blue.

FIGS. 6A-D presents exemplary data showing that an enhanced PE2* increases the correction efficiency of a pathogenic mutation in vivo.

Figure 6A:
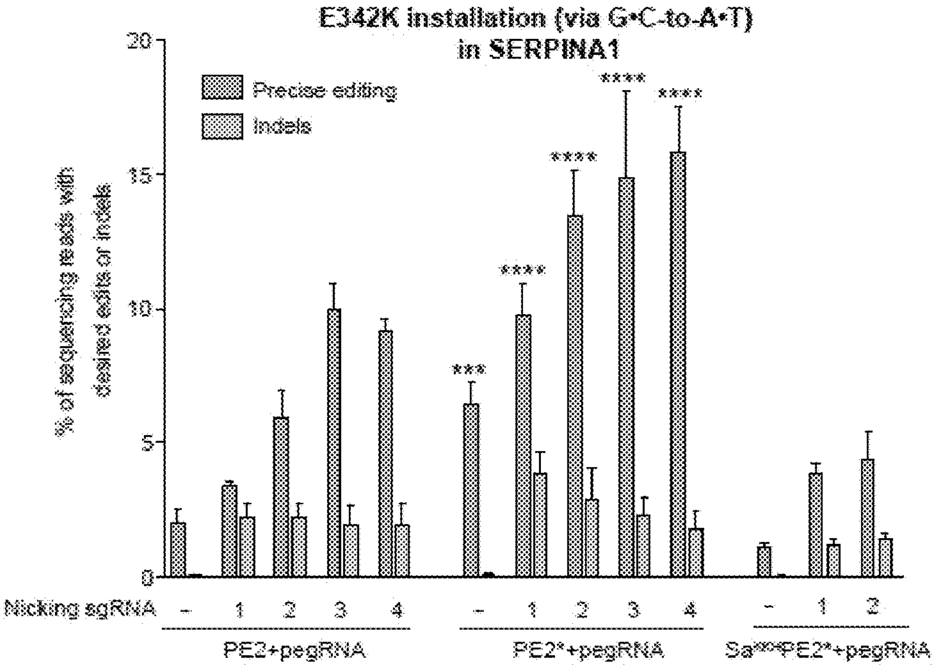

FIG. 6A: Installation (via G•C-to-A•T) of the pathogenic SERPINA1 E342K mutation in HEK293T cells using PE2, PE2*, and $Sa^{KKH}$PE2*. Editing efficiencies reflect sequencing reads which contain the desired edit. The presence of sgRNAs to promote nicking of the complementary strand is indicated on the x-axis. Results were obtained from three independent experiments and are presented as mean±SD.

Figure 6B:
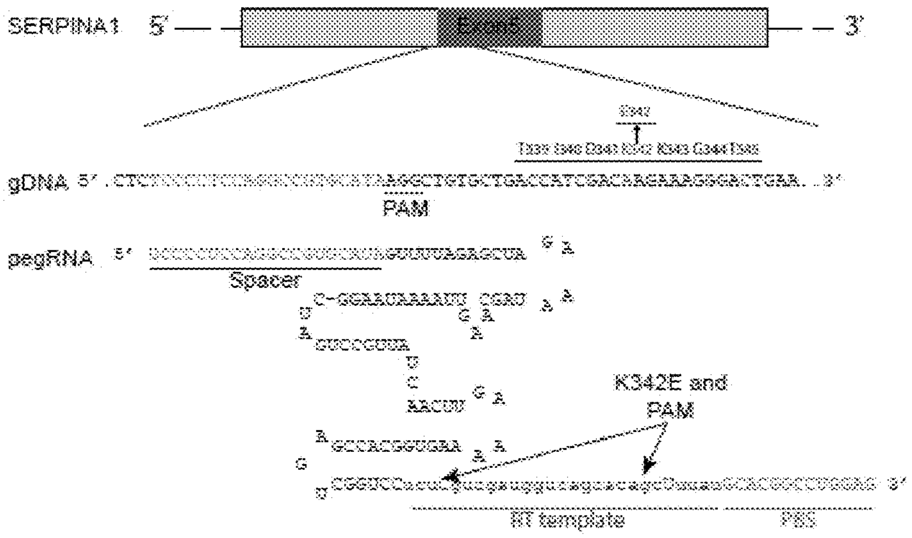

FIG. 6B: pegRNA used for correction (via A•T-to-G•C) of the E342K mutation includes a spacer sequence, a sgRNA scaffold, an RT template including edited bases (red) and a primer-binding site (PBS). A PAM mutation (AGG→AAG) was introduced to reduce re-cutting of the locus that results in a synonymous codon change.

Figure 6C:
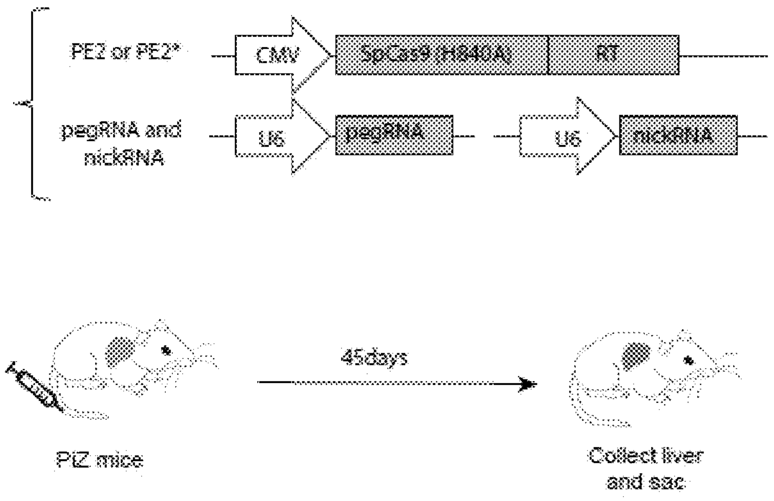

FIG. 6C: Schematic overview of correction strategy of the SERPINA1 E342K mutation in PiZ transgenic mouse model of AATD. Prime editor, pegRNA and nicking sgRNA plasmid were delivered by hydrodynamic tail-vein injection.

Figure 6D:
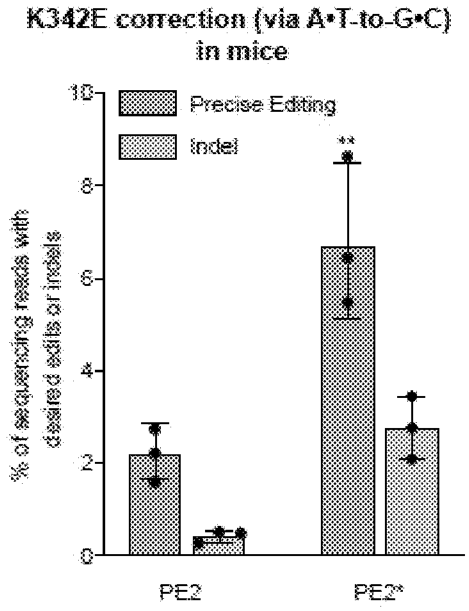

FIG. 6D: Comparison of the efficiency of K342E correction and indels in mouse livers in PE2 or PE2* treatment groups. Precise editing is defined as the fraction of sequencing reads with both A to G prime editing and synonymous PAM modification.

Results were obtained from three mice and presented as mean±SD. P<0.01, *P<0.001, ****P<0.0001 by one-way ANOVA with Tukey's multiple comparisons test.

Figure 7A:
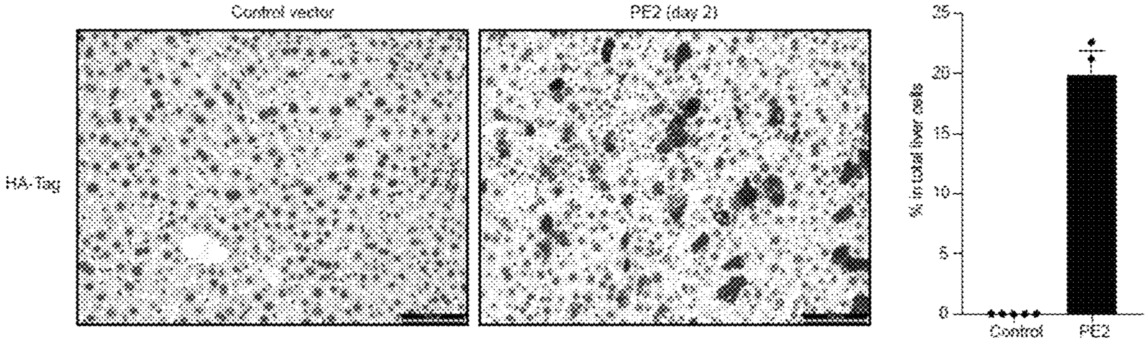
Figure 7B:
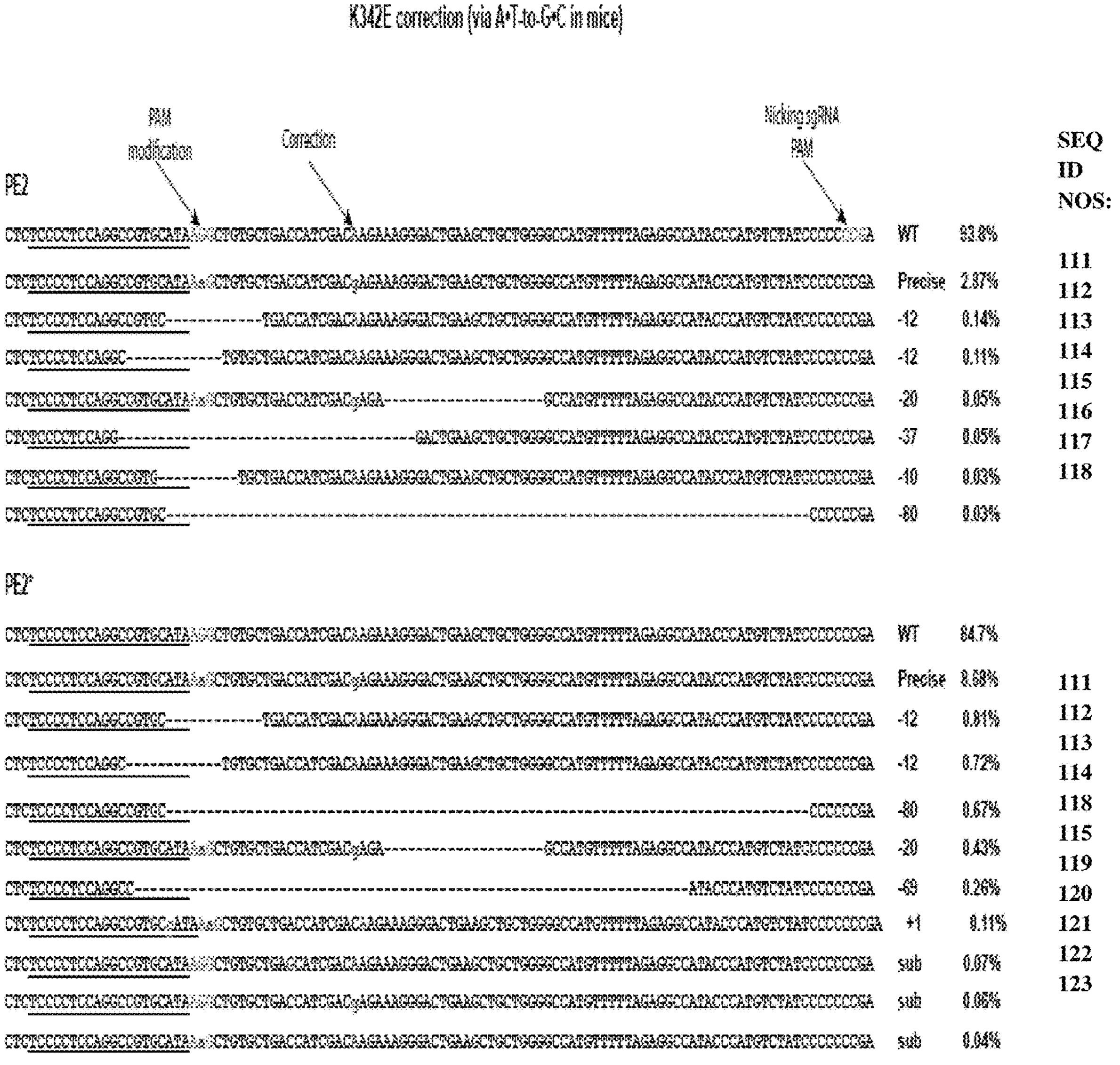

FIGS. 7A-B presents exemplary data of a sequencing analysis of SERPINA1 editing in the liver of PiZ mouse.

FIG. 7A: Evaluating prime editor expression in mouse liver. Left panel: FVB mice were injected with 30 μg of control vector or PE2 plasmid with HA-tag. Livers were harvested at day 2 and IHC staining were performed with an HA-tag antibody. Representative IHC images are shown. Scale bars: 100 μm (20× lens). Right panel: Quantification of HA+ cells. Numbers are mean+sem (n=4 718 mice).

FIG. 7B: The percentage of most common sequences in the liver of PE2 and PE2*-treated mice is shown on the right (representative liver of n=3, determined by Illumina sequencing). The PE target site is underlined. The PAM sequences are in light blue. Nucleotide substitutions are labeled in red. Deleted bases are indicated by dashes. Inserted bases are shown in blue/lower case.

FIGS. 8A-H presents exemplary data showing the generation of mouse cancer models using improved PE2*.

Figure 8A:
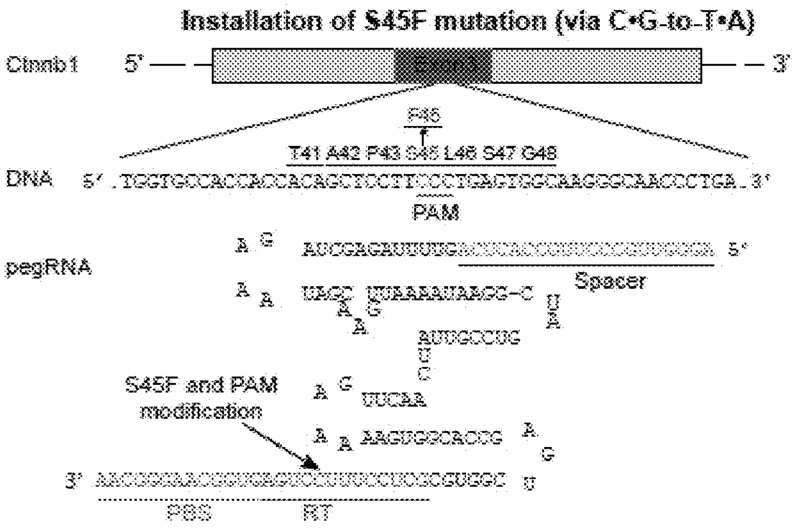

FIG. 8A: pegRNA used for installation (via C•G-to-T•A) of the oncogenic S45F in Ctnnb1 in mouse liver.

Figure 8B:
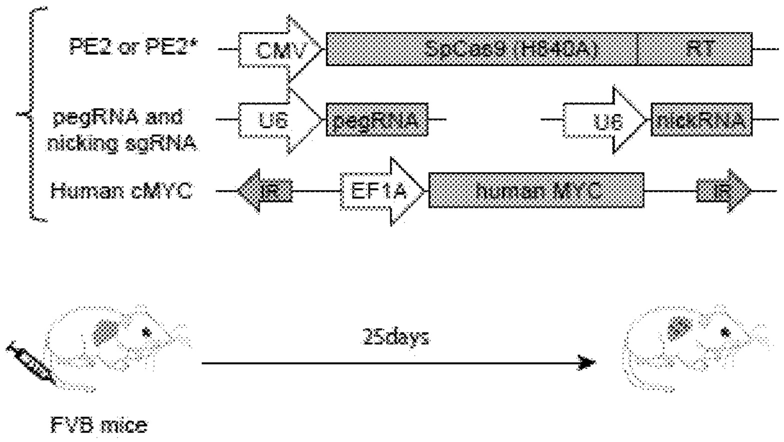

FIG. 8B: Schematic overview of the somatic cell editing strategy to drive tumor formation. Prime editor (PE2 or PE2*), pegRNA for Ctnnb1 S45F and nicking sgRNA plasmids were delivered by hydrodynamic tail-vein injection along with the MYC transposon and transposase plasmids.

Figure 8C:
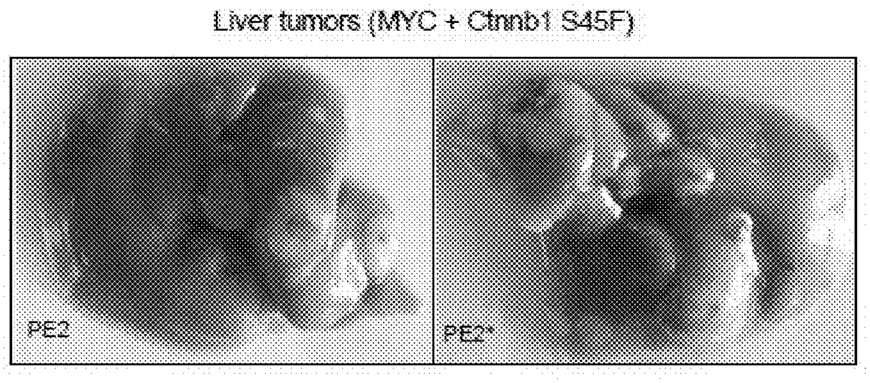

FIG. 8C: Representative images of tumor burden in mouse liver with PE2 or PE2*.

Figure 8D:
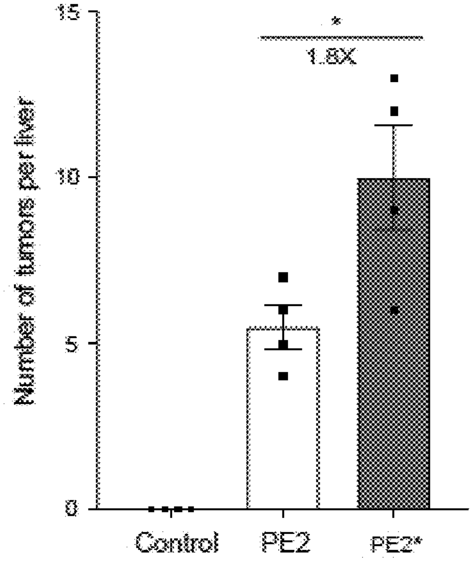

FIG. 8D: Tumor numbers in the livers of mice 25 days after injection with PE2 or PE2*. Control group was pegRNA only.

Figure 8E:
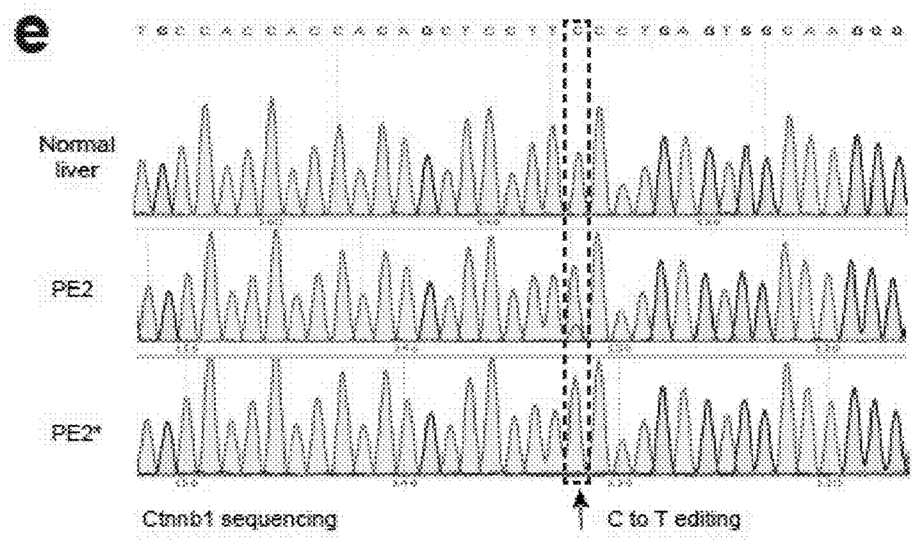

FIG. 8E: Sanger sequencing from normal liver and representative tumors. The dashed box denotes C to T editing in tumors. *P<0.05 by one-way ANOVA with Tukey's multiple comparisons test.

Figure 8F:
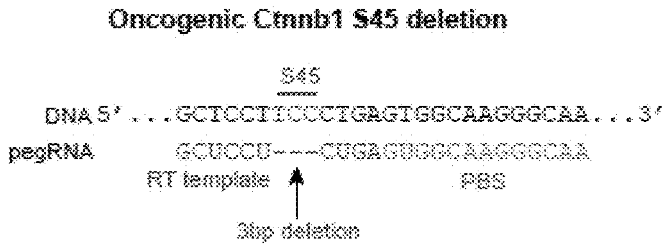

FIG. 8F: Schematic of Ctnnb1 S45 deletion strategy using PE2* (S45del). pegRNA used for 3 bp deletion (TCC) is shown.

Figure 8G:
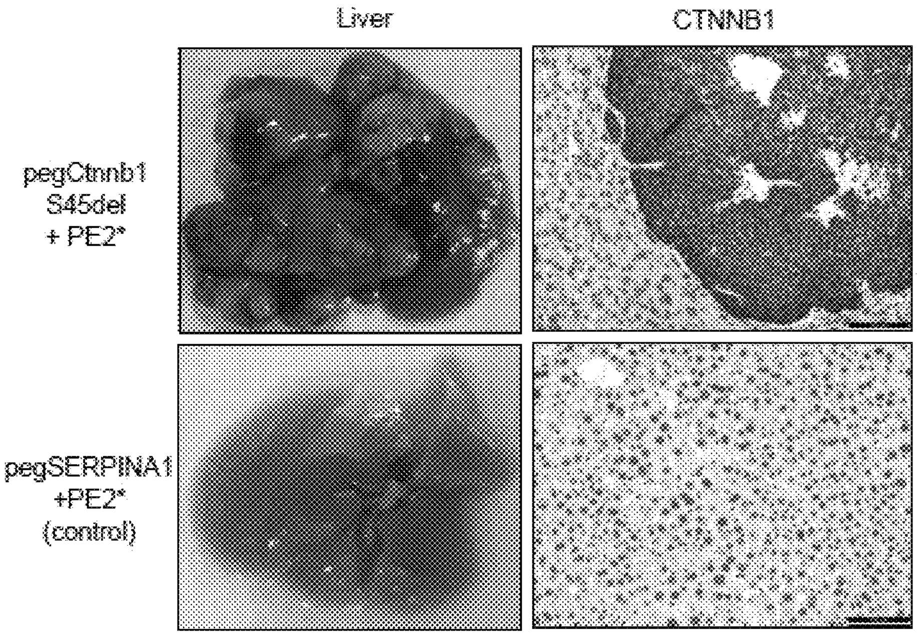

FIG. 8G: PE2* treatment leads to oncogenic activation of Ctnnb1. Prime editor (PE2*), pegRNA (Ctnnb1 S45del or SERPINA1) and nicking sgRNA plasmids were delivered by hydrodynamic tail-vein injection along with the MYC transposon and transposase plasmids. Mice treated with the pegCtnnb1 S45del (n=4) displayed a large number of liver tumors whereas mice treated with pegSERPINA1 as a control displayed no noticeable oncogenic lesions. beta-Catenin (CTNNB1) IHC staining was performed. Scale bars: 100 μm (20× lens).

Figure 8H:
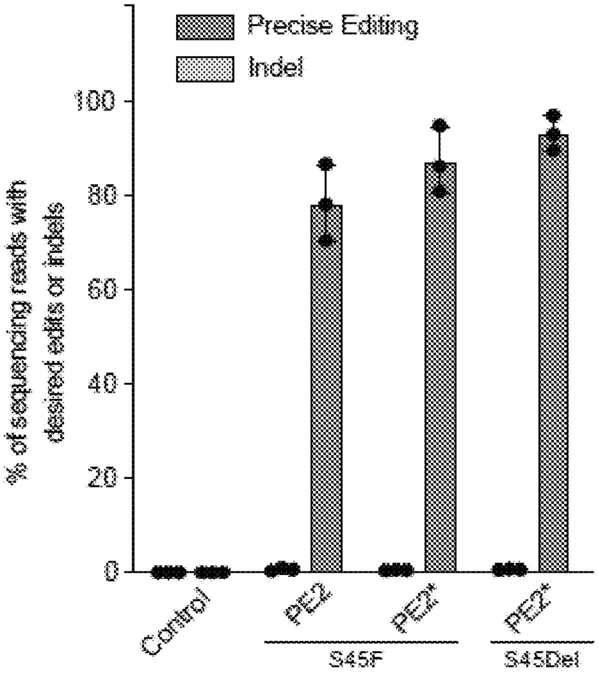

FIG. 8H: Prime editing efficiency and indels determined by targeted deep sequencing in control liver and representative tumors.

Figure 9:
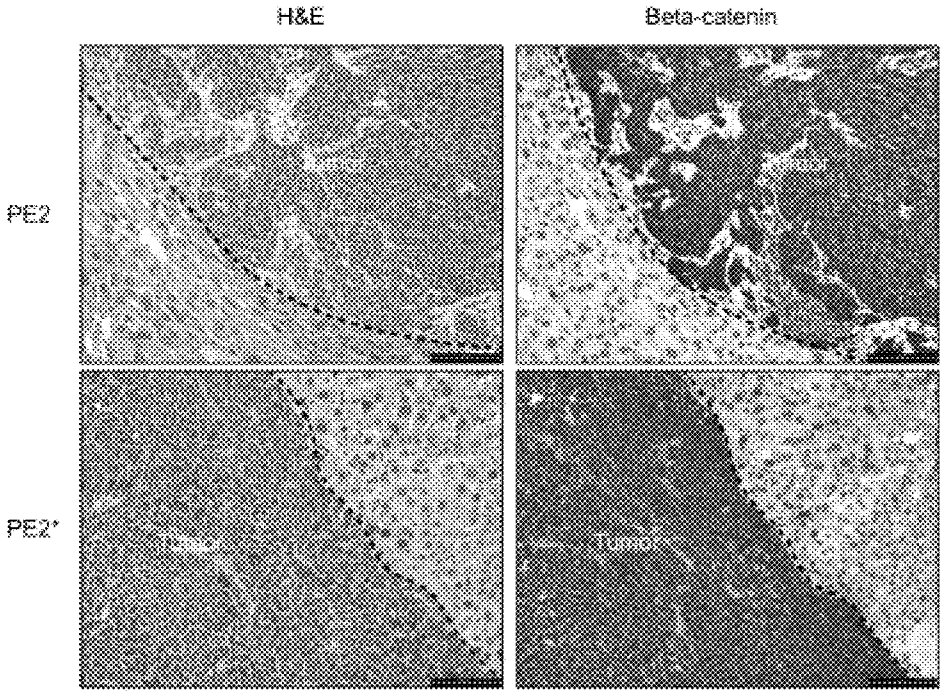

FIG. 9 presents exemplary photomicrographs of liver tumors which are positive for nuclear beta-Catenin. Representative H&E and beta-catenin IHC staining in PE2 or PE2*-induced S45F tumors. Scale bars: 726 100 μm (20× lens).

FIGS. 10A-E presents exemplary data showing that a systemic injection of a dual AAV8 split-intein prime editor achieves pathogenic mutation correction in PiZ mice.

Figure 10A:
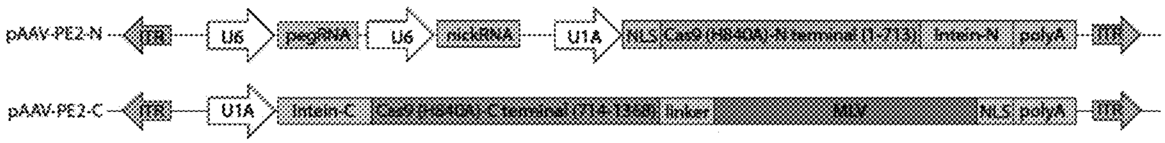

FIG. 10A: Schematic of split-intein dual AAV prime editor. A full-length prime editor (PE2) was reconstituted from two PE2 fragments employing the Npu DNAE split intein. C, carboxy terminal; N, amino terminal. Zettler et al., "The naturally split Npu DnaE intein exhibits an extraordinarily high rate in the protein trans-splicing reaction" *FEBS Lett* 583:909-914 (2009).

Figure 10B:
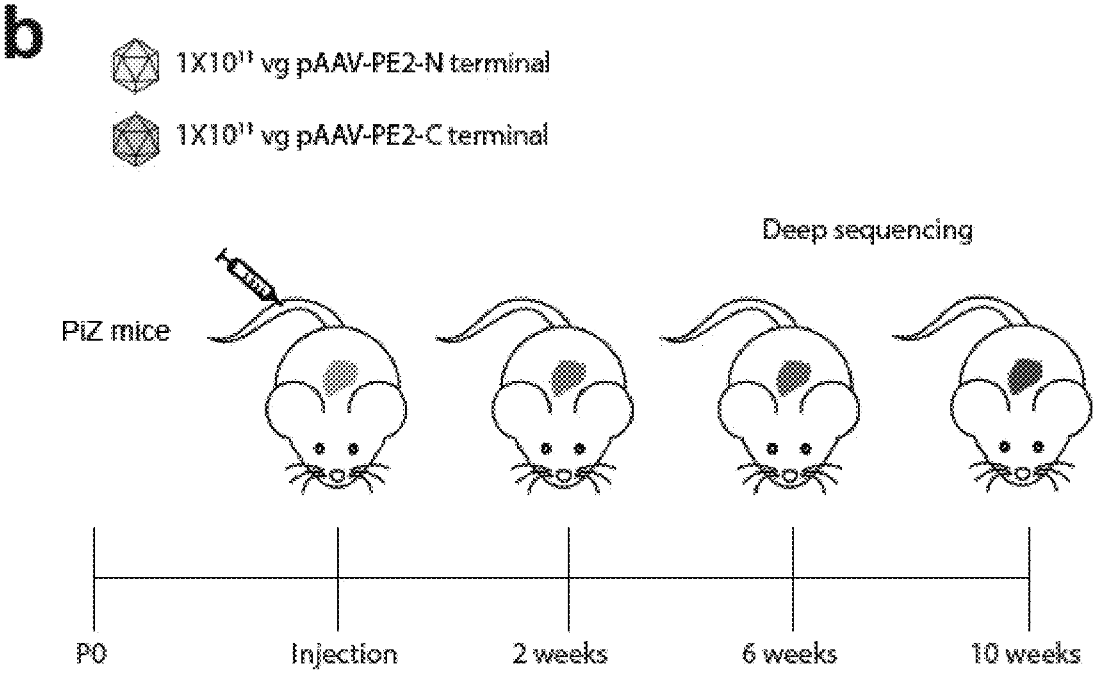

FIG. 10B: Schematic of the in vivo dual AAV8 prime editor injection experiments. Dual AAV8 split-intein prime editor ($2\times10^{11}$ vg total) was delivered to six-week-old PiZ mice by tail-vein injection. Livers were harvested at 2 (n=2), 4 (n=3) and 10 (n=3) weeks after injection and the genomic DNA was isolated for sequencing.

Figure 10C:
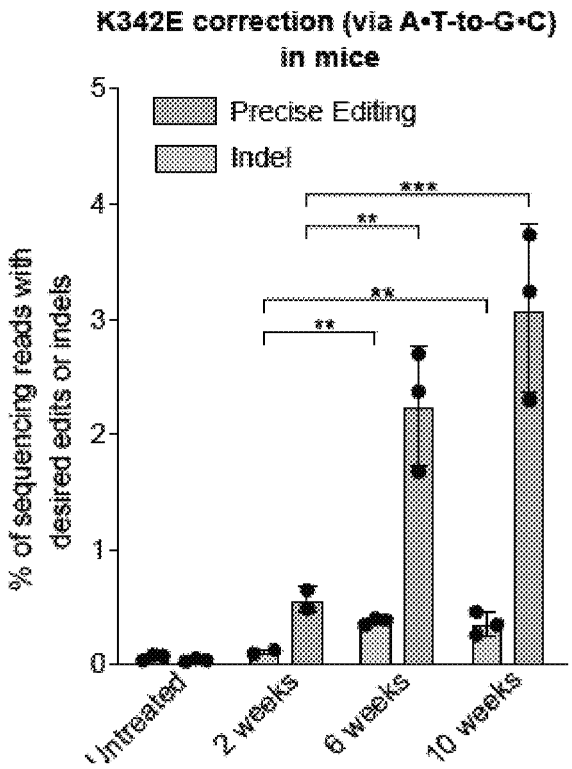

FIG. 10C: Prime editing efficiency of K342E correction and indels determined by targeted deep sequencing in mouse livers of dual AAV-treated mice. Precise editing is defined as the fraction of sequencing reads with both A to G prime editing and synonymous PAM modification. Results were obtained from two (2 weeks) or three mice (6 and 10 weeks) and presented as mean±SD. P<0.01, *P<0.001 by one-way ANOVA with Tukey's multiple comparisons test.

Figure 10D:
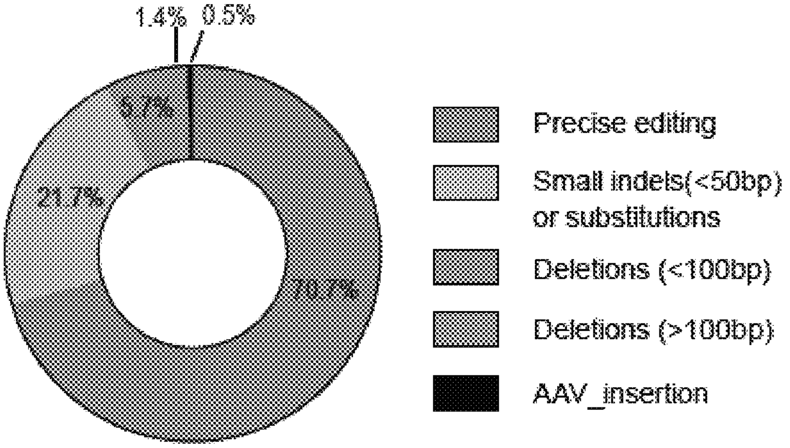

FIG. 10D: Composition of edited alleles at SERP1NA1 by UDiTaS analysis. Circle plot shows the fraction of edits that are precise (intended base conversion), small indels (<50 bp) or substitution, deletions between pegRNA and nicking sgRNA sites (<100 bp), large deletions (>100 bp), and AAV fragment insertion. Numbers are average of 3 mice in 10 week treated cohort.

Figure 10E:
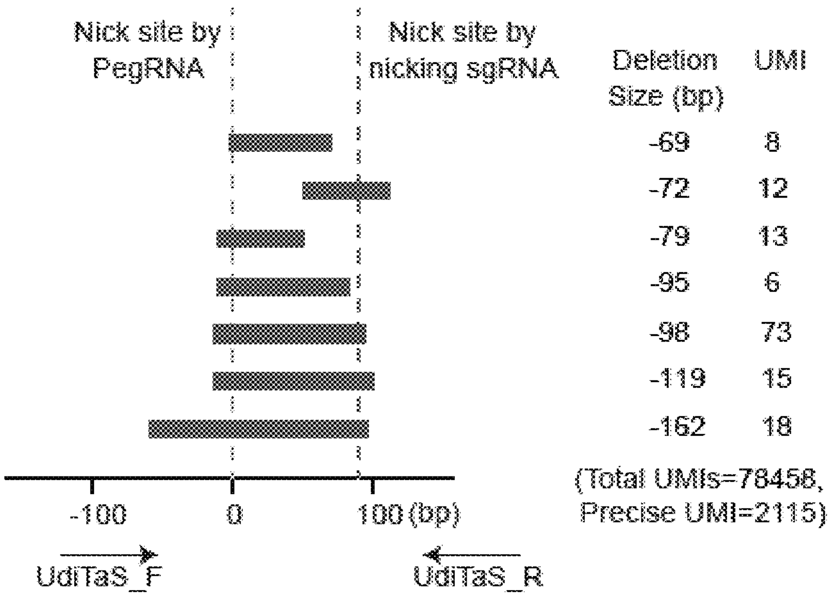

FIG. 10E: The statistically significant large deletion sequences detected by UDiTaS in the 10 week treated cohort are displayed as bars spanning the sequence that is deleted (a representative liver of n=3 mice). Positions of the pegRNA and nicking sgRNA are indicated by dotted lines and the approximate positions of the locus-specific UDiTaS primers are indicated by arrows below the bar chart. The deletion size and number of UMIs associated with each deletion are indicated to the right of each bar.

Figure 11A:
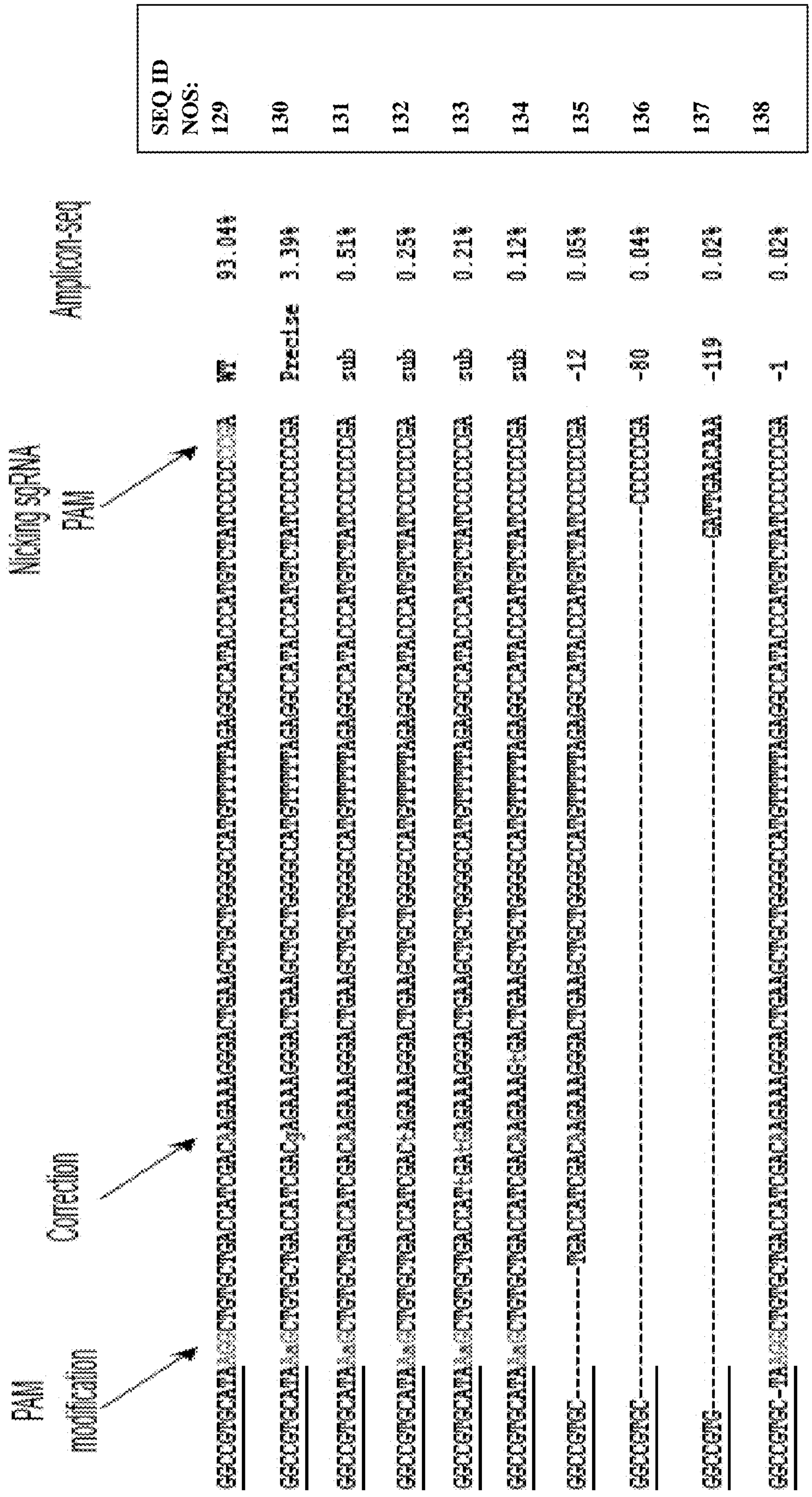
Figure 11B:
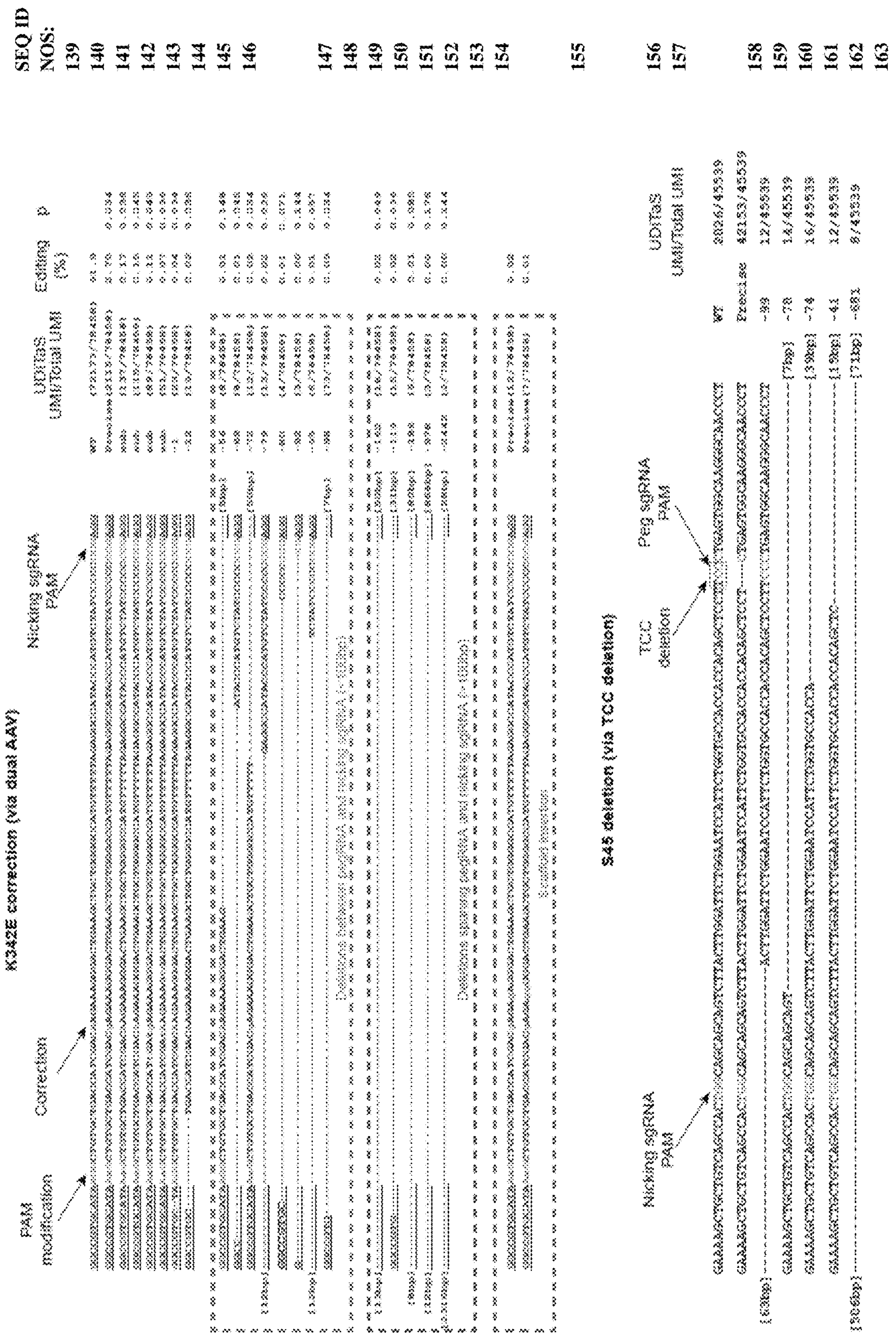

FIGS. 11A-B presents an exemplary sequencing analysis of the Ctnnb1 and SERPINA1 prime editing by PE2 or PE2*.

FIG. 11A: The percentage of most common sequences in the liver of dual AAV-treated PiZ mice determined by locus amplification is shown on the right (representative liver of n=3). A portion of the PE target site is underlined. The PAM sequences are in light blue. Nucleotide substitutions are labeled in red. Deleted bases are indicated by dashes.

FIG. 11B: Length distribution of precise editing and other indels at SERPINA1 (K342E correction) and Ctnnb1 target sites by UDiTaS. Also included are sequence modifications that may be associated with pegRNA scaffold insertions. A representative liver is shown (n=3 mice).

DETAILED DESCRIPTION OF THE INVENTION

This invention is related to the field of genetic engineering. In particular, compositions and methods that specifically and accurately repair genetic mutations that are responsible for the expression of a genetic disease. For example, a Cas9 complex modified as a prime editor and a plurality of nuclear localization signals. The therapeutic use of such modified Cas9 complexes repair genetic mutations with a higher efficiency, without repair-related indels and reduce the symptomology of a genetic disease.

In one embodiment, the present invention contemplates a modified NLS SpCas9-based prime editor that improves genome editing efficiency in both fluorescent reporter cells and at endogenous loci in cultured cell lines. Using this genome modification system, tumor formation was seeded through somatic cell editing in the adult mouse. A successful utilization of a dual adeno-associated virus (AAVs) delivered a split-intein prime editor and demonstrated that this system enables the correction (e.g., conversion) of a pathogenic mutation in the mouse liver. Although it is not necessary to understand the mechanism of an invention, it is believed the present embodiments may further establish the broad potential of this new genome editing technology for the directed installation of sequence modifications in vivo, with implications for disease modeling and correction of mutated genomes and/or alleles to wild type sequences for successful therapies for genetic disease or disorders.

The data presented herein demonstrates the in vivo editing of somatic cells in mammalian systems by prime editing. A utility of prime editing systems is exemplified for two different types of applications: i) the correction and/or conversion of a pathogenic mutation (AATD); and ii) the generation of animal cancer model by insertion and/or deletion of specific nucleic acid sequences linked to cancers. Precise deletion of a pathogenic mutation or insertion of somatic mutations in vivo is relevant to both gene therapy and the development of new animal models to study medical disorders. Maddalo et al., "In vivo engineering of oncogenic chromosomal rearrangements with the CRISPR/Cas9 system" Nature 516 (2014). Using hydrodynamic injection, the presently disclosed improved PE2* shows an approximately twelve-fold (12×) higher editing efficiency (~6%) than previously published HDR (~0.5%) in the mouse liver for installing oncogenic point mutations. Xue et al., "CRISPR-mediated direct mutation of cancer genes in the mouse liver" Nature 514:380-385 (2014).

I. Conventional Prime Editor Systems

Prime editors (PEs) are believed to mediate genome modification without utilizing double-stranded DNA breaks or exogenous donor DNA as a template. PEs may facilitate nucleotide substitutions or local nucleic acid sequence insertions or nucleic acid sequence deletions within the genome based on a reverse transcriptase-template ribonucleic acid sequence encoded within the prime editing guide RNA (pegRNA). However, the efficacy of prime editing in adult mice has not been established.

The prime editor (PE) is a genome editing tool that can produce template-directed local sequences changes in the genome without the requirement for a DSB or exogenous donor DNA templates. A PE comprises a fusion protein including a catalytically impaired Cas9 nickase (e.g., Spcas9$^{H840A}$) and an engineered reverse transcriptase (RT). A prime editing guide RNA (pegRNA) targets the PE to a desired genomic sequence and encodes a primer binding site (PBS) and a nucleic acid sequence template for a reverse transcriptase protein which results in the integration of new genetic information into the target genomic locus. Prime editing can result in nucleotide conversion, targeted sequence insertions and targeted sequence deletions. In particular, PE2 comprises five (5) mutations within the M-MLV RT sequence that improves editing efficiency. In comparison, PE3 uses an additional sgRNA to direct SpCas9$^{H840A}$ to nick a non-edited DNA strand such that the edited strand may be utilized as a repair template by DNA repair factors, leading to further increases in editing efficiency. Anzalone et al., "Search-and-replace genome editing without double-strand breaks or donor DNA" *Nature* 576: 149-157 (2019).

Correction of genetic mutations in vivo is thought to have broad potential therapeutic application for a range of human genetic diseases. Prime editors (PE) composed of a Cas9 nickase and engineered reverse transcriptase have enabled precise nucleotide changes, sequence insertions and deletions. Anzalone et al., "Search-and-replace genome editing without double-strand breaks or donor DNA" *Nature* 576: 49-157 (2019). This innovative technology has not been shown to induce double-stranded DNA breaks or require a donor DNA template in conjunction with homology directed repair to introduce precise sequence changes into the genome.

The efficacy of genome editing systems is dependent on a number of factors, one of which is the efficiency of nuclear import. In rapidly proliferating cells, the nuclear envelope provides only a modest barrier to entry for genome editing tools. However, in post-mitotic or quiescent cells the nuclear envelope may provide a greater barrier to the entry of Cas9-based systems, such that the number and composition of the NLS sequences can impact editing efficacy. Suzuki et al., "In vivo genome editing via CRISPR/Cas9 mediated homology independent targeted integration" *Nature* 540: 144-149 (2016); Wu et al., "Highly efficient therapeutic gene editing of human hematopoietic stem cells" *Nat Med* 25:776-783 (2019); Koblan et al., "Improving cytidine and adenine base editors by expression optimization and ancestral reconstruction" *Nat Biotechnol* (2018); Zafra et al., "Optimized base editors enable efficient editing in cells, organoids and mice" *Nat Biotechnol* (2018); Song et al., "Adenine base editing in an adult mouse model of tyrosinaemia" *Nature Biomedical Engineering* 4:125-130 (2020); and Walton et al., "Unconstrained genome targeting with near-PAM less engineered CRISPR-Cas9 variants" *Science* (2020).

II. Nuclear Localization Signal Sequence Prime Editor Systems

The ability to precisely install or correct pathogenic mutations regardless of their composition makes prime editing an intriguing approach to perform somatic genome editing in model organisms to study disease processes or to utilize for therapeutic applications. Previous studies have used prime editing to recode loci in cultured cells, plants, stem cells, and mouse zygotes. Anzalone et al., "Search-and-replace genome editing without double-strand breaks or donor DNA" *Nature* 576:149-157 (2019); Lin et al., "Prime genome editing in rice and wheat" *Nat Biotechnol* 38:582-585 (2020); Schene et al., "Prime editing for functional repair in patient-derived disease models" *Nature Communications* 11:5352 (2020); Geurts et al., "Evaluating CRISPR-based Prime Editing for cancer modeling and CFTR repair in intestinal organoids" bioRxiv 2020.2010.2005.325837 (2020); Liu et al., "Efficient generation of mouse models with the prime editing system" *Cell Discov* 6:27 (2020); and Aida et al., "Prime editing primarily induces undesired outcomes in mice" *bioRxiv,* 760 2020.2008.2006.239723 (2020). However, PE delivery in adult animals has not yet been described.

By incorporating additional NLSs, an improved PE (PE2*) has been developed that increases the efficiency of genome editing across multiple endogenous sites relative to the original PE2. Importantly, the observed improvements in genome editing for PE2* in cell culture translated to increased rates of genome editing in vivo. Thus, demonstrating that NLS sequence composition and architecture is an important parameter to consider in the design of prime editing systems to maximize in vivo efficacy has been observed for other genome editing systems.

The data presented herein show a modified nuclear localization signal sequence prime editor system (PE2*) with higher editing efficiency than conventional PE2 systems in adult animals. For example, the embodiments disclosed herein include, but are not limited to:

a prime editor (PE2*) comprising NLS sequences that are modified in composition and number that improves prime editor (PE2) efficiency.

PE2* systems can correct a pathogenic genetic disease (e.g., alpha-1 antitrypsin deficiency (AATD)) using an in vivo plasmid delivery of a dual AAV prime editor system.

PE2* systems can be utilized to seed tumor formation for the study of oncogenic drivers in the mouse liver PE2* systems are exemplified by nSaCas9 PE2* and nSa$^{KKH}$ PE2* which introduced targeted genomic sequence alterations.

These data show that PE2* results in somatic genome editing in the liver of adult mice, where it corrects a pathogenic disease allele and/or introduces a directed mutation to drive tumor formation to facilitate cancer modeling. The size of a prime editor precludes its packaging in a single AAV vector. In one embodiment, a dual AAV-mediated delivery of a split-intein prime editor in mouse liver is functional in vivo for gene editing. These data demonstrate the feasibility of employing PE in vivo for the targeted, precise alteration of genomic sequence with a potential utility both in model organisms and as a therapeutic modality.

Conventional prime editing systems can also produce undesired editing outcomes in some instances. The use of the PE2 system in cell culture systems produces primarily precise edits. The rate of precise edits can be increased through the use of an additional nicking sgRNA (PE3 strategy), but this also results in the production of a low rate of indels within the genome.

Prime editing in plant protoplasts also produces a fraction of undesired editing outcomes when employing either the PE2 and PE3 strategy. Interestingly, in mouse zygotes the PE3 strategy produces alleles containing the desired edit, but a large fraction also harbor deletions of various sizes between the target site and the nicking site. Anzalone et al. (2019); Lin et al., "Prime genome editing in rice and wheat. *Nat Biotechnol* 38:582-585 (2020); and Aida et al., "Prime editing primarily induces undesired outcomes in mice. *BioRxiv,* 2020.2008.2006.239723 (2020).

In one embodiment, the present invention contemplates an in vivo PE3 editing method wherein the majority of modified alleles contain an intended product without additional modifications. For example, the data shows that only a small fraction of edited alleles contain unintended changes (i.e., indels). Furthermore, ~6.6% of these edited alleles contained deletions between the pegRNA and nicking sgRNA sites. In one embodiment, the method further comprises a sequential nicking with a PE3b prime editor. Although it is not necessary to understand the mechanism of an invention it is believed that a PE3b prime editor may reduce the indel rates in vivo, when an overlapping nicking RNA can be designed at the prime editor target site.

A. Nuclear Localization Signal (NLS) Sequence Modification

PEs have the remarkable ability to introduce a variety of different types of sequence alterations into the genome. PE editing efficiency is influenced by a variety of different parameters, including but not limited to: i) primer binding site (PBS) length; ii) position of the reverse transcription (RT) initiation site relative to the desired sequence alteration; iii) composition of the desired sequence alteration; or iv) relative position of an alternate strand nick. Even under optimal conditions, the incorporation rate of the desired edit into the genome is believed to be incomplete. Anzalone et al., "Search-and-replace genome editing without double-strand breaks or donor DNA" *Nature* 576:49-157 (2019).

It has been previously reported that modification of the composition and number of nuclear localization signal (NLS) sequences within a Cas9 effector can influence its efficiency of genome editing. Suzuki et al., "In vivo genome editing via CRISPR/Cas9 mediated homology independent targeted integration" *Nature* 540:144-149 (2016): Wu et al., "Highly efficient therapeutic gene editing of human hematopoietic stem cells" *Nat Med* 25:776-783 (2019); Koblan et al., "Improving cytidine and adenine base editors by expression optimization and ancestral reconstruction" Nat Biotechnol (2018); Zafra et al., "Optimized base editors enable efficient editing in cells, organoids and mice" *Nat Biotechnol* (2018); Song et al., "Adenine base editing in an adult mouse model of tyrosinaemia" *Nature Biomedical Engineering* 4:125-130 (2020); and Walton et al., "Unconstrained genome targeting with near-PAMless engineered CRISPR-Cas9 variants' Science (2020).

Figure 1A:
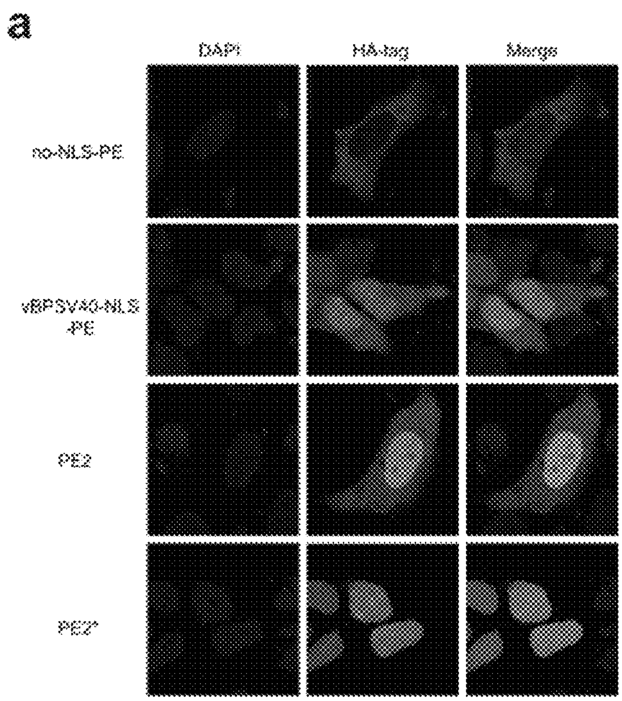
Figure 1B:
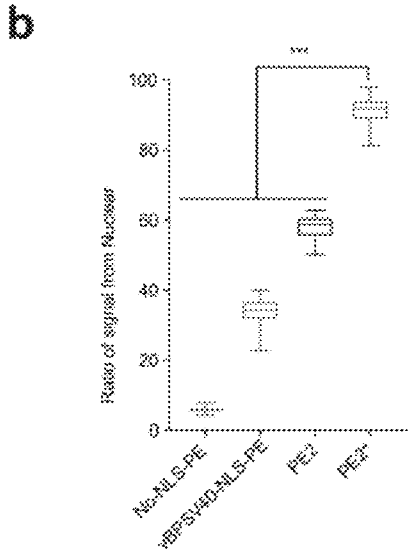

The original prime editor 2 (PE2) contained two bipartite SV40 NLS sequences. In transient transfection assays of original PE2, an incomplete nuclear localization was observed based on immunofluorescence: ~60% of the protein is present in the nucleus in U2OS cells and ~85% is present in the nucleus in HeLa cells. See, FIGS. 1A-D. However, with the addition of an N-terminal c-Myc NLS and modification of the C-terminus to contain a C-terminal variant bipartite SV40 NLS (vBP-SV40) as well as an SV40 NLS gave rise to a nearly complete nuclear localization of a presently disclosed prime editor (PE2*). FIGS. 1A, B, C & D. Ray et al., "Quantitative tracking of protein trafficking to the nucleus using cytosolic protein delivery by nanoparticle-stabilized nanocapsules" *Bioconjugate Chemistry* 26:1004-1007 (2015); and Makkerh et al., "Comparative mutagenesis of nuclear localization signals reveals the importance of neutral and acidic amino acids" *Curr Biol* 6:1025-1027 (1996). In one embodiment, the present invention contemplates a PE2* comprising an orthogonal *Staphylococcus aureus* nickase (SaCas9$^{N580A}$). SaCas9$^{N580A}$ repositions the single strand breakage of the conventional SpCas9$^{N580A}$ nickase. Ran et al., "In vivo genome editing using Staphylococcus aureus Cas9" *Nature* 520:186-191 (2015).

To expand the potential targeting range of these alternate prime editor systems, both the standard SaCas9 backbone and the SaCas9$^{KKH}$ variant were constructed. nSaCas9 PE2* recognizes an NNGRRT protospacer adjacent motif (PAM). Ran et al., "In vivo genome editing using Staphylococcus aureus Cas9" *Nature* 520:186-191 (2015). The SaCas9$^{KKH}$ variant (nSaCas9$^{KKH}$ PE2*) broadens the targeting to an NNNRRT PAM. See, FIG. 2A; and Kleinstiver et al., "Broadening the targeting range of Staphylococcus aureus CRISPR-Cas9 by modifying PAM recognition" *Nat Biotechnol* 33:1293-1298 (2015). SaCas9 PE2* or SaCas9$^{KKH}$ PE2* proteins were localized in the nucleus as observed by 3×HA-tag immunofluorescence staining. See, FIGS. 1C and 1D.

To determine whether the observed improvements in nuclear localization translate into increases in editing efficiency, the rate of nucleotide conversion for PE2 and PE2* was evaluated in HEK293T mCherry reporter cells that contains a premature TAG stop codon that prevents translation of a functional protein. See FIGS. 3A & 3D. PE2 and PE2* were programmed with a pegRNA designed to revert the TAG codon to CAG and delivered with and without different nicking sgRNAs. Three (3) days after transfection, flow cytometry was performed to quantify prime-editing efficiency. The results showed that PE2* produced a 1.5-1.6 fold increase in editing efficiency (14.3% to 26.4%) relative to PE2 (9.2% to 16.5%). See, FIG. 2B. Sa$^{KKH}$ PE2* also showed improved nucleotide conversion rates, but at a more modest editing efficiency than PE2* (e.g., 1.8% to 4.7%). All PE systems displayed lower editing activity than a conventional adenine base editor system (ABEmax)13 for restoration of reporter function. See, FIG. 2B and Koblan et al., "Improving cytidine and adenine base editors by expression optimization and ancestral reconstruction" *Nat Biotechnol* (2018).

The efficiency for generating a targeted deletion using PE2, PE2* and Sa$^{KKH}$ PE2* was determined in an HEK293T reporter line that can quantify both precise deletions and indel formation. This reporter design shares similarities to the traffic light reporter (TLR) system. Certo et al., "Tracking genome engineering outcome at individual DNA breakpoints" *Nature Methods* 8:671-676 (2011); and Mir et al., "Heavily and fully modified RNAs guide efficient SpyCas9-mediatedgenome editing" *Nat Commun* 9:2641 (2018). In TLR, a precise deletion of 47 bp removes a sequence insertion disrupting GFP expression, whereas indels that produce a particular reading frame alteration restore mCherry expression. See, FIGS. 3B & 3D. PE2* produced a 1.6-1.9 fold increase in the level of precise deletions (5.6%-11.3%) compared to PE2 (3.0%-7.3%). The relative level of undesired indel formation was roughly proportional to the overall activity levels for PE2 and PE2*. Also observed was that Sa$^{KKH}$PE2* could generate precise 47 bp deletion with efficiencies ranging from 1.3% to 4.2%. See, FIG. 2C.

The efficiency for generating a targeted insertion was determined using PE2, PE2* and $Sa^{KKH}$ PE2* in a TLR-MCV1 HEK293T reporter line that can quantify both precise insertions and indel formation. Iyer. et al., "Efficient Homology-directed Repair with Circular ssDNA Donors" *bioRxiv,* 786 864199 (2019). A targeted, precise replacement of 39 bp disruption sequence with a 18 bp missing sequence element restores GFP expression, whereas indels that produce a different reading frame alteration restore mCherry expression. See, FIGS. 3C & 3D. PE2* led to a 1.7 to 2.1-fold increase in the level of precise insertions (5.5%-11.6%) compared to PE2 (3.2%-5.5%. See, FIG. 2D. Again, the relative level of undesired indel formation was roughly proportional to the overall activity levels for PE2 and PE2*. Also observed was that $Sa^{KKH}$ PE2* could generate an 18 bp replacement with efficiencies ranging from 1.3% to 4.2%. See, FIG. 2D. Across all of these reporter systems, nicking the non-edited strand (PE3 format) increased the editing efficiency by 1.5- to 2.4-fold and the indel rate by 0.2% to 3.3% compared to pegRNA only in both PE2 and PE2*. See, FIGS. 2B, 2C & 2D. Together, these results demonstrate that PE2* performed nucleotide conversion, sequence deletion or insertion more efficiently than PE2. In addition, the presently disclosed SaCas9-based PE*s displayed appreciable genome editing activity.

B. PE2* Increases Editing Efficiency at Endogenous Loci

The editing efficiency of PE2 and PE2* were compared to previously described nucleotide substitutions, deletions and insertions at the EMX1 locus. Anzalone et al., "Search-and-replace genome editing without double-strand breaks or donor DNA" *Nature* 576:149-157 (2019). HEK293T cells were transfected with different prime editors, pegRNAs and different nicking sgRNAs. Genomic DNA was isolated and editing outcomes at each target site were quantified by high-throughput sequence (HTS).

PE2* (3.1%-6.5%) led to an average 1.9-fold increase in the rate of point mutation introduction compared to PE2 (1.5%-3.7%). Targeted 3 bp deletions were generated at 1.4 to 2.1-fold higher rate by PE2* (2.1%-6.0%) than PE2 (1.5%-2.9%). Targeted 6 bp insertions were generated at 1.7 to 2.4-fold higher rate by PE2* (2.2%-3.1%) than PE2 (0.9%-1.8%). See, FIG. 4A. As observed with the various reporter systems, the level of indel formation was roughly proportional to the activity levels of PE2 and PE2*. Together, these observations suggest that PE2* has broadly improved editing efficiency at endogenous loci.

The editing efficiency of Sa PE2* and $Sa^{KKH}$ PE2* was compared for the creation of similar nucleotide substitutions, deletions and insertions at the EMX1 locus. Notably, Sa PE2* installed point mutations at two positions in the EMX1 locus with editing efficiency from 4.7% to 9.3% and a modest indel rate (0.0%-0.5%). Targeted 3-bp deletion and 6-bp insertion were introduced by Sa PE2* with an editing efficiency of 4.1% to 9.4% and 2.7% to 5.5%, respectively. Indel induction generated by Sa PE2* ranged from 0.0% to 0.6%. See FIG. 4B. Overall, $Sa^{KKH}$ PE2* exhibited lower editing efficiency at the EMX1 locus than Sa PE2* with the same set of pegRNAs (typically between 1 and 2%). See, FIG. 4C. Notably, at these loci the editing efficiencies for Sa PE2* were similar to the rates obtained with PE2*, suggesting that the Sa PE2* platform broadens the scope of available prime editing systems.

C. Increased Correction Efficiency of Pathogenic Mutations In Vivo With Enhanced Prime Editors

1. Alpha-1 Antitrypsin Deficiency

Alpha-1 antitrypsin deficiency (AATD) is an inherited disorder that is believed to be caused by mutations in the Serpin Peptidase Inhibitor Family A member 1 (SERPINA1) gene. Loring et al., "Current status of gene therapy for alpha-1 antitrypsin deficiency" *Expert Opin Biol Ther* 15:329-336 (2015). For example, the E342K mutation (via G•C-to-A•T) in SERPINA1 (PiZ allele) is the most frequent mutation and causes severe lung and liver disease. Loring et al., "Current status of gene therapy for alpha-1 antitrypsin deficiency" *Expert Opin Biol Ther* 15:329-336 (2015). It has been reported that patients with homozygous mutation in SERPINA1 (PiZZ) have PiZ protein aggregates in hepatocytes and lack of functional AAT protein in the lung. The PiZ transgenic mouse contains sixteen (16) copies of the human SERPINA1 PiZ allele and is a commonly-used mouse model of human AATD. Carlson et al., "Accumulation of PiZ alpha 1-antitrypsin causes liver damage in transgenic mice' *J Clin Invest* 83:1183-1190 (1989).

Correction of the E342K mutation was unsuccessfully attempted using an adenine base editor because: i) there is no optimal NGG PAM is present nearby for SpCas9; and ii) other adenines are proximal to the target adenine that may also be susceptible to base conversion (e.g., the bystander effect). Gaudelli et al.," Programmable base editing of A*T to G*C in genomic DNA without DNA cleavage" *Nature* 551:464-471 (2017). In one embodiment, an NLS-prime editor system provides correction of mutations in genetic disorders due to an ability to rewrite a genomic sequence in non-dividing cells.

Patients with a homozygous mutation in SERP1NA1 (PiZZ) have PiZ protein aggregates in hepatocytes and lack of functional AAT protein in the lung. The PiZ transgenic mouse contains 16 copies of the human SERPINA1 PiZ allele and is a commonly-used mouse model of human AATD. Carlson et al., "Accumulation of PiZ alpha 1-antitrypsin causes liver damage in transgenic mice" *J Clin Invest* 83:1183-1190 (1989). For the correction of the E342K mutation, there are some challenges for the utilization of an adenine base editor: no optimal NGG PAM is present nearby for SpCas9, and in addition to the target adenine there are several other adenines that may also be susceptible to base conversion ("bystander effect"). Gaudelli et al., "Programmable base editing of A*T to G*C in genomic DNA without DNA cleavage" *Nature* 551:464-471 (2017).

Consequently, the utilization of a PE platform to correct this pathogenic mutation was investigated. To test the efficiency of different prime editors at this locus, the generation of the pathogenic E342K mutation (via G•C-to-A•T conversion) in wildtype SERPINA1 in HEK293T cells was evaluated. A series of different nicking sgRNAs were evaluated in conjunction with the PEs.

The data showed a 1.6 to 3.4-fold increase for G•C-to-A•T base transition in a serpina1 gene by PE2* (6.4%-15.8%) compared to PE2 (1.9%-9.9%). The average rate of indel generation with a nicking sgRNA slightly increased with PE2* (0.1%-3.8%) compared to PE2 (0.0%-2.2%). $Sa^{KKH}$PE2* exhibited lower overall editing efficiency for the installation of the E342K mutation (1.1%-4.4%). Indel generation at the target site by $Sa^{KKH}$PE2* ranged from 0.0% to 1.4%. See, FIG. 6A.

The ability of prime editors to directly correct a pathogenic mutation in vivo was also investigated. Based on editing results for SERPINA1 in HEK293T cells, a nicking sgRNA3 was used with the PEs. A pegRNA was designed to revert the E342K mutation. A PAM mutation (AGG→AAG) was also included to reduce re-cutting of the locus that introduced a synonymous codon change. See, FIG. 6B.

PE2 or PE2* with pegRNA and nicking sgRNA was introduced into PiZ mice liver (n=3/group) through a hydrodynamic tail vein injection. See, FIG. 6C. Hydrodynamic injection can deliver plasmid DNA to 20-30% of hepatocytes. Liu et al., "Hydrodynamics-based transfection 803 in animals by systemic administration of plasmid DNA" *Gene Ther* 6:1258-1266 (1999). Using a PE2 plasmid encoding an HA-tag, the data showed that 19.98±0.88% hepatocytes were HA-tag positive (n=4 mice). See, FIG. 7A. Forty-five (45) days after injection, livers of PiZ mice were collected and DNA was purified for HTS analysis. A 3.1-fold increase was observed for A•T-to-G•C correction in PiZ SERPINA1 by PE2* (6.7% on average) compared to PE2 (2.1%). The indel rate at the locus was also increased from 0.4% to 2.7%. See, FIG. 6D. Interestingly, this was accompanied by a low frequency of large deletions between pegRNA and nicking sgRNA. See, FIG. 7B. Together, these data demonstrate that prime editors can restore a wild type SERPINA1 allele thereby resulting in pathogenic gene correction in adult mice.

2. Acquired Immunodeficiency Syndrome

A homozygous 32-bp deletion in the CCR5 gene is believed to be associated with resistance to human immunodeficiency virus (HIV-1) infection. Dean et al., "Genetic restriction of HIV-1 infection and progression to AIDS by a deletion allele of the CKR5 structural gene Hemophilia Growth and Development Study, Multicenter AIDS Cohort Study, Multicenter Hemophilia Cohort Study, San Francisco City Cohort, ALIVE Study" *Science* 273:1856-1862 (1996); Liu et al., "Homozygous defect in HIV-1 coreceptor accounts for resistance of some multiply-exposed individuals to HIV-1 infection" Cell 86:367-377 (1996); and Samson et al., "Resistance to HIV-1 infection in Caucasian individuals bearing mutant alleles of the CCR-5 chemokine receptor gene" *Nature* 382:722-725 (1996).

The utility of PE2 and PE2* was evaluated to generate a large, therapeutically relevant 32-bp deletion within a ccr5 gene that recapitulates the HIV-1 resistance allele. See, FIG. 4D.

Linear amplification was used to incorporate unique molecular identifiers (UMI) prior to sequencing to avoid PCR amplification bias for the assessment of the deletion rate in the population of treated cells. Bolukbasi et al., "Orthogonal Cas9-Cas9 chimeras provide a versatile platform for genome editing" *Nat Commun* 9:4856 (2018). Both PE2 and PE2* were able to generate a 32-bp deletion within the ccr5 locus in HeLa cells, where the PE2* editor displayed higher deletion rates than PE2 (an average increase of 1.4-fold across all conditions) with a maximum efficiency of about 6.0%. $Sa^{KKH}$PE2* exhibited a lower editing efficiency than PE2 for the generation of the 32-bp deletion, with a maximum efficiency of 2.9%. See, FIG. 4E & FIG. 5. Overall, these results demonstrate that PE's can introduce a therapeutically relevant deletion in a CCR5 gene in human cells.

3. Cystic Fibrosis

There are some common mutant alleles that result in the expression of Cystic fibrosis (CF) that can be corrected by the insertion of a modified sequence. In one embodiment, the present invention contemplates the insertion of a CTCF delF508 sequence to convert a CF-mutated genome into a wild type genome.

D. Creation of Animal Genetic Disease Models With Prime Editors

Ctnnb1 (β-catenin) is a commonly mutated gene in hepatocellular carcinoma. Zucman-Rossi et al., Genetic landscape and biomarkers of hepatocellular carcinoma" *Gastroenterology* 149:1226-1239 (2015). Overexpression of a mutant Ctnnb1 and Myc oncogene have been used to generate liver cancer models. Zafraet al., "Optimized base editors enable efficient editing in cells, organoids and mic" *Nat Biotechnol* (2018).

The potential for prime editors to drive tumor formation in vivo was assessed by the delivery of PE2 or PE2* with a pegRNA (C•G-to-T•A) and a nicking sgRNA in adult FVB mice livers (n=4/group) to install an oncogenic S45F mutation in Ctnnb1. See, FIGS. 8A and 8B. A Myc transposon and transposase were co-injected to provide a second oncogenic driver necessary for tumor formation in conjunction with the Ctnnb1 mutation. Liu et al., "A functional mammalian target of rapamycin complex 1 signaling is indispensable for c-Myc-driven hepatocarcinogenesis" *Hepatology* 66:167-181 (2017).

Twenty five (25) days after injection, livers of adult mice were collected and tumor nodules on the liver were quantified. PE2-treated animals showed an average 5.5±1.1 tumors per mouse, whereas PE2*-treated mice displayed higher rates of tumor formation, with an average 10.0±2.7 tumors on the liver. See, FIGS. 8C and 8D. Consistent with gain of function of the S45F mutation, liver tumors were positive for nuclear β-Catenin. See, FIG. 9. Sanger sequence of gDNA from the tumor nodules showed precise conversion of S45F in Ctnnb1. See, FIG. 8E. Prime editors, therefore, afford the opportunity to install other types of mutations within the genome to create animal models for any type of genetic disease.

To assess the feasibility of generating deletions in vivo, a pegRNA was designed to delete the S45 codon in Ctnnb1, which is a previously described oncogenic mutation at this locus. Marquardt et al., "Functional and genetic deconstruction of the cellular origin in liver cancer" *Nat Rev Cancer* 15:653-667 (2015); See FIG. 8F. The prime editor (PE2*), pegRNA for Ctnnb1 S45 deletion and nicking sgRNA plasmids were delivered by hydrodynamic tail-vein injection along with the MYC transposon and transposase plasmids. pegRNA Ctnnb1 S45 codon deletion-treated animals showed extensive tumor formation, whereas pegRNA SERPINA1-treated animals did not induce any tumor formation. See, FIG. 8G. Deep sequencing showed that more than 80% of tumor gDNA contained precise editing removing the S45 codon. See, FIG. 8H. Together, these results demonstrate that prime editors can be used for generating genetic disease models (e.g., tumor models) by somatic cell engineering in vivo, and that PE2* provides a platform with improved editing activity.

III. Split-Intein Prime Editor Associated Adenovirus Delivery

In one embodiment, the present invention contemplates a dual-associated adenovirus (AAV) comprising a split-intein prime editor. Although it is not necessary to understand the mechanism of an invention, it is believed that the split-intein prime editor AAV produces precise editing in vivo following a single administration. While the data presented herein exemplifies liver genome editing, dual AAV mediated prime editors as contemplated herein are equally applicable to other organ systems.

In one embodiment, successful editing efficiency with the dual AAV system disclosed herein was observed with an administered vector dose of $2\times10^{11}$ vg/kg total. In one embodiment, the dual AAV system comprises an original PE2 architecture. Although it is not necessary to understand the mechanism of an invention, it is believed that PE2 is sufficiently compact size for efficient vector packaging. In one embodiment, PE2* comprises substitutions of conventional SV40 NLSs with a bipartite SV40 NLS or a c-myc NLS. In one embodiment, the dual AAV system comprises an Sa PE2* or an $Sa^{KKH}$ PE2*.

The ~6.3-kb coding sequence of most PEs exceed the ~4.8-kb packaging size limit of AAV. Wang et al., "Adeno-associated virus vector as a platform for gene therapy delivery". To deliver prime editors with AAVs, a split Cas9 dual-AAV was created in which the original PE2 prime editor is divided into an amino-terminal (PE2-N) and carboxy-terminal (PE2-C) segments, which are then reconstituted to full length PE by a trans-splicing intein. Levy et al., "Cytosine and adenine base editing of the brain, liver, retina, heart and skeletal muscle of mice via adeno-associated viruses" *Nat Biomed Eng* 4:97-110 (2020); and Zettler et al., "The naturally split Npu DnaE intein exhibits an extraordinarily high rate in the protein trans-splicing reaction". *FEBS Lett* 583:909-914 (2009); See, FIG. 10A.

To ensure that each prime editor segment is smaller than the AAV packaging size limit, the PE was divided within the SpCas9 amino acid before Ser 714. Wright et al., "Rational design of a split-Cas9 enzyme complex" Proc Natl Acad Sci U S A 112:2984-2989 (2015). AAV8 particles were generated by encoding a split-intein PE, a nicking sgRNA and a pegRNA to correct the E342K mutation in SERPINAL See, FIG. 10A. The performance of the split-intein AAV prime editor was the characterized in vivo.

PiZ mice were treated by tail-vein injection of a low dose dual AAV8-PE ($2\times10^{11}$ viral genome total (vg)). See, FIG. 10B. Livers were harvested at 2 weeks (n=2), 6 weeks (n=3) and 10 weeks (n=3) after injection. Targeted deep sequencing detected 0.6±0.0% precise editing at 2 weeks. The precise editing efficiency increased significantly to 2.3±0.4% at 6 weeks and 3.1±0.6% at 10 weeks. See, FIG. 10C. A corresponding increase of indel rates were observed at the target site by split intein AAVs from 0.1±0.0% (2 weeks) to 0.4±0.1% (10 weeks). Utilization of the UdiTaS unidirectional sequencing approach with locus specific primers for library construction affords the opportunity to assess the rate of large deletions or other types of genomic rearrangements in an unbiased manner. Giannoukos et al., "UDiTaS™, a genome editing detection method for indels and genome rearrangements" BMC Genomics 19:212 (2018).

UDiTaS analysis at the SERPINA1 transgene locus revealed primarily precise editing among the modified alleles. As observed by the amplicon deep sequencing, a fraction of the modified alleles contained indels and there were a small number of larger deletions between the two nicking sites or extending beyond these sites, although many of the largest deletions (>100 bp) did not meet the level of statistical significance. See, FIGS. 10D & 10E, FIGS. 11A-B. There was also evidence of a very low rate of AAV insertion at the target site (0.014% of total UMIs). Together, these results demonstrate that delivery of split intein PE by the dual AAV8 enables low rates of precise editing via the PE3 prime editing strategy in vivo.

EXPERIMENTAL

Example I

Generation of Plasmids

To generate pegRNA expression plasmids, PCR products including spacer sequences, scaffold sequences and 3' extension sequences were amplified using Phusion master mix (ThermoFisher Scientifc) or Q5 High-Fidelity enzyme (NewEnglandBioLabs), which were subsequently cloned into a custom vector (BfuA/EcoR I digested)(Gibson, NEB). To generate nicking sgRNA expression plasmids, annealed oligos were cloned into BfuAI-372 digested vector or pmd264 vector. Table 1.

TABLE 1

Sequences of pegRNAs and sgRNAs used in this study. All sequences are shown in 5' to 3' orientation.

SpCas9 pegRNA scaffold [constant region]:
GTTTTAGAGCTAGAAATAGCAAGTTAAAATAAGGCTAGTCCGTTATCAACTTGAAAAAGTGGGACCGAGTCGGTCC
(SEQ ID NO: 9)

SaCas9 pegRNA scaffold [constant region]:
GTTTTAGTACTCTGGAAACAGAATCTACTAAAACAAGGCAAAATGCCGTGTTTATCTCGTCAACTTGTTGGCGAGA
(SEQ ID NO: 10)

| pegRNA | SEQ ID NO: | spacer sequence (5'-3') | SEQ ID NO: | 3' extension | PBS (nt) | RT (nt) | FIG. | PE |
|---|---|---|---|---|---|---|---|---|
| mCherry A to G | 11 | CACCTTCAGCTTGGCGGTCT | 12 | TACGAGGGCACTCAAACCGCCAAGCTGAAG | 14 | 16 | FIG. 2B | PE2 or PE2* |
| mCherry A to G | 13 | GGTCACCTTCAGCTTGGCGGT | 14 | TACGAGGGCACCCAGACTGCCAAGCTGAAGGTGA | 16 | 17 | FIG. 2B | $Sa^{KKH}$PE2* |
| GFP-insertion | 15 | AAGTTCAGCGTGTCCGGCTT | 16 | GTCAGCTTGCCGTAGGTGGCATCGCCCTCGCCTTCG | 13 | 36 | FIG. 2C | PE2 or PE2* |

TABLE 1-continued

Sequences of pegRNAs and sgRNAs used in this study.
All sequences are shown in 5' to 3' orientation.

| | | | | | | | | |
|---|---|---|---|---|---|---|---|---|
| GFP-insertion | 17 | TGAACTTCAGGGTCAGCTTGCC | 18 | ACAAGTTCAGCGTGTCCGGCGAGGGCGAGGGCGATGCCACGTACGGCAAGCTGACCCTGAAGTTC | 18 | 47 | FIG. 2C | Sa$^{KKH}$PE2* |
| GFP-deletion | 19 | GCGGAGAGGGCACCCCCGA | 20 | GTTGGTCATGCGACCCTGCTCGGGGGTGCCCTCTCC | 14 | 22 | FIG. 2D | PE2 or PE2 |
| GFP-deletion | 21 | GGTCATGCGACCCTGCTCGGA | 22 | CGGAGAGGGCACCCCCGAGCAGGGTCGCATG | 15 | 16 | FIG. 2D | Sa$^{KKH}$PE2* |
| EMX1 +5 G to T | 23 | GAGTCCGAGCAGAAGAAGAA | 24 | ATGGGAGCACTTCTTCTTCTGCTC | 14 | 10 | FIG. 4A | PE2 or PE2* |
| EMX1 +3 +8 G to T | 25 | CAGAAGCTGGAGGAGGAAGGGC | 26 | TGCTCGGAATCAGACCCTTCCTCCTCCAGCT | 15 | 16 | FIG. 4A | SaCas9 PE2* or Sa$^{KKH}$PE2* |
| EMX1 +4 3 bp deletion | 27 | GAGTCCGAGCAGAAGAAGAA | 28 | ATGTGATGGGAGTTCTTCTTCTGCTC | 14 | 12 | FIG. 4B | PE2 or PE2* |
| EMX1 +1 3 bp deletion | 29 | CAGAAGCTGGAGGAGGAAGGGC | 30 | TTCTGCTCGGACTCAGCTTCCTCCTCCAGCT | 15 | 16 | FIG. 4B | SaCas9 PE2* or Sa$^{KKH}$PE2* |
| EMX1 +4 6 bp Insertion | 31 | GAGTCCGAGCAGAAGAAGAA | 32 | GAGCAGAAGAAGAAAAGCTTGGGCTCCCATCACAT | 14 | 21 | FIG. 4C | PE2 or PE2* |
| EMX1 +1 6 bp Insertion | 33 | CAGAAGCTGGAGGAGGAAGGGC | 34 | TGCTCGGACTCAGGCCAAGCTTCTTCCTCCTCCAGCT | 15 | 22 | FIG. 4C | SaCas9 PE2* or Sa$^{KKH}$PE2* |
| CCR5-delta32-deletion | 35 | AGATGACTATCTTTAATGTC | 36 | ATTACACCTGCAGCTCTCATTTTCCTTATATTAAAGATAGTCATC | 16 | 29 | FIG. 4D | PE2 or PE2* |
| CCR5-delta32-deletion | 37 | AAGATGACTATCTTTAATGTCT | 38 | AGCTCTCATTTTCCATACATTAAAGATAGTCATC | 17 | 17 | FIG. 4D | Sa$^{KKH}$PE2* |
| Serpina1 G to A | 39 | TCCCCTCCAGGCCGTGCATA | 40 | TCTTGTCGATGGTCAGCACAGCTTTATGCACGGCCTGGAG | 13 | 27 | FIG. 6A | PE2 or PE2* |
| Serpina1 G to A | 41 | CAGCTTCAGTCCCTTTCTCGT | 42 | ATCGACAAGAAAGGGACTGAAGCT | 15 | 9 | FIG. 6A | Sa$^{KKH}$PE2* |
| Serpina1 A to G | 43 | TCCCCTCCAGGCCGTGCATA | 44 | TCTCGTCGATGGTCAGCACAGCTTTATGCACGGCCTGGAG | 13 | 27 | FIG. 6B | PE2 or PE2* |
| Ctnnb1 C to T | 45 | AGGGTTGCCCTTGCCACTCA | 46 | GCTCCTTTCCTGAGTGGCAAGGGCAA | 13 | 13 | FIG. 8A | PE2 or PE2* |
| Ctnnb1 C to T | 47 | AGGGTTGCCCTTGCCACTCA | 48 | ACAGCTCCTTTGAGTGGCAAGGGCAA | 13 | 13 | FIG. 8D | PE2* |

TABLE 1-continued

Sequences of pegRNAs and sgRNAs used in this study.
All sequences are shown in 5' to 3' orientation.

| Nicking sgRNA | SEQ ID NO: | spacer sequence (5'-3') | FIG. | PE |
|---|---|---|---|---|
| mCherry A to G | 49 | GCGCTTCAAGGTGCACATGGA | FIG. 2B | PE2 or PE2* |
| mCherry A to G | 50 | GCTGTCCCCTCAGTTCATGTA | FIG. 2B | PE2 or PE2 |
| mCherry A to G | 51 | GATGGAGGGCTCCGTGAACGGCC | FIG. 2B | Sa$^{KKH}$PE2* |
| mCherry A to G | 52 | GTTCGCCTGGGACATCCTGTCCC | FIG. 2B | Sa$^{KKH}$PE2* |
| GFP-insertion-sp-NK1 | 53 | GTAGGTCAGGGTGGTCACGA | FIG. 2C | PE2 or PE2* |
| GFP-insertion-sp-NK2 | 54 | GCTCCTCGCCCTTGCTCACCA | FIG. 2C | PE2 or PE2* |
| GFP-insertion-saKKH-NK1 | 55 | GCAAGGGCGAGGAGCTGTTCAC | FIG. 2C | Sa$^{KKH}$PE2* |
| GFP-insertion-saKKH-NK2 | 56 | GTGACCACCCTGACCTACGGCG | FIG. 2C | Sa$^{KKH}$PE2* |
| GFP-deletion-sp-NK1 | 57 | GAGAAGCCGTAGCCCATCACG | FIG. 2D | PE2 or PE2* |
| GFP-deletion-sp-NK2 | 58 | GATCTTCATGGCGGGCATGG | FIG. 2D | PE2 or PE2* |
| GFP-deletion-saKKH-NK1 | 59 | GATCACCGGCACCCTGAACGGCG | FIG. 2D | Sa$^{KKH}$PE2* |
| GFP-deletion-saKKH-NK2 | 60 | GCAGCCCCTACCTGCTGAGCCA | FIG. 2D | Sa$^{KKH}$PE2* |
| EMX1 +5 G to T-sp-NK1 | 61 | GTTGCCCACCCTAGTCATTGG | FIG. 4A | PE2 or PE2* |
| EMX1 +5 G to T-sp-NK2 | 62 | GGCCGTTTGTACTTTGTCCTC | FIG. 4A | PE2 or PE2* |
| EMX1 +3 +8 G to T-sa-NK1 | 63 | GCCTGGGCCAGGGAGGGAGGGGC | FIG. 4A | SaCas9 PE2* or Sa$^{KKH}$PE2* |
| EMX1 +3 +8 G to T-sa-NK2 | 64 | GTGGTTGCCCACCCTAGTCATT | FIG. 4A | SaCas9 PE2* or Sa$^{KKH}$PE2* |
| EMX1 +4 3bp deletion-sp-NK1 | 65 | GTTGCCCACCCTAGTCATTGG | FIG. 4B | PE2 or PE2* |
| EMX1 +4 3bp deletion-sp-NK2 | 66 | GGCCGTTTGTACTTTGTCCTC | FIG. 4B | PE2 or PE2* |
| EMX1 +1 3bp deletion-sa-NK1 | 67 | GCCTGGGCCAGGGAGGGAGGGGC | FIG. 4B | SaCas9 PE2* or Sa$^{KKH}$PE2* |
| EMX1 +1 3bp deletion-sa-NK2 | 68 | GTGGTTGCCCACCCTAGTCATT | FIG. 4B | SaCas9 PE2* or Sa$^{KKH}$PE2* |

TABLE 1-continued

Sequences of pegRNAs and sgRNAs used in this study. All sequences are shown in 5' to 3' orientation.

| | | | | |
|---|---|---|---|---|
| EMX1 +4 6bp Insertion-sp-NK1 | 69 | GTTGCCCACCCTAGTCATTGG | FIG. 4C | PE2 or PE2* |
| EMX1 +4 6bp Insertion-sp-NK2 | 70 | GGCCGTTTGTACTTTGTCCTC | FIG. 4C | PE2 or PE2* |
| EMX1 +1 6bp Insertion-sa-NK1 | 71 | GCCTGGGCCAGGGAGGGAGGGGC | FIG. 4C | SaCas9 PE2* or $Sa^{KKH}$PE2* |
| EMX1 +1 6bp Insertion-sa-NK2 | 72 | GTGGTTGCCCACCCTAGTCATT | FIG. 4C | SaCas9 PE2* or $Sa^{KKH}$PE2* |
| CCR5-deletion-sp-NK1 | 73 | GCTGTGTTTGCGTCTCTCCC | FIG. 4E | PE2 or PE2* |
| CCR5-deletion-sp-NK2 | 74 | GACAAGTGTGATCACTTGGG | FIG. 4E | PE2 or PE2* |
| CCR5-deletion-sp-NK3 | 75 | GCAGGACGGTCACCTTTGGGG | FIG. 4E | PE2 or PE2* |
| CCR5-deletion-saKKH-NK1 | 76 | GCATCTTTACCAGATCTCAAAAA | FIG. 4E | $Sa^{KKH}$PE2* |
| CCR5-deletion-saKKH-NK2 | 77 | GTGGCTGTGTTTGCGTCTCTCCC | FIG. 4E | $Sa^{KKH}$PE2* |
| Serpina1 G to A-sp-NK1 | 78 | GGGGGGGATAGACATGGGTA | FIG. 6A | PE2 or PE2* |
| Serpina1 G to A-sp-NK2 | 79 | GACCTCGGGGGGGATAGACA | FIG. 6A | PE2 or PE2* |
| Serpina1 G to A-sp-NK3 | 80 | GGGTTTGTTGAACTTGACCT | FIG. 6A | PE2 or PE2* |
| Serpina1 G to A-sp-NK4 | 81 | GTTCAATCATTAAGAAGACAA | FIG. 6A | PE2 or PE2* |
| Serpina1 G to A | 82 | GCACGTGAGCCTTGCTCGAGGCC | FIG. 6A | $Sa^{KKH}$PE2* |
| Serpina1 G to A | 83 | GCCCATGTCTATCCCCCCCGAGG | FIG. 6A | $Sa^{KKH}$PE2* |
| Serpina1 A to G (mouse_ injection) | 84 | GGGTTTGTTGAACTTGACCT | FIG. 6B | PE2 or PE2* |
| Ctnnb1 C to T | 85 | GGAAAAGCTGCTGTCAGCCAC | FIG. 8A | PE2 or PE2 |

PE2* was generated through Gibson assembly, by combining SpyCas9(H840A) and the M-MLV RT from PE2 with additional NLS sequences and insertion into a NotI/PmeI-digested pCMV-PE2 backbone. SEQ ID NO: 1

A SpCas9-PE2* prime editor (SEQ ID NO: 1)

PE2*: Cmyc_NLS-BPSV40_NLS-SpCas9H840A-linker-M-MLV_reverse_transcriptase-vBPSV40_NLS-SV40

PAAKRVKLDGGKRTADGSEFESPKKKRKVDKKYSIGLDIGTNSVGWAVITDEYKVPSKKFKVLG
NTDRHSIKKNLIGALLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKADLRLIYLALAHMIKF
RGHFLIEGDLNPDNSDVDKLFIQLVQTYNQLFEENPINASGVDAKAILSARLSKSRRLENLIAQ

TABLE 1-continued

Sequences of pegRNAs and sgRNAs used in this study.
All sequences are shown in 5' to 3' orientation.

LPGEKKNGLFGNLIALSLGLTPNFKSNFDLAEDAKLQLSKDTYDDDLDNLLAQIGDQYADLFLA
AKNLSDAILLSDILRVNTEITKAPLSASMIKRYDEHHQDLTLLKALVRQQLPEKYKEIFFDQSK
NGYAGYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEEVVDK
GASAQSFIERMTNFDKNLPNEKVLPKHSLLYEYFTVYNELTKVKYVTEGMRKPAFLSGEQKKAI
VDLLFKTNRKVTVKQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLSRKLINGIRDKQSG
KTILDFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPVENT
QLQNEKLYLYYLQNGRDMYVDQELDINRLSDYDVDAIVPQSFLKDDSIDNKVLTRSDKNRGKSD
NVPSEEVVKKMKNYWRQLLNAKLITQRKFDNLTKAERGGLSELDKAGFIKRQLVETRQITKHVA
QILDSRMNTKYDENDKLIREVKVITLKSKLVSDFRKDFQFYKVREINNYHHAHDAYLNAVVGTA
LIKKYPKLESEFVYGDYKVYDVRKMIAKSEQEIGKATAKYFFYSNIMNFFKTEITLANGEIRKR
PLIETNGETGEIVWDKGRDFATVRKVLSMPQVNIVKKTEVQTGGFSKESILPKRNSDKLIARKK
DWDPKKYGGFDSPTVAYSVLVVAKVEKGKSKKLKSVKELLGITIMERSSFEKNPIDFLEAKGYK
EVKKDLIIKLPKYSLFELENGRKRMLASAGELQKGNELALPSKYVNFLYLASHYEKLKGSPEDN
EQKQLFVEQHKHYLDEIIEQISEFSKRVILADANLDKVLSAYNKHRDKPIREQAENIIHLFTLT
NLGAPAAFKYFDTTIDRKRYTSTKEVLDATLIHQSITGLYETRIDLSQLGGDSGGSSGGSSGSE
TPGTSESATPESSGGSSGGSSTLNIEDEYRLHETSKEPDVSLGSTWLSDFPQAWAETGGMGLAV
RQAPLIIPLKATSTPVSIKQYPMSQEARLGIKPHIQRLLDQGILVPCQSPWNTPLLPVKKPGTN
DYRPVQDLREVNKRVEDIHPTVPNPYNLLSGLPPSHQWYTVLDLKDAFFCLRLHPTSQPLFAFE
WRDPEMGISGQLTWTRLPQGFKNSPTLFNEALHRDLADFRIQHPDLILLQYVDDLLLAATSELD
CQQGTRALLQTLGNLGYRASAKKAQICQKQVKYLGYLLKEGQRWLTEARKETVMGQPTPKTPRQ
LREFLGKAGFCRLFIPGFAEMAAPLYPLTKPGTLFNWGPDQQKAYQEIKQALLTAPALGLPDLT
KPFELFVDEKQGYAKGVLTQKLGPWRRPVAYLSKKLDPVAAGWPPCLRMVAAIAVLTKDAGKLT
MGQPLVILAPHAVEALVKQPPDRWLSNARMTHYQALLLDTDRVQFGPVVALNPATLLPLPEEGL
QHNCLDILAEAHGTRPDLTDQPLPDADHTWYTDGSSLLQEGQRKAGAAVTTETEVIWAKALPAG
TSAQRAELIALTQALKMAEGKKLNVYTDSRYAFATAHIHGEIYRRRGWLTSEGKEIKNKDEILA
LLKALFLPKRLSIIHCPGHQKGHSAEARGNRMADQAARKAAITETPDTSTLLIENSSPSGGSKR
TADGSEKRTADSQHSTPPKTKRKVEFEPKKKRKV

SaPE2* and SaKKHPE2* were generated through Gibson assembly,
by combining the following three DNA fragments:
(i) PCR amplified M-MLV RT with additional NLS sequences from PE2,
(ii) a NotI/PmeI-digested PE2 backbone,
(iii) a SaCas9 N580A nickase or a $Sa^{KKH}$– Cas9 nickase.
SEQ ID NO: 2 & SEQ ID NO: 3.
A SaCas9-PE2* prime editor (SEQ ID NO: 2)
SaPE2*: Cmyc_NLS-BPSV40_NLS-SaCas9N580A-linker-M-
MLV_reverse_transcriptase-vBPSV40_NLS-SV40
PAAKRVKLDGGKRTADGSEFESPKKKRKVGIHGVPAAKRNYILGLDIGITSVGYGIIDYETRDV
IDAGVRLFKEANVENNEGRRSKRGARRLKRRRRHRIQRVKKLLFDYNLLTDHSELSGINPYEAR
VKGLSQKLSEEEFSAALLHLAKRRGVHNVNEVEEDTGNELSTKEQISRNSKALEEKYVAELQLE
RLKKDGEVRGSINRFKTSDYVKEAKQLLKVQKAYHQLDQSFIDTYIDLLETRRTYYEGPGEGSP
FGWKDIKEWYEMLMGHCTYFPEELRSVKYAYNADLYNALNDLNNLVITRDENEKLEYYEKFQII
DQIAKILTIYQSSEDIQEELTNLNSELTQEEIEQISNLKGYTGTHNLSLKAINLILDELWHTND
NQIAIFNRLKLVPKKVDLSQQKEIPTTLVDDFILSPVVKRSFIQSIKVINAIIKKYGLPNDIII
ELAREKNSKDAQKMINEMQKRNRQTNERIEEIIRTTGKENAKYLIEKIKLHDMQEGKCLYSLEA
IPLEDLLNNPFNYEVDHIIPRSVSFDNSFNNKVLVKQEEASKKGNRTPFQYLSSSDSKISYETF
KKHILNLAKGKGRISKTKKEYLLEERDINRFSVQKDFINRNLVDTRYATRGLMNLLRSYFRVNN
LDVKVKSINGGFTSFLRRKWKFKKERNKGYKHHAEDALIIANADFIFKEWKKLDKAKKVMENQM
FEEKQAESMPEIETEQEYKEIFITPHQIKHIKDFKDYKYSHRVDKKPNRELINDTLYSTRKDDK
GNTLIVNNLNGLYDKDNDKLKKLINKSPEKLLMYHHDPQTYQKLKLIMEQYGDEKNPLYKYYEE
TGNYLTKYSKKDNGPVIKKIKYYGNKLNAHLDITDDYPNSRNKVVKLSLKPYRFDVYLDNGVYK
FVTVKNLDVIKKENYYEVNSKCYEEAKKLKKISNQAEFIASFYNNDLIKINGELYRVIGVNNDL
LNRIEVNMIDITYREYLENMNDKRPPRIIKTIASKTQSIKKYSTDILGNLYEVKSKKHPQIIKK
GSGGSSGGSSGSETPGTSESATPESSGGSSGGSSTLNIEDEYRLHETSKEPDVSLGSTWLSDFP
QAWAETGGMGLAVRQAPLIIPLKATSTPVSIKQYPMSQEARLGIKPHIQRLLDQGILVPCQSPW
NTPLLPVKKPGTNDYRPVQDLREVNKRVEDIHPTVPNPYNLLSGLPPSHQWYTVLDLKDAFFCL
RLHPTSQPLFAFEWRDPEMGISGQLTWTRLPQGFKNSPTLFNEALHRDLADFRIQHPDLILLQY
VDDLLLAATSELDCQQGTRALLQTLGNLGYRASAKKAQICQKQVKYLGYLLKEGQRWLTEARKE
TVMGQPTPKTPRQLREFLGKAGFCRLFIPGFAEMAAPLYPLTKPGTLFNWGPDQQKAYQEIKQA
LLTAPALGLPDLTKPFELFVDEKQGYAKGVLTQKLGPWRRPVAYLSKKLDPVAAGWPPCLRMVA
AIAVLTKDAGKLTMGQPLVILAPHAVEALVKQPPDRWLSNARMTHYQALLLDTDRVQFGPVVAL
NPATLLPLPEEGLQHNCLDILAEAHGTRPDLTDQPLPDADHTWYTDGSSLLQEGQRKAGAAVTT
ETEVIWAKALPAGTSAQRAELIALTQALKMAEGKKLNVYTDSRYAFATAHIHGEIYRRRGWLTS
EGKEIKNKDEILALLKALFLPKRLSIIHCPGHQKGHSAEARGNRMADQAARKAAITETPDTSTL
LIENSSPSGGSKRTADGSEKRTADSQHSTPPKTKRKVEFEPKKKRKV A $Sa^{KKH}$Cas9-PE2* prime editor (SEQ ID NO: 3)
$Sa^{KKH}$PE*: Cmyc_NLS-BPSV40_NLS-$SaCas9^{KKH}$N580A-linker-M-
MLV_reverse_transcriptase-vBPSV40_NLS-SV40
PAAKRVKLDGGKRTADGSEFESPKKKRKVGIHGVPAAKRNYILGLDIGITSVGYGIIDYETRDV
IDAGVRLFKEANVENNEGRRSKRGARRLKRRRRHRIQRVKKLLFDYNLLTDHSELSGINPYEAR
VKGLSQKLSEEEFSAALLHLAKRRGVHNVNEVEEDTGNELSTKEQISRNSKALEEKYVAELQLE
FGWKDIKEWYEMLMGHCTYFPEELRSVKYAYNADLYNALNDLNNLVITRDENEKLEYYEKFQII
ENVFKQKKKPTLKQIAKEILVNEEDIKGYRVTSTGKPEFTNLKVYHDIKDITARKEIIENAELL TABLE 1-continued

| Sequences of pegRNAs and sgRNAs used in this study. All sequences are shown in 5' to 3' orientation. |
|---|
| DQIAKILTIYQSSEDIQEELTNLNSELTQEEIEQISNLKGYTGTHNLSLKAINLILDELWHTND<br>NQIAIFNRLKLVPKKVDLSQQKEIPTTLVDDFILSPVVKRSFIQSIKVINAIIKKYGLPNDIII<br>ELAREKNSKDAQKMINEMQKRNRQTNERIEEIIRTTGKENAKYLIEKIKLHDMQEGKCLYSLEA<br>IPLEDLLNNPFNYEVDHIIPRSVSFDNSFNNKVLVKQEEASKKGNRTPFQYLSSSDSKISYETF<br>KKHILNLAKGKGRISKTKKEYLLEERDINRFSVQKDFINRNLVDTRYATRGLMNLLRSYFRVNN<br>LDVKVKSINGGFTSFLRRKWKFKKERNKGYKHHAEDALIIANADFIFKEWKKLDKAKKVMENQM<br>FEEKQAESMPEIETEQEYKEIFITPHQIKHIKDFKDYKYSHRVDKKPNRKLINDTLYSTRKDDK<br>GNTLIVNNLNGLYDKDNDKLKKLINKSPEKLLMYHHDPQTYQKLKLIMEQYGDEKNPLYKYYEE<br>TGNYLTKYSKKDNGPVIKKIKYYGNKLNAHLDITDDYPNSRNKVVKLSLKPYRFDVYLDNGVYK<br>FVTVKNLDVIKKENYYEVNSKCYEEAKKLKKISNQAEFIASFYKNDLIKINGELYRVIGVNNDL<br>LNRIEVNMIDITYREYLENMNDKRPPHIIKTIASKTQSIKKYSTDILGNLYEVKSKKHPQIIKK<br>GSGGSSGGSSGSETPGTSESATPESSGGSSGGSSTLNIEDEYRLHETSKEPDVSLGSTWLSDFP<br>QAWAETGGMGLAVRQAPLIIPLKATSTPVSIKQYPMSQEARLGIKPHIQRLLDQGILVPCQSPW<br>NTPLLPVKKPGTNDYRPVQDLREVNKRVEDIHPTVPNPYNLLSGLPPSHQWYTVLDLKDAFFCL<br>RLHPTSQPLFAFEWRDPEMGISGQLTWTRLPQGFKNSPTLFNEALHRDLADFRIQHPDLILLQY<br>VDDLLLAATSELDCQQGTRALLQTLGNLGYRASAKKAQICQKQVKYLGYLLKEGQRWLTEARKE<br>TVMGQPTPKTPRQLREFLGKAGFCRLFIPGFAEMAAPLYPLTKPGTLFNWGPDQQKAYQEIKQA<br>LLTAPALGLPDLTKPFELFVDEKQGYAKGVLTQKLGPWRRPVAYLSKKLDPVAAGWPPCLRMVA<br>AIAVLTKDAGKLTMGQPLVILAPHAVEALVKQPPDRWLSNARMTHYQALLLDTDRVQFGPVVAL<br>NPATLLPLPEEGLQHNCLDILAEAHGTRPDLTDQPLPDADHTWYTDGSSLLQEGQRKAGAAVTT<br>ETEVIWAKALPAGTSAQRAELIALTQALKMAEGKKLNVYTDSRYAFATAHIHGEIYRRRGWLTS<br>EGKEIKNKDEILALLKALFLPKRLSIIHCPGHQKGHSAEARGNRMADQAARKAAITETPDTSTL<br>LIENSSPSGGSKRTADGSEKRTADSQHSTPPKTKRKVEFEPKKKRKV |

All plasmids used for in vitro experiments were purified including an endotoxin removal step (Miniprep®, Qiagen). pCMV-PE2 was a gift from David Liu (Addgene plasmid #132775).

AAV-PE-N was generated through Gibson assembly, by combining the following five DNA fragments: (i) gBlock pegRNA driven by U6, (ii) gBlock nicking sgRNA driven by U6, (iii) PCR amplified N-terminal PE2 (amino acid 1-713 of SpCas9 H840A), (iv) gBlock split-intein N terminal, (v) a KpnI/SacI-digested AAV backbone. Yin et al., "Therapeutic genome editing by combined viral and non-viral delivery of CRISPR system components in vivo" *Nat Biotechnol* 34:328-333 (2016).

AAV-PE-C was generated through Gibson assembly, by combining the following four DNA fragments: (i) gBlock split-intein C terminal, (ii) PCR amplified C-terminal PE2 (amino acid 714-1368 of SpCas9 H840A) and M-MLV RT from PE2, (iii) gBlock β-globin poly(A) signal, (iv) a KpnI/NotI-digested AAV backbone.

Example II

AAV Vector Production

AAV vectors (AAV8 capsids) were packaged at the Viral Vector Core of the Horae Gene Therapy Center at the University of Massachusetts Medical School. Vector titers were determined by gel electrophoresis followed by silver staining and qPCR.

Example III

Generation of Reporter Cells And Cell Culture Conditions

HEK293T cells were purchased from ATCC, and cells were maintained in Dulbecco's Modified Eagle's Medium supplemented with 10% FBS. For generation of the mCherry reporter and 47 bp insertion TLR reporter cells, single-copy reporter cells were created using the Invitrogen Flp-In system. Briefly, Flp-In 293T cells were maintained in DMEM, 10% Fetal bovine serum (FBS), 1% pen-strep and 100 μg/ml Zeocin. $1\times10^6$ Flp-In 293T cells were plated in a 6 well plate 24 hours before transfection. On the day of transfection, the cells were washed and fresh media without Zeocin was added.

The plasmid coding for FLP recombinase and the mCherry reporter or 47 bp insertion TLR reporter plasmid were transfected into the cells at a 9:1 ratio using Polyfect (QIAGEN) with 900 ng mCherry reporter or 47 bp-insertion TLR reporter plasmid and 100 ng FLP recombinase plasmid to make 1 μg plasmid in total. Forty-eight (48) hours following transfection, the cells were washed and split into a 10 cm dish with fresh media. One hundred (100) μg/ml of hygromycin was used to select for cells that contained an integration of the reporter plasmid. Two weeks post selection, hygromycin resistant foci were pooled and propagated for cryopreservation and further experiments.

The construction an characterization of the TLR-MCV1 reporter cells was previously described. Iyer et al., "Efficient Homology-directed Repair with Circular ssDNA Donors" bioRxiv, 786 864199 (2019). All cell types were maintained at 37° C. and 5% $CO_2$ and were tested negative for mycoplasma.

Example IV

Cell Culture Transfection/Electroporation And DNA Preparation

For transfection-based editing experiments in HEK293T cells or HEK293T reporter cells, cells were plated 100,000 per well on a 48-well plate. Twenty-four (24) hours later, the cells were co-transfected with 540 ng of prime editor plasmid, two hundred seventy (270) ng of pegRNA plasmid and ninety (90) ng of Nicking sgRNA plasmid. Lipofectamine 2000 (Invitrogen) was used for the transfection according to the manufacturer's instructions.

FACS analysis was performed three (3) days after transfection in HEK293T reporter cells. To detect editing efficiency in endogenous genomic loci, HEK293T cells were cultured for three (3) days after transfection, and genomic DNA was isolated using QIAamp DNA mini kit (QIAGEN) according to the manufacturer's instructions.

For CCR5 PE editing, 540 ng of prime editor plasmid, 270 ng of pegRNA plasmid and 90 ng of Nicking sgRNA plasmid were delivered, where $2\times10^5$ HeLa cells were treated per electroporation using the Neon® Transfection System 10 L Kit (Thermo Fisher Scientific) with the recommended electroporation parameters: Pulse voltage (1350 v), Pulse width (10 ms), Pulse number (3).

Example V

Fluorescent Reporter Assay

Forty-eight (48) h post-transfection cells are trypsinized and harvested into a microcentrifuge tube. Cells are centrifuged at 500×g for 2 min, washed once with 1×PBS, recentrifuged at 500×g for 2 min and resuspended in 1×PBS for flow cytometry (Becton Dickonson FACScan). Ten thousand (10,000) events were counted from each sample for FACS analysis. Experiments were performed in six replicates on different days. The data are reported as mean values with error bars indicating SD.

Example VI

Immunofluorescence And Immunohistochemistry

HeLa and U2OS cells are transfected in six-well format via Lipofectamine 2000 (Invitrogen) using the manufacturer's suggested protocol with 300 ng each PE expression plasmid and 150 ng of each pegRNA expression plasmid on a cover slip. Forty eight (48) h following transfection, transfection media was removed, cells were washed with 1×PBS and fixed with 4% formaldehyde in 1×PBS for 15 min at room temperature.

Following blocking (blocking solution: 2% BSA, 441 0.3% Triton X-100, within 1× PBS), samples were sequentially stained with mouse antihemagglutinin (Sigma, H9658, 1:500), and Alexa 488 donkey anti-mouse IgG (H+L; Invitrogen, A-21202, 1:2000). VECTASHIELD mounting medium with DAPI (Vector Laboratories, H-1200) was used to stain the nuclei and to mount the samples on the slide. Images were taken with ZEISS LSM 710 Confocal Microscope System. Fiji44 and the "CMCI-EMBL" plugin was used to calculate the signal from the nuclear or cytoplasm compartments as previously described. Miura, K., "Measurements of Intensity Dynamics at the Periphery of the Nucleus. *In: Bioimage Data Analysis Workflows. Learning Materials in Biosciences*. Eds: Miura K., Sladoje N. Springer, Cham. (2020); and github.com/miura/NucleusRimIntensityMeasurementsV2.

Sixty (60) to eighty (80) cells were used for each treatment group to determine the nuclear to cytoplasmic ratio for each PE construct, which was calculated as the intensity value from nucleus divided by the intensity value from cytoplasm and nucleus. IHC staining was performed using beta-catenin antibody (BD, 610154, 1:100) or HA tag (CST, 3724, 1:400). Xue et al., "CRISPR-mediated direct mutation of cancer genes in the mouse liver" Nature 514:380-385 (2014).

Example VII

Animal Studies

All animal experiments were authorized by the Institutional Animal Care and Use Committee (IACUC) at UMASS medical school. No animals were excluded from the analyses. All prime editor plasmids were prepared by EndoFreeMaxi kit (Qiagen) and were delivered through hydrodynamic tail-vein injection. For PiZ correction, eight-week-old PiZ mice were injected with 2.3 ml 0.9% saline containing 30 μg PE2 or PE2* (n=3), 15 μg pegRNA (SERPINA1) and 5 μg Nicking sgRNA.

For cancer model generation, FVB/NJ (Strain #001800) was purchased from Jackson Laboratories. Each FVB mouse (n=4) was injected with 2.3 ml 0.9% saline containing 30 μg PE2 or PE2*, 15 μg pegRNA (Ctnnb1), 15 μg Nicking sgRNA 2 (Ctnnb1), 5 μg pT3 EF1a-MYC (a gift from Xin Chen, Addgene plasmid #92046)33 and 1 μg CMV-SB10 (a gift from Perry Hackett, Addgene plasmid #24551).

Example VIII

Deep Sequencing and Data Analysis

Library construction for deep sequencing is modified from a previously published method. Bolukbasi et al., "Orthogonal Cas9-Cas9 chimeras provide a versatile platform for genome editing" *Nat Commun* 9:4856 (2018).

Briefly, 72 h after transfection or electroporation, cells were harvested and genomic DNA was extracted with GenElute Mammalian Genomic DNA Miniprep Kit (Sigma). Genomic loci spanning the target and off-target sites were PCR amplified with locus-specific primers carrying tails complementary to the Truseq adapters. Fifty (50) ng input genomic DNA was PCR amplified with Q5 High-Fidelity DNA Polymerase (New England Biolabs): (98° C., 15 s; 67° C. 25 s; 72° C. 20 s)×30 cycles.

For the construction of the CCR5 UMI-based library, 50 ng input genomic DNA was first linearly pre-amplified with 10 nM final concentration 5p-CCR5_UMI primer using the Q5 High-Fidelity DNA Polymerase (New England Biolabs): (98° C., 60 s; 67° C., 25 s; 72° C., 20 s)×10 cycles. In the same reaction mix, 500 nM final concentration 5p-DS_constant and 3p-CCR5_DS primers were added for further amplification (98° C., 60 s; 67° C., 25 s; 72° C., 20 s) for 30 cycles. Next, 0.1 μl of each PCR reaction was amplified with index-containing primers to reconstitute the TruSeq adaptors using the Q5 High-Fidelity DNA Polymerase (New England Biolabs): (98° C., 15 s; 67° C., 25 s; 72° C., 20 s)×10 cycles. Equal amounts of the PCR products from each experimental condition (identified by different indices) were pooled and gel purified.

The purified library was deep sequenced using a paired-end 150 bp Illumina MiniSeq run. First, the quality of paired-end sequencing reads (R1 and R2 fastq files) was assessed using FastQC bioinformatics.babraham.ac.uk/projects/fastqc/). Raw paired-end reads were combined using paired end read merger (PEAR) (PMID: 24142950) to generate single merged high-quality full-length reads. Reads were then filtered by quality (using Filter FASTQC (PMID: 20562416)) to remove those with a mean PHRED quality score under 30 and a minimum per base score under 24. Each group of reads was then aligned to a corresponding reference sequence using BWA (version 0.7.5) and SAMtools (version 0.1.19).

To determine indel frequency, size and distribution, all edited reads from each experimental replicate were combined and aligned, as described above. Indel types and frequencies were then cataloged in a text output format at each base using bam-readcount. github.com/genome/bam-readcount. For each treatment group, the average background indel frequencies (based on indel type, position and frequency) of the triplicate negative control group were subtracted to obtain the precise editing and indel frequencies for each group. The fraction of precise editing is calculated as sequencing reads with the desired allele editing/all reads for the target locus. The results were concatenated and loaded into GraphPad Prism 8.4 for data visualization.

Example IX

Tn5 Tagmentation and Library Preparation for UDiTaS

For tagmentation, a transposome was assembled using purified Tn5 protein and oligonucleotides purchased from IDT. Giannoukos et al., "UDiTaS™, a genome editing detection method for indels and genome rearrangements" BMC Genomics 19:212 (2018).

Two hundred (200) ng of genomic DNA was incubated with 2μl of assembled transposome at 55 degree for 7 mins, and the product was cleaned up (20 μl) with a Zymo column (Zymo Research, #D4013). Tagmented DNA was used for the 1st PCR using Platinum™ SuperFi DNA polymerase (Thermo) with i5 primer and gene specific primers. Table 3.

Two different libraries were prepared for gDNA from each mouse with different combinations of primers (i5+Locus_F [UDiTaS], i5+Locus_R [UDiTaS]). The i7 index was added in the 2nd PCR and the PCR product was cleaned up with Ampure XP SPRI beads (Agencourt, 0.9× reaction volume). Completed libraries were quantified by Tapestation and Qubit Agilent), pooled with equal mole and sequenced with 150 bp paired-end reads on an Illumina MiniSeq instrument.

Example X

UDiTaS Data Analysis

The analysis pipeline was built using python code. Briefly, the analysis steps are as follows:

i) Demultiplexing. Raw BCL files were converted and demultiplexed using the appropriate sequencing barcodes, allowing up to one mismatch in each barcode. Unique molecular identifiers (UMIs) for each read were extracted for further downstream analysis.

ii) Trimming. Remove 3' adapters using cutadapt, version 3.0;
journal.embnet.org/index.php/embnetjournal/article/view/200/479 iii) Create reference sequence based the UDiTaS locus-specific primer position and AAV plasmid map separately. Build index files for the reference using bowtie2-index46, version 2.4.0.

iv) Alignment analysis. Paired reads were then globally aligned (end-to-end mode) to all the reference amplicons using bowtie2's very sensitive parameter. Finally, samtools47 (version 0.1.19) was used to create and index sorted bam files. Paired-end reads covering a window between pegRNA targeting site and nicking sgRNA targeting sites were extracted and the total number of unique UMIs were counted. Precise editing or small indels were analyzed as previously described27. Pindel48 (version 0.2.5b8) was used to detect breakpoints of large deletions. Raw sequencing reads that align to the reference sequence were collapse to a single read by common UMI and categorized as an exemplar for each UMI to a specific category—for example, Wild Type, precise editing, small indel/substitution and Large Deletions. Then the number of UMIs assigned per category is determined to define the ratio of each event. v) AAV integration. Extract the unmapped reads that did not locally align to the AAV/plasmid in steps 3 and 4 using bedtools bamtofastq. With bowtie2, index the AAV plasmid sequence and then do a local alignment of the reads. Of the reads that locally align to the AAV plasmid, first filter out those reads which are directly adjacent to the UDiTaS primer (on read 2) and do not contain any target locus sequence. This removes reads that are due to false priming.

Of the remaining reads, collapse these by UMI and count the UMIs. Classify the exemplar read for each UMI as 'AAV/Plasmid Integrations'.

The software used for the above analysis is available at:
github.com/locusliu/GUIDESeq-Preprocess_from_Demultiplexing_to_Analysis
github.com/editasmedicine/uditas.
github.com/ericdanner/REPlacE_Analysis; and
github.com/locusliu/PCR_Amplicon_target_deep_seq/blob/master/CRESA-lpp.py.

Example XI

Statistical Analysis

The fold changes of editing (precise editing or indels) are calculated between the corresponding groups: pegRNA_only between PE2 and PE2*, or with specific Nicking sgRNA between PE2 and PE2*. Raw data statistical analyses were performed using GraphPad Prism 8.4. Sample size was not pre-determined by statistical methods, but rather, based on preliminary data. Group allocation was performed randomly.

In all studies, data represent biological replicates (n) and are depicted as mean±s.d. as indicated in the figure legends. Comparison of mean values was conducted with one-way ANOVA with Tukey's multiple comparisons test, as indicated in the figure legends. In all analyses, P values<0.05 were considered statistically significant.

We claim:

1. A method, comprising:

a) providing:

i) a patient having at least one causative mutation in a serpina1 gene allele linked to a genetic disease;

ii) a fusion protein complex comprising a fusion protein and a prime editing guide RNA molecule (pegRNA); wherein the fusion protein comprises a Cas9 nickase and a reverse transcriptase (RT), and wherein the fusion protein comprises an N-terminal c-Myc nuclear localization sequence (NLS) with the amino acid sequence SEQ ID NO: 8, an N-terminal NLS bipartite (BP)-SV40 NLS with the amino acid sequence SEQ ID NO: 5, a C-terminal variant BP (vBP)-SV40 NLS with the amino acid sequence SEQ ID NO: 7, and a SV40 NLS with the amino acid sequence SEQ ID NO: 6;

b) administering said fusion protein complex to said patient; and c) editing said at least one causative mutation resulting in a conversion to a wild type allele.

2. The method of claim 1, wherein said wild type allele is without editing-related indels.

3. The method of claim 1, wherein said fusion protein comprises a split-intein prime editor protein.

4. The method of claim 3, wherein said administering comprises administering said split-intein prime editor protein packaged in a dual adeno-associated virus platform.

5. The method of claim 1, wherein said genetic disease is alpha-1 antitrypsin deficiency (AATD).

6. The method of claim 1, wherein said conversion comprises a G•C-to-A•T base transition in said serpina1 gene allele.

7. The method of claim 1, wherein the amino acid sequence of the fusion protein consists of SEQ ID NO: 1.

8. The method of claim 1, wherein the amino acid sequence of the fusion protein consists of SEQ ID NO: 3.

* * * * *

SEQUENCE LISTING

```
<160> NUMBER OF SEQ ID NOS: 163

<210> SEQ ID NO 1
<211> LENGTH: 2146
<212> TYPE: PRT
<213> ORGANISM: Artificial Sequence
<220> FEATURE:
<223> OTHER INFORMATION: Synthetic

<400> SEQUENCE: 1
```

```
Pro Ala Ala Lys Arg Val Lys Leu Asp Gly Gly Lys Arg Thr Ala Asp
1               5                   10                  15

Gly Ser Glu Phe Glu Ser Pro Lys Lys Lys Arg Lys Val Asp Lys Lys
            20                  25                  30

Tyr Ser Ile Gly Leu Asp Ile Gly Thr Asn Ser Val Gly Trp Ala Val
        35                  40                  45

Ile Thr Asp Glu Tyr Lys Val Pro Ser Lys Lys Phe Lys Val Leu Gly
    50                  55                  60

Asn Thr Asp Arg His Ser Ile Lys Lys Asn Leu Ile Gly Ala Leu Leu
65                  70                  75                  80

Phe Asp Ser Gly Glu Thr Ala Glu Ala Thr Arg Leu Lys Arg Thr Ala
                85                  90                  95

Arg Arg Arg Tyr Thr Arg Arg Lys Asn Arg Ile Cys Tyr Leu Gln Glu
            100                 105                 110

Ile Phe Ser Asn Glu Met Ala Lys Val Asp Asp Ser Phe Phe His Arg
        115                 120                 125

Leu Glu Glu Ser Phe Leu Val Glu Glu Asp Lys Lys His Glu Arg His
    130                 135                 140

Pro Ile Phe Gly Asn Ile Val Asp Glu Val Ala Tyr His Glu Lys Tyr
145                 150                 155                 160

Pro Thr Ile Tyr His Leu Arg Lys Lys Leu Val Asp Ser Thr Asp Lys
                165                 170                 175

Ala Asp Leu Arg Leu Ile Tyr Leu Ala Leu Ala His Met Ile Lys Phe
            180                 185                 190

Arg Gly His Phe Leu Ile Glu Gly Asp Leu Asn Pro Asp Asn Ser Asp
        195                 200                 205

Val Asp Lys Leu Phe Ile Gln Leu Val Gln Thr Tyr Asn Gln Leu Phe
    210                 215                 220

Glu Glu Asn Pro Ile Asn Ala Ser Gly Val Asp Ala Lys Ala Ile Leu
225                 230                 235                 240

Ser Ala Arg Leu Ser Lys Ser Arg Arg Leu Glu Asn Leu Ile Ala Gln
                245                 250                 255

Leu Pro Gly Glu Lys Lys Asn Gly Leu Phe Gly Asn Leu Ile Ala Leu
            260                 265                 270

Ser Leu Gly Leu Thr Pro Asn Phe Lys Ser Asn Phe Asp Leu Ala Glu
        275                 280                 285

Asp Ala Lys Leu Gln Leu Ser Lys Asp Thr Tyr Asp Asp Asp Leu Asp
    290                 295                 300

Asn Leu Leu Ala Gln Ile Gly Asp Gln Tyr Ala Asp Leu Phe Leu Ala
305                 310                 315                 320

Ala Lys Asn Leu Ser Asp Ala Ile Leu Leu Ser Asp Ile Leu Arg Val
                325                 330                 335

Asn Thr Glu Ile Thr Lys Ala Pro Leu Ser Ala Ser Met Ile Lys Arg
            340                 345                 350

Tyr Asp Glu His His Gln Asp Leu Thr Leu Leu Lys Ala Leu Val Arg
        355                 360                 365

Gln Gln Leu Pro Glu Lys Tyr Lys Glu Ile Phe Phe Asp Gln Ser Lys
    370                 375                 380

Asn Gly Tyr Ala Gly Tyr Ile Asp Gly Gly Ala Ser Gln Glu Glu Phe
385                 390                 395                 400

Tyr Lys Phe Ile Lys Pro Ile Leu Glu Lys Met Asp Gly Thr Glu Glu
                405                 410                 415
```

```
Leu Leu Val Lys Leu Asn Arg Glu Asp Leu Leu Arg Lys Gln Arg Thr
            420                 425                 430

Phe Asp Asn Gly Ser Ile Pro His Gln Ile His Leu Gly Glu Leu His
        435                 440                 445

Ala Ile Leu Arg Arg Gln Glu Asp Phe Tyr Pro Phe Leu Lys Asp Asn
    450                 455                 460

Arg Glu Lys Ile Glu Lys Ile Leu Thr Phe Arg Ile Pro Tyr Tyr Val
465                 470                 475                 480

Gly Pro Leu Ala Arg Gly Asn Ser Arg Phe Ala Trp Met Thr Arg Lys
                485                 490                 495

Ser Glu Glu Thr Ile Thr Pro Trp Asn Phe Glu Glu Val Val Asp Lys
            500                 505                 510

Gly Ala Ser Ala Gln Ser Phe Ile Glu Arg Met Thr Asn Phe Asp Lys
        515                 520                 525

Asn Leu Pro Asn Glu Lys Val Leu Pro Lys His Ser Leu Leu Tyr Glu
    530                 535                 540

Tyr Phe Thr Val Tyr Asn Glu Leu Thr Lys Val Lys Tyr Val Thr Glu
545                 550                 555                 560

Gly Met Arg Lys Pro Ala Phe Leu Ser Gly Glu Gln Lys Lys Ala Ile
                565                 570                 575

Val Asp Leu Leu Phe Lys Thr Asn Arg Lys Val Thr Val Lys Gln Leu
            580                 585                 590

Lys Glu Asp Tyr Phe Lys Lys Ile Glu Cys Phe Asp Ser Val Glu Ile
        595                 600                 605

Ser Gly Val Glu Asp Arg Phe Asn Ala Ser Leu Gly Thr Tyr His Asp
    610                 615                 620

Leu Leu Lys Ile Ile Lys Asp Lys Asp Phe Leu Asp Asn Glu Glu Asn
625                 630                 635                 640

Glu Asp Ile Leu Glu Asp Ile Val Leu Thr Leu Thr Leu Phe Glu Asp
                645                 650                 655

Arg Glu Met Ile Glu Glu Arg Leu Lys Thr Tyr Ala His Leu Phe Asp
            660                 665                 670

Asp Lys Val Met Lys Gln Leu Lys Arg Arg Arg Tyr Thr Gly Trp Gly
        675                 680                 685

Arg Leu Ser Arg Lys Leu Ile Asn Gly Ile Arg Asp Lys Gln Ser Gly
    690                 695                 700

Lys Thr Ile Leu Asp Phe Leu Lys Ser Asp Gly Phe Ala Asn Arg Asn
705                 710                 715                 720

Phe Met Gln Leu Ile His Asp Asp Ser Leu Thr Phe Lys Glu Asp Ile
                725                 730                 735

Gln Lys Ala Gln Val Ser Gly Gln Gly Asp Ser Leu His Glu His Ile
            740                 745                 750

Ala Asn Leu Ala Gly Ser Pro Ala Ile Lys Lys Gly Ile Leu Gln Thr
        755                 760                 765

Val Lys Val Val Asp Glu Leu Val Lys Val Met Gly Arg His Lys Pro
    770                 775                 780

Glu Asn Ile Val Ile Glu Met Ala Arg Glu Asn Gln Thr Thr Gln Lys
785                 790                 795                 800

Gly Gln Lys Asn Ser Arg Glu Arg Met Lys Arg Ile Glu Glu Gly Ile
                805                 810                 815

Lys Glu Leu Gly Ser Gln Ile Leu Lys Glu His Pro Val Glu Asn Thr
            820                 825                 830

Gln Leu Gln Asn Glu Lys Leu Tyr Leu Tyr Tyr Leu Gln Asn Gly Arg
```

```
        835                 840                 845

Asp Met Tyr Val Asp Gln Glu Leu Asp Ile Asn Arg Leu Ser Asp Tyr
    850                 855                 860

Asp Val Asp Ala Ile Val Pro Gln Ser Phe Leu Lys Asp Asp Ser Ile
865                 870                 875                 880

Asp Asn Lys Val Leu Thr Arg Ser Asp Lys Asn Arg Gly Lys Ser Asp
                885                 890                 895

Asn Val Pro Ser Glu Glu Val Val Lys Lys Met Lys Asn Tyr Trp Arg
            900                 905                 910

Gln Leu Leu Asn Ala Lys Leu Ile Thr Gln Arg Lys Phe Asp Asn Leu
        915                 920                 925

Thr Lys Ala Glu Arg Gly Gly Leu Ser Glu Leu Asp Lys Ala Gly Phe
    930                 935                 940

Ile Lys Arg Gln Leu Val Glu Thr Arg Gln Ile Thr Lys His Val Ala
945                 950                 955                 960

Gln Ile Leu Asp Ser Arg Met Asn Thr Lys Tyr Asp Glu Asn Asp Lys
                965                 970                 975

Leu Ile Arg Glu Val Lys Val Ile Thr Leu Lys Ser Lys Leu Val Ser
            980                 985                 990

Asp Phe Arg Lys Asp Phe Gln Phe  Tyr Lys Val Arg Glu  Ile Asn Asn
        995                 1000                1005

Tyr His  His Ala His Asp Ala  Tyr Leu Asn Ala Val  Val Gly Thr
    1010                1015                1020

Ala Leu  Ile Lys Lys Tyr Pro  Lys Leu Glu Ser Glu  Phe Val Tyr
    1025                1030                1035

Gly Asp  Tyr Lys Val Tyr Asp  Val Arg Lys Met Ile  Ala Lys Ser
    1040                1045                1050

Glu Gln  Glu Ile Gly Lys Ala  Thr Ala Lys Tyr Phe  Phe Tyr Ser
    1055                1060                1065

Asn Ile  Met Asn Phe Phe Lys  Thr Glu Ile Thr Leu  Ala Asn Gly
    1070                1075                1080

Glu Ile  Arg Lys Arg Pro Leu  Ile Glu Thr Asn Gly  Glu Thr Gly
    1085                1090                1095

Glu Ile  Val Trp Asp Lys Gly  Arg Asp Phe Ala Thr  Val Arg Lys
    1100                1105                1110

Val Leu  Ser Met Pro Gln Val  Asn Ile Val Lys Lys  Thr Glu Val
    1115                1120                1125

Gln Thr  Gly Gly Phe Ser Lys  Glu Ser Ile Leu Pro  Lys Arg Asn
    1130                1135                1140

Ser Asp  Lys Leu Ile Ala Arg  Lys Lys Asp Trp Asp  Pro Lys Lys
    1145                1150                1155

Tyr Gly  Gly Phe Asp Ser Pro  Thr Val Ala Tyr Ser  Val Leu Val
    1160                1165                1170

Val Ala  Lys Val Glu Lys Gly  Lys Ser Lys Lys Leu  Lys Ser Val
    1175                1180                1185

Lys Glu  Leu Leu Gly Ile Thr  Ile Met Glu Arg Ser  Ser Phe Glu
    1190                1195                1200

Lys Asn  Pro Ile Asp Phe Leu  Glu Ala Lys Gly Tyr  Lys Glu Val
    1205                1210                1215

Lys Lys  Asp Leu Ile Ile Lys  Leu Pro Lys Tyr Ser  Leu Phe Glu
    1220                1225                1230

Leu Glu  Asn Gly Arg Lys Arg  Met Leu Ala Ser Ala  Gly Glu Leu
    1235                1240                1245
```

```
Gln Lys  Gly Asn Glu Leu Ala  Leu Pro Ser Lys Tyr  Val Asn Phe
    1250                 1255                 1260

Leu Tyr  Leu Ala Ser His Tyr  Glu Lys Leu Lys Gly  Ser Pro Glu
    1265                 1270                 1275

Asp Asn  Glu Gln Lys Gln Leu  Phe Val Glu Gln His  Lys His Tyr
    1280                 1285                 1290

Leu Asp  Glu Ile Ile Glu Gln  Ile Ser Glu Phe Ser  Lys Arg Val
    1295                 1300                 1305

Ile Leu  Ala Asp Ala Asn Leu  Asp Lys Val Leu Ser  Ala Tyr Asn
    1310                 1315                 1320

Lys His  Arg Asp Lys Pro Ile  Arg Glu Gln Ala Glu  Asn Ile Ile
    1325                 1330                 1335

His Leu  Phe Thr Leu Thr Asn  Leu Gly Ala Pro Ala  Ala Phe Lys
    1340                 1345                 1350

Tyr Phe  Asp Thr Thr Ile Asp  Arg Lys Arg Tyr Thr  Ser Thr Lys
    1355                 1360                 1365

Glu Val  Leu Asp Ala Thr Leu  Ile His Gln Ser Ile  Thr Gly Leu
    1370                 1375                 1380

Tyr Glu  Thr Arg Ile Asp Leu  Ser Gln Leu Gly Gly  Asp Ser Gly
    1385                 1390                 1395

Gly Ser  Ser Gly Gly Ser Ser  Gly Ser Glu Thr Pro  Gly Thr Ser
    1400                 1405                 1410

Glu Ser  Ala Thr Pro Glu Ser  Ser Gly Gly Ser Ser  Gly Gly Ser
    1415                 1420                 1425

Ser Thr  Leu Asn Ile Glu Asp  Glu Tyr Arg Leu His  Glu Thr Ser
    1430                 1435                 1440

Lys Glu  Pro Asp Val Ser Leu  Gly Ser Thr Trp Leu  Ser Asp Phe
    1445                 1450                 1455

Pro Gln  Ala Trp Ala Glu Thr  Gly Gly Met Gly Leu  Ala Val Arg
    1460                 1465                 1470

Gln Ala  Pro Leu Ile Ile Pro  Leu Lys Ala Thr Ser  Thr Pro Val
    1475                 1480                 1485

Ser Ile  Lys Gln Tyr Pro Met  Ser Gln Glu Ala Arg  Leu Gly Ile
    1490                 1495                 1500

Lys Pro  His Ile Gln Arg Leu  Leu Asp Gln Gly Ile  Leu Val Pro
    1505                 1510                 1515

Cys Gln  Ser Pro Trp Asn Thr  Pro Leu Leu Pro Val  Lys Lys Pro
    1520                 1525                 1530

Gly Thr  Asn Asp Tyr Arg Pro  Val Gln Asp Leu Arg  Glu Val Asn
    1535                 1540                 1545

Lys Arg  Val Glu Asp Ile His  Pro Thr Val Pro Asn  Pro Tyr Asn
    1550                 1555                 1560

Leu Leu  Ser Gly Leu Pro Pro  Ser His Gln Trp Tyr  Thr Val Leu
    1565                 1570                 1575

Asp Leu  Lys Asp Ala Phe Phe  Cys Leu Arg Leu His  Pro Thr Ser
    1580                 1585                 1590

Gln Pro  Leu Phe Ala Phe Glu  Trp Arg Asp Pro Glu  Met Gly Ile
    1595                 1600                 1605

Ser Gly  Gln Leu Thr Trp Thr  Arg Leu Pro Gln Gly  Phe Lys Asn
    1610                 1615                 1620

Ser Pro  Thr Leu Phe Asn Glu  Ala Leu His Arg Asp  Leu Ala Asp
    1625                 1630                 1635
```

-continued

```
Phe Arg  Ile Gln His Pro Asp  Leu Ile Leu Leu Gln  Tyr Val Asp
    1640                 1645                 1650

Asp Leu  Leu Leu Ala Ala Thr  Ser Glu Leu Asp Cys  Gln Gln Gly
    1655                 1660                 1665

Thr Arg  Ala Leu Leu Gln Thr  Leu Gly Asn Leu Gly  Tyr Arg Ala
    1670                 1675                 1680

Ser Ala  Lys Lys Ala Gln Ile  Cys Gln Lys Gln Val  Lys Tyr Leu
    1685                 1690                 1695

Gly Tyr  Leu Leu Lys Glu Gly  Gln Arg Trp Leu Thr  Glu Ala Arg
    1700                 1705                 1710

Lys Glu  Thr Val Met Gly Gln  Pro Thr Pro Lys Thr  Pro Arg Gln
    1715                 1720                 1725

Leu Arg  Glu Phe Leu Gly Lys  Ala Gly Phe Cys Arg  Leu Phe Ile
    1730                 1735                 1740

Pro Gly  Phe Ala Glu Met Ala  Ala Pro Leu Tyr Pro  Leu Thr Lys
    1745                 1750                 1755

Pro Gly  Thr Leu Phe Asn Trp  Gly Pro Asp Gln Gln  Lys Ala Tyr
    1760                 1765                 1770

Gln Glu  Ile Lys Gln Ala Leu  Leu Thr Ala Pro Ala  Leu Gly Leu
    1775                 1780                 1785

Pro Asp  Leu Thr Lys Pro Phe  Glu Leu Phe Val Asp  Glu Lys Gln
    1790                 1795                 1800

Gly Tyr  Ala Lys Gly Val Leu  Thr Gln Lys Leu Gly  Pro Trp Arg
    1805                 1810                 1815

Arg Pro  Val Ala Tyr Leu Ser  Lys Lys Leu Asp Pro  Val Ala Ala
    1820                 1825                 1830

Gly Trp  Pro Pro Cys Leu Arg  Met Val Ala Ala Ile  Ala Val Leu
    1835                 1840                 1845

Thr Lys  Asp Ala Gly Lys Leu  Thr Met Gly Gln Pro  Leu Val Ile
    1850                 1855                 1860

Leu Ala  Pro His Ala Val Glu  Ala Leu Val Lys Gln  Pro Pro Asp
    1865                 1870                 1875

Arg Trp  Leu Ser Asn Ala Arg  Met Thr His Tyr Gln  Ala Leu Leu
    1880                 1885                 1890

Leu Asp  Thr Asp Arg Val Gln  Phe Gly Pro Val Val  Ala Leu Asn
    1895                 1900                 1905

Pro Ala  Thr Leu Leu Pro Leu  Pro Glu Glu Gly Leu  Gln His Asn
    1910                 1915                 1920

Cys Leu  Asp Ile Leu Ala Glu  Ala His Gly Thr Arg  Pro Asp Leu
    1925                 1930                 1935

Thr Asp  Gln Pro Leu Pro Asp  Ala Asp His Thr Trp  Tyr Thr Asp
    1940                 1945                 1950

Gly Ser  Ser Leu Leu Gln Glu  Gly Gln Arg Lys Ala  Gly Ala Ala
    1955                 1960                 1965

Val Thr  Thr Glu Thr Glu Val  Ile Trp Ala Lys Ala  Leu Pro Ala
    1970                 1975                 1980

Gly Thr  Ser Ala Gln Arg Ala  Glu Leu Ile Ala Leu  Thr Gln Ala
    1985                 1990                 1995

Leu Lys  Met Ala Glu Gly Lys  Lys Leu Asn Val Tyr  Thr Asp Ser
    2000                 2005                 2010

Arg Tyr  Ala Phe Ala Thr Ala  His Ile His Gly Glu  Ile Tyr Arg
    2015                 2020                 2025

Arg Arg  Gly Trp Leu Thr Ser  Glu Gly Lys Glu Ile  Lys Asn Lys
```

2030 2035 2040

Asp Glu Ile Leu Ala Leu Leu Lys Ala Leu Phe Leu Pro Lys Arg
2045 2050 2055

Leu Ser Ile Ile His Cys Pro Gly His Gln Lys Gly His Ser Ala
2060 2065 2070

Glu Ala Arg Gly Asn Arg Met Ala Asp Gln Ala Ala Arg Lys Ala
2075 2080 2085

Ala Ile Thr Glu Thr Pro Asp Thr Ser Thr Leu Leu Ile Glu Asn
2090 2095 2100

Ser Ser Pro Ser Gly Gly Ser Lys Arg Thr Ala Asp Gly Ser Glu
2105 2110 2115

Lys Arg Thr Ala Asp Ser Gln His Ser Thr Pro Pro Lys Thr Lys
2120 2125 2130

Arg Lys Val Glu Phe Glu Pro Lys Lys Lys Arg Lys Val
2135 2140 2145

<210> SEQ ID NO 2
<211> LENGTH: 1839
<212> TYPE: PRT
<213> ORGANISM: Artificial Sequence
<220> FEATURE:
<223> OTHER INFORMATION: Synthetic

<400> SEQUENCE: 2

Pro Ala Ala Lys Arg Val Lys Leu Asp Gly Gly Lys Arg Thr Ala Asp
1 5 10 15

Gly Ser Glu Phe Glu Ser Pro Lys Lys Lys Arg Lys Val Gly Ile His
20 25 30

Gly Val Pro Ala Ala Lys Arg Asn Tyr Ile Leu Gly Leu Asp Ile Gly
35 40 45

Ile Thr Ser Val Gly Tyr Gly Ile Ile Asp Tyr Glu Thr Arg Asp Val
50 55 60

Ile Asp Ala Gly Val Arg Leu Phe Lys Glu Ala Asn Val Glu Asn Asn
65 70 75 80

Glu Gly Arg Arg Ser Lys Arg Gly Ala Arg Arg Leu Lys Arg Arg Arg
85 90 95

Arg His Arg Ile Gln Arg Val Lys Lys Leu Leu Phe Asp Tyr Asn Leu
100 105 110

Leu Thr Asp His Ser Glu Leu Ser Gly Ile Asn Pro Tyr Glu Ala Arg
115 120 125

Val Lys Gly Leu Ser Gln Lys Leu Ser Glu Glu Glu Phe Ser Ala Ala
130 135 140

Leu Leu His Leu Ala Lys Arg Arg Gly Val His Asn Val Asn Glu Val
145 150 155 160

Glu Glu Asp Thr Gly Asn Glu Leu Ser Thr Lys Glu Gln Ile Ser Arg
165 170 175

Asn Ser Lys Ala Leu Glu Glu Lys Tyr Val Ala Glu Leu Gln Leu Glu
180 185 190

Arg Leu Lys Lys Asp Gly Glu Val Arg Gly Ser Ile Asn Arg Phe Lys
195 200 205

Thr Ser Asp Tyr Val Lys Glu Ala Lys Gln Leu Leu Lys Val Gln Lys
210 215 220

Ala Tyr His Gln Leu Asp Gln Ser Phe Ile Asp Thr Tyr Ile Asp Leu
225 230 235 240

Leu Glu Thr Arg Arg Thr Tyr Tyr Glu Gly Pro Gly Glu Gly Ser Pro

-continued

```
                245                 250                 255

Phe Gly Trp Lys Asp Ile Lys Glu Trp Tyr Glu Met Leu Met Gly His
            260                 265                 270

Cys Thr Tyr Phe Pro Glu Glu Leu Arg Ser Val Lys Tyr Ala Tyr Asn
        275                 280                 285

Ala Asp Leu Tyr Asn Ala Leu Asn Asp Leu Asn Asn Leu Val Ile Thr
    290                 295                 300

Arg Asp Glu Asn Glu Lys Leu Glu Tyr Tyr Glu Lys Phe Gln Ile Ile
305                 310                 315                 320

Glu Asn Val Phe Lys Gln Lys Lys Lys Pro Thr Leu Lys Gln Ile Ala
                325                 330                 335

Lys Glu Ile Leu Val Asn Glu Glu Asp Ile Lys Gly Tyr Arg Val Thr
            340                 345                 350

Ser Thr Gly Lys Pro Glu Phe Thr Asn Leu Lys Val Tyr His Asp Ile
        355                 360                 365

Lys Asp Ile Thr Ala Arg Lys Glu Ile Ile Glu Asn Ala Glu Leu Leu
    370                 375                 380

Asp Gln Ile Ala Lys Ile Leu Thr Ile Tyr Gln Ser Ser Glu Asp Ile
385                 390                 395                 400

Gln Glu Glu Leu Thr Asn Leu Asn Ser Glu Leu Thr Gln Glu Glu Ile
                405                 410                 415

Glu Gln Ile Ser Asn Leu Lys Gly Tyr Thr Gly Thr His Asn Leu Ser
            420                 425                 430

Leu Lys Ala Ile Asn Leu Ile Leu Asp Glu Leu Trp His Thr Asn Asp
        435                 440                 445

Asn Gln Ile Ala Ile Phe Asn Arg Leu Lys Leu Val Pro Lys Lys Val
    450                 455                 460

Asp Leu Ser Gln Gln Lys Glu Ile Pro Thr Thr Leu Val Asp Asp Phe
465                 470                 475                 480

Ile Leu Ser Pro Val Val Lys Arg Ser Phe Ile Gln Ser Ile Lys Val
                485                 490                 495

Ile Asn Ala Ile Ile Lys Lys Tyr Gly Leu Pro Asn Asp Ile Ile Ile
            500                 505                 510

Glu Leu Ala Arg Glu Lys Asn Ser Lys Asp Ala Gln Lys Met Ile Asn
        515                 520                 525

Glu Met Gln Lys Arg Asn Arg Gln Thr Asn Glu Arg Ile Glu Glu Ile
    530                 535                 540

Ile Arg Thr Thr Gly Lys Glu Asn Ala Lys Tyr Leu Ile Glu Lys Ile
545                 550                 555                 560

Lys Leu His Asp Met Gln Glu Gly Lys Cys Leu Tyr Ser Leu Glu Ala
                565                 570                 575

Ile Pro Leu Glu Asp Leu Leu Asn Asn Pro Phe Asn Tyr Glu Val Asp
            580                 585                 590

His Ile Ile Pro Arg Ser Val Ser Phe Asp Asn Ser Phe Asn Asn Lys
        595                 600                 605

Val Leu Val Lys Gln Glu Glu Ala Ser Lys Lys Gly Asn Arg Thr Pro
    610                 615                 620

Phe Gln Tyr Leu Ser Ser Ser Asp Ser Lys Ile Ser Tyr Glu Thr Phe
625                 630                 635                 640

Lys Lys His Ile Leu Asn Leu Ala Lys Gly Lys Gly Arg Ile Ser Lys
                645                 650                 655

Thr Lys Lys Glu Tyr Leu Leu Glu Glu Arg Asp Ile Asn Arg Phe Ser
            660                 665                 670
```

-continued

```
Val Gln Lys Asp Phe Ile Asn Arg Asn Leu Val Asp Thr Arg Tyr Ala
        675                 680                 685

Thr Arg Gly Leu Met Asn Leu Leu Arg Ser Tyr Phe Arg Val Asn Asn
    690                 695                 700

Leu Asp Val Lys Val Lys Ser Ile Asn Gly Gly Phe Thr Ser Phe Leu
705                 710                 715                 720

Arg Arg Lys Trp Lys Phe Lys Lys Glu Arg Asn Lys Gly Tyr Lys His
                725                 730                 735

His Ala Glu Asp Ala Leu Ile Ile Ala Asn Ala Asp Phe Ile Phe Lys
            740                 745                 750

Glu Trp Lys Lys Leu Asp Lys Ala Lys Lys Val Met Glu Asn Gln Met
        755                 760                 765

Phe Glu Glu Lys Gln Ala Glu Ser Met Pro Glu Ile Glu Thr Glu Gln
    770                 775                 780

Glu Tyr Lys Glu Ile Phe Ile Thr Pro His Gln Ile Lys His Ile Lys
785                 790                 795                 800

Asp Phe Lys Asp Tyr Lys Tyr Ser His Arg Val Asp Lys Lys Pro Asn
                805                 810                 815

Arg Glu Leu Ile Asn Asp Thr Leu Tyr Ser Thr Arg Lys Asp Asp Lys
            820                 825                 830

Gly Asn Thr Leu Ile Val Asn Asn Leu Asn Gly Leu Tyr Asp Lys Asp
        835                 840                 845

Asn Asp Lys Leu Lys Lys Leu Ile Asn Lys Ser Pro Glu Lys Leu Leu
    850                 855                 860

Met Tyr His His Asp Pro Gln Thr Tyr Gln Lys Leu Lys Leu Ile Met
865                 870                 875                 880

Glu Gln Tyr Gly Asp Glu Lys Asn Pro Leu Tyr Lys Tyr Tyr Glu Glu
                885                 890                 895

Thr Gly Asn Tyr Leu Thr Lys Tyr Ser Lys Lys Asp Asn Gly Pro Val
            900                 905                 910

Ile Lys Lys Ile Lys Tyr Tyr Gly Asn Lys Leu Asn Ala His Leu Asp
        915                 920                 925

Ile Thr Asp Asp Tyr Pro Asn Ser Arg Asn Lys Val Val Lys Leu Ser
    930                 935                 940

Leu Lys Pro Tyr Arg Phe Asp Val Tyr Leu Asp Asn Gly Val Tyr Lys
945                 950                 955                 960

Phe Val Thr Val Lys Asn Leu Asp Val Ile Lys Lys Glu Asn Tyr Tyr
                965                 970                 975

Glu Val Asn Ser Lys Cys Tyr Glu Glu Ala Lys Lys Leu Lys Lys Ile
            980                 985                 990

Ser Asn Gln Ala Glu Phe Ile Ala  Ser Phe Tyr Asn Asn  Asp Leu Ile
        995                 1000                1005

Lys Ile  Asn Gly Glu Leu Tyr  Arg Val Ile Gly Val  Asn Asn Asp
    1010                1015                1020

Leu Leu  Asn Arg Ile Glu Val  Asn Met Ile Asp Ile  Thr Tyr Arg
    1025                1030                1035

Glu Tyr  Leu Glu Asn Met Asn  Asp Lys Arg Pro Pro  Arg Ile Ile
    1040                1045                1050

Lys Thr  Ile Ala Ser Lys Thr  Gln Ser Ile Lys Lys  Tyr Ser Thr
    1055                1060                1065

Asp Ile  Leu Gly Asn Leu Tyr  Glu Val Lys Ser Lys  Lys His Pro
    1070                1075                1080
```

```
Gln Ile  Ile Lys Lys Gly Ser  Gly Gly Ser Ser Gly  Gly Ser Ser
    1085                 1090                 1095

Gly Ser  Glu Thr Pro Gly Thr  Ser Glu Ser Ala Thr  Pro Glu Ser
    1100                 1105                 1110

Ser Gly  Gly Ser Ser Gly Gly  Ser Ser Thr Leu Asn  Ile Glu Asp
    1115                 1120                 1125

Glu Tyr  Arg Leu His Glu Thr  Ser Lys Glu Pro Asp  Val Ser Leu
    1130                 1135                 1140

Gly Ser  Thr Trp Leu Ser Asp  Phe Pro Gln Ala Trp  Ala Glu Thr
    1145                 1150                 1155

Gly Gly  Met Gly Leu Ala Val  Arg Gln Ala Pro Leu  Ile Ile Pro
    1160                 1165                 1170

Leu Lys  Ala Thr Ser Thr Pro  Val Ser Ile Lys Gln  Tyr Pro Met
    1175                 1180                 1185

Ser Gln  Glu Ala Arg Leu Gly  Ile Lys Pro His Ile  Gln Arg Leu
    1190                 1195                 1200

Leu Asp  Gln Gly Ile Leu Val  Pro Cys Gln Ser Pro  Trp Asn Thr
    1205                 1210                 1215

Pro Leu  Leu Pro Val Lys Lys  Pro Gly Thr Asn Asp  Tyr Arg Pro
    1220                 1225                 1230

Val Gln  Asp Leu Arg Glu Val  Asn Lys Arg Val Glu  Asp Ile His
    1235                 1240                 1245

Pro Thr  Val Pro Asn Pro Tyr  Asn Leu Leu Ser Gly  Leu Pro Pro
    1250                 1255                 1260

Ser His  Gln Trp Tyr Thr Val  Leu Asp Leu Lys Asp  Ala Phe Phe
    1265                 1270                 1275

Cys Leu  Arg Leu His Pro Thr  Ser Gln Pro Leu Phe  Ala Phe Glu
    1280                 1285                 1290

Trp Arg  Asp Pro Glu Met Gly  Ile Ser Gly Gln Leu  Thr Trp Thr
    1295                 1300                 1305

Arg Leu  Pro Gln Gly Phe Lys  Asn Ser Pro Thr Leu  Phe Asn Glu
    1310                 1315                 1320

Ala Leu  His Arg Asp Leu Ala  Asp Phe Arg Ile Gln  His Pro Asp
    1325                 1330                 1335

Leu Ile  Leu Leu Gln Tyr Val  Asp Asp Leu Leu Leu  Ala Ala Thr
    1340                 1345                 1350

Ser Glu  Leu Asp Cys Gln Gln  Gly Thr Arg Ala Leu  Leu Gln Thr
    1355                 1360                 1365

Leu Gly  Asn Leu Gly Tyr Arg  Ala Ser Ala Lys Lys  Ala Gln Ile
    1370                 1375                 1380

Cys Gln  Lys Gln Val Lys Tyr  Leu Gly Tyr Leu Leu  Lys Glu Gly
    1385                 1390                 1395

Gln Arg  Trp Leu Thr Glu Ala  Arg Lys Glu Thr Val  Met Gly Gln
    1400                 1405                 1410

Pro Thr  Pro Lys Thr Pro Arg  Gln Leu Arg Glu Phe  Leu Gly Lys
    1415                 1420                 1425

Ala Gly  Phe Cys Arg Leu Phe  Ile Pro Gly Phe Ala  Glu Met Ala
    1430                 1435                 1440

Ala Pro  Leu Tyr Pro Leu Thr  Lys Pro Gly Thr Leu  Phe Asn Trp
    1445                 1450                 1455

Gly Pro  Asp Gln Gln Lys Ala  Tyr Gln Glu Ile Lys  Gln Ala Leu
    1460                 1465                 1470

Leu Thr  Ala Pro Ala Leu Gly  Leu Pro Asp Leu Thr  Lys Pro Phe
```

```
    1475                1480                1485

Glu Leu  Phe Val Asp Glu Lys  Gln Gly Tyr Ala Lys  Gly Val Leu
    1490                1495                1500

Thr Gln  Lys Leu Gly Pro Trp  Arg Arg Pro Val Ala  Tyr Leu Ser
    1505                1510                1515

Lys Lys  Leu Asp Pro Val Ala  Ala Gly Trp Pro Pro  Cys Leu Arg
    1520                1525                1530

Met Val  Ala Ala Ile Ala Val  Leu Thr Lys Asp Ala  Gly Lys Leu
    1535                1540                1545

Thr Met  Gly Gln Pro Leu Val  Ile Leu Ala Pro His  Ala Val Glu
    1550                1555                1560

Ala Leu  Val Lys Gln Pro Pro  Asp Arg Trp Leu Ser  Asn Ala Arg
    1565                1570                1575

Met Thr  His Tyr Gln Ala Leu  Leu Leu Asp Thr Asp  Arg Val Gln
    1580                1585                1590

Phe Gly  Pro Val Val Ala Leu  Asn Pro Ala Thr Leu  Leu Pro Leu
    1595                1600                1605

Pro Glu  Glu Gly Leu Gln His  Asn Cys Leu Asp Ile  Leu Ala Glu
    1610                1615                1620

Ala His  Gly Thr Arg Pro Asp  Leu Thr Asp Gln Pro  Leu Pro Asp
    1625                1630                1635

Ala Asp  His Thr Trp Tyr Thr  Asp Gly Ser Ser Leu  Leu Gln Glu
    1640                1645                1650

Gly Gln  Arg Lys Ala Gly Ala  Ala Val Thr Thr Glu  Thr Glu Val
    1655                1660                1665

Ile Trp  Ala Lys Ala Leu Pro  Ala Gly Thr Ser Ala  Gln Arg Ala
    1670                1675                1680

Glu Leu  Ile Ala Leu Thr Gln  Ala Leu Lys Met Ala  Glu Gly Lys
    1685                1690                1695

Lys Leu  Asn Val Tyr Thr Asp  Ser Arg Tyr Ala Phe  Ala Thr Ala
    1700                1705                1710

His Ile  His Gly Glu Ile Tyr  Arg Arg Arg Gly Trp  Leu Thr Ser
    1715                1720                1725

Glu Gly  Lys Glu Ile Lys Asn  Lys Asp Glu Ile Leu  Ala Leu Leu
    1730                1735                1740

Lys Ala  Leu Phe Leu Pro Lys  Arg Leu Ser Ile Ile  His Cys Pro
    1745                1750                1755

Gly His  Gln Lys Gly His Ser  Ala Glu Ala Arg Gly  Asn Arg Met
    1760                1765                1770

Ala Asp  Gln Ala Ala Arg Lys  Ala Ala Ile Thr Glu  Thr Pro Asp
    1775                1780                1785

Thr Ser  Thr Leu Leu Ile Glu  Asn Ser Ser Pro Ser  Gly Gly Ser
    1790                1795                1800

Lys Arg  Thr Ala Asp Gly Ser  Glu Lys Arg Thr Ala  Asp Ser Gln
    1805                1810                1815

His Ser  Thr Pro Pro Lys Thr  Lys Arg Lys Val Glu  Phe Glu Pro
    1820                1825                1830

Lys Lys  Lys Arg Lys Val
    1835

<210> SEQ ID NO 3
<211> LENGTH: 1839
<212> TYPE: PRT
<213> ORGANISM: Artificial Sequence
```

<220> FEATURE:
<223> OTHER INFORMATION: Synthetic

<400> SEQUENCE: 3

```
Pro Ala Ala Lys Arg Val Lys Leu Asp Gly Gly Lys Arg Thr Ala Asp
1               5                   10                  15

Gly Ser Glu Phe Glu Ser Pro Lys Lys Lys Arg Lys Val Gly Ile His
            20                  25                  30

Gly Val Pro Ala Ala Lys Arg Asn Tyr Ile Leu Gly Leu Asp Ile Gly
        35                  40                  45

Ile Thr Ser Val Gly Tyr Gly Ile Ile Asp Tyr Glu Thr Arg Asp Val
    50                  55                  60

Ile Asp Ala Gly Val Arg Leu Phe Lys Glu Ala Asn Val Glu Asn Asn
65                  70                  75                  80

Glu Gly Arg Arg Ser Lys Arg Gly Ala Arg Arg Leu Lys Arg Arg Arg
                85                  90                  95

Arg His Arg Ile Gln Arg Val Lys Lys Leu Leu Phe Asp Tyr Asn Leu
            100                 105                 110

Leu Thr Asp His Ser Glu Leu Ser Gly Ile Asn Pro Tyr Glu Ala Arg
        115                 120                 125

Val Lys Gly Leu Ser Gln Lys Leu Ser Glu Glu Glu Phe Ser Ala Ala
    130                 135                 140

Leu Leu His Leu Ala Lys Arg Arg Gly Val His Asn Val Asn Glu Val
145                 150                 155                 160

Glu Glu Asp Thr Gly Asn Glu Leu Ser Thr Lys Glu Gln Ile Ser Arg
                165                 170                 175

Asn Ser Lys Ala Leu Glu Glu Lys Tyr Val Ala Glu Leu Gln Leu Glu
            180                 185                 190

Arg Leu Lys Lys Asp Gly Glu Val Arg Gly Ser Ile Asn Arg Phe Lys
        195                 200                 205

Thr Ser Asp Tyr Val Lys Glu Ala Lys Gln Leu Leu Lys Val Gln Lys
    210                 215                 220

Ala Tyr His Gln Leu Asp Gln Ser Phe Ile Asp Thr Tyr Ile Asp Leu
225                 230                 235                 240

Leu Glu Thr Arg Arg Thr Tyr Tyr Glu Gly Pro Gly Glu Gly Ser Pro
                245                 250                 255

Phe Gly Trp Lys Asp Ile Lys Glu Trp Tyr Glu Met Leu Met Gly His
            260                 265                 270

Cys Thr Tyr Phe Pro Glu Glu Leu Arg Ser Val Lys Tyr Ala Tyr Asn
        275                 280                 285

Ala Asp Leu Tyr Asn Ala Leu Asn Asp Leu Asn Asn Leu Val Ile Thr
    290                 295                 300

Arg Asp Glu Asn Glu Lys Leu Glu Tyr Tyr Glu Lys Phe Gln Ile Ile
305                 310                 315                 320

Glu Asn Val Phe Lys Gln Lys Lys Lys Pro Thr Leu Lys Gln Ile Ala
                325                 330                 335

Lys Glu Ile Leu Val Asn Glu Glu Asp Ile Lys Gly Tyr Arg Val Thr
            340                 345                 350

Ser Thr Gly Lys Pro Glu Phe Thr Asn Leu Lys Val Tyr His Asp Ile
        355                 360                 365

Lys Asp Ile Thr Ala Arg Lys Glu Ile Ile Glu Asn Ala Glu Leu Leu
    370                 375                 380

Asp Gln Ile Ala Lys Ile Leu Thr Ile Tyr Gln Ser Ser Glu Asp Ile
385                 390                 395                 400
```

```
Gln Glu Glu Leu Thr Asn Leu Asn Ser Glu Leu Thr Gln Glu Glu Ile
                405                 410                 415

Glu Gln Ile Ser Asn Leu Lys Gly Tyr Thr Gly Thr His Asn Leu Ser
            420                 425                 430

Leu Lys Ala Ile Asn Leu Ile Leu Asp Glu Leu Trp His Thr Asn Asp
        435                 440                 445

Asn Gln Ile Ala Ile Phe Asn Arg Leu Lys Leu Val Pro Lys Lys Val
    450                 455                 460

Asp Leu Ser Gln Gln Lys Glu Ile Pro Thr Thr Leu Val Asp Asp Phe
465                 470                 475                 480

Ile Leu Ser Pro Val Val Lys Arg Ser Phe Ile Gln Ser Ile Lys Val
                485                 490                 495

Ile Asn Ala Ile Ile Lys Lys Tyr Gly Leu Pro Asn Asp Ile Ile Ile
            500                 505                 510

Glu Leu Ala Arg Glu Lys Asn Ser Lys Asp Ala Gln Lys Met Ile Asn
        515                 520                 525

Glu Met Gln Lys Arg Asn Arg Gln Thr Asn Glu Arg Ile Glu Glu Ile
    530                 535                 540

Ile Arg Thr Thr Gly Lys Glu Asn Ala Lys Tyr Leu Ile Glu Lys Ile
545                 550                 555                 560

Lys Leu His Asp Met Gln Glu Gly Lys Cys Leu Tyr Ser Leu Glu Ala
                565                 570                 575

Ile Pro Leu Glu Asp Leu Leu Asn Asn Pro Phe Asn Tyr Glu Val Asp
            580                 585                 590

His Ile Ile Pro Arg Ser Val Ser Phe Asp Asn Ser Phe Asn Asn Lys
        595                 600                 605

Val Leu Val Lys Gln Glu Glu Ala Ser Lys Lys Gly Asn Arg Thr Pro
    610                 615                 620

Phe Gln Tyr Leu Ser Ser Ser Asp Ser Lys Ile Ser Tyr Glu Thr Phe
625                 630                 635                 640

Lys Lys His Ile Leu Asn Leu Ala Lys Gly Lys Gly Arg Ile Ser Lys
                645                 650                 655

Thr Lys Lys Glu Tyr Leu Leu Glu Glu Arg Asp Ile Asn Arg Phe Ser
            660                 665                 670

Val Gln Lys Asp Phe Ile Asn Arg Asn Leu Val Asp Thr Arg Tyr Ala
        675                 680                 685

Thr Arg Gly Leu Met Asn Leu Leu Arg Ser Tyr Phe Arg Val Asn Asn
    690                 695                 700

Leu Asp Val Lys Val Lys Ser Ile Asn Gly Gly Phe Thr Ser Phe Leu
705                 710                 715                 720

Arg Arg Lys Trp Lys Phe Lys Lys Glu Arg Asn Lys Gly Tyr Lys His
                725                 730                 735

His Ala Glu Asp Ala Leu Ile Ile Ala Asn Ala Asp Phe Ile Phe Lys
            740                 745                 750

Glu Trp Lys Lys Leu Asp Lys Ala Lys Lys Val Met Glu Asn Gln Met
        755                 760                 765

Phe Glu Glu Lys Gln Ala Glu Ser Met Pro Glu Ile Glu Thr Glu Gln
    770                 775                 780

Glu Tyr Lys Glu Ile Phe Ile Thr Pro His Gln Ile Lys His Ile Lys
785                 790                 795                 800

Asp Phe Lys Asp Tyr Lys Tyr Ser His Arg Val Asp Lys Lys Pro Asn
                805                 810                 815
```

```
Arg Lys Leu Ile Asn Asp Thr Leu Tyr Ser Thr Arg Lys Asp Asp Lys
            820                 825                 830

Gly Asn Thr Leu Ile Val Asn Asn Leu Asn Gly Leu Tyr Asp Lys Asp
        835                 840                 845

Asn Asp Lys Leu Lys Lys Leu Ile Asn Lys Ser Pro Glu Lys Leu Leu
    850                 855                 860

Met Tyr His His Asp Pro Gln Thr Tyr Gln Lys Leu Lys Leu Ile Met
865                 870                 875                 880

Glu Gln Tyr Gly Asp Glu Lys Asn Pro Leu Tyr Lys Tyr Tyr Glu Glu
                885                 890                 895

Thr Gly Asn Tyr Leu Thr Lys Tyr Ser Lys Lys Asp Asn Gly Pro Val
            900                 905                 910

Ile Lys Lys Ile Lys Tyr Tyr Gly Asn Lys Leu Asn Ala His Leu Asp
        915                 920                 925

Ile Thr Asp Asp Tyr Pro Asn Ser Arg Asn Lys Val Val Lys Leu Ser
    930                 935                 940

Leu Lys Pro Tyr Arg Phe Asp Val Tyr Leu Asp Asn Gly Val Tyr Lys
945                 950                 955                 960

Phe Val Thr Val Lys Asn Leu Asp Val Ile Lys Lys Glu Asn Tyr Tyr
                965                 970                 975

Glu Val Asn Ser Lys Cys Tyr Glu Glu Ala Lys Lys Leu Lys Lys Ile
            980                 985                 990

Ser Asn Gln Ala Glu Phe Ile Ala  Ser Phe Tyr Lys Asn  Asp Leu Ile
        995                 1000                1005

Lys Ile  Asn Gly Glu Leu Tyr  Arg Val Ile Gly Val  Asn Asn Asp
    1010                1015                1020

Leu Leu  Asn Arg Ile Glu Val  Asn Met Ile Asp Ile  Thr Tyr Arg
    1025                1030                1035

Glu Tyr  Leu Glu Asn Met Asn  Asp Lys Arg Pro Pro  His Ile Ile
    1040                1045                1050

Lys Thr  Ile Ala Ser Lys Thr  Gln Ser Ile Lys Lys  Tyr Ser Thr
    1055                1060                1065

Asp Ile  Leu Gly Asn Leu Tyr  Glu Val Lys Ser Lys  Lys His Pro
    1070                1075                1080

Gln Ile  Ile Lys Lys Gly Ser  Gly Gly Ser Ser Gly  Gly Ser Ser
    1085                1090                1095

Gly Ser  Glu Thr Pro Gly Thr  Ser Glu Ser Ala Thr  Pro Glu Ser
    1100                1105                1110

Ser Gly  Gly Ser Ser Gly Gly  Ser Ser Thr Leu Asn  Ile Glu Asp
    1115                1120                1125

Glu Tyr  Arg Leu His Glu Thr  Ser Lys Glu Pro Asp  Val Ser Leu
    1130                1135                1140

Gly Ser  Thr Trp Leu Ser Asp  Phe Pro Gln Ala Trp  Ala Glu Thr
    1145                1150                1155

Gly Gly  Met Gly Leu Ala Val  Arg Gln Ala Pro Leu  Ile Ile Pro
    1160                1165                1170

Leu Lys  Ala Thr Ser Thr Pro  Val Ser Ile Lys Gln  Tyr Pro Met
    1175                1180                1185

Ser Gln  Glu Ala Arg Leu Gly  Ile Lys Pro His Ile  Gln Arg Leu
    1190                1195                1200

Leu Asp  Gln Gly Ile Leu Val  Pro Cys Gln Ser Pro  Trp Asn Thr
    1205                1210                1215

Pro Leu  Leu Pro Val Lys Lys  Pro Gly Thr Asn Asp  Tyr Arg Pro
```

```
    1220                1225                1230

Val Gln  Asp Leu Arg Glu Val  Asn Lys Arg Val Glu  Asp Ile His
    1235                1240                1245

Pro Thr  Val Pro Asn Pro Tyr  Asn Leu Leu Ser Gly  Leu Pro Pro
    1250                1255                1260

Ser His  Gln Trp Tyr Thr Val  Leu Asp Leu Lys Asp  Ala Phe Phe
    1265                1270                1275

Cys Leu  Arg Leu His Pro Thr  Ser Gln Pro Leu Phe  Ala Phe Glu
    1280                1285                1290

Trp Arg  Asp Pro Glu Met Gly  Ile Ser Gly Gln Leu  Thr Trp Thr
    1295                1300                1305

Arg Leu  Pro Gln Gly Phe Lys  Asn Ser Pro Thr Leu  Phe Asn Glu
    1310                1315                1320

Ala Leu  His Arg Asp Leu Ala  Asp Phe Arg Ile Gln  His Pro Asp
    1325                1330                1335

Leu Ile  Leu Leu Gln Tyr Val  Asp Asp Leu Leu Leu  Ala Ala Thr
    1340                1345                1350

Ser Glu  Leu Asp Cys Gln Gln  Gly Thr Arg Ala Leu  Leu Gln Thr
    1355                1360                1365

Leu Gly  Asn Leu Gly Tyr Arg  Ala Ser Ala Lys Lys  Ala Gln Ile
    1370                1375                1380

Cys Gln  Lys Gln Val Lys Tyr  Leu Gly Tyr Leu Leu  Lys Glu Gly
    1385                1390                1395

Gln Arg  Trp Leu Thr Glu Ala  Arg Lys Glu Thr Val  Met Gly Gln
    1400                1405                1410

Pro Thr  Pro Lys Thr Pro Arg  Gln Leu Arg Glu Phe  Leu Gly Lys
    1415                1420                1425

Ala Gly  Phe Cys Arg Leu Phe  Ile Pro Gly Phe Ala  Glu Met Ala
    1430                1435                1440

Ala Pro  Leu Tyr Pro Leu Thr  Lys Pro Gly Thr Leu  Phe Asn Trp
    1445                1450                1455

Gly Pro  Asp Gln Gln Lys Ala  Tyr Gln Glu Ile Lys  Gln Ala Leu
    1460                1465                1470

Leu Thr  Ala Pro Ala Leu Gly  Leu Pro Asp Leu Thr  Lys Pro Phe
    1475                1480                1485

Glu Leu  Phe Val Asp Glu Lys  Gln Gly Tyr Ala Lys  Gly Val Leu
    1490                1495                1500

Thr Gln  Lys Leu Gly Pro Trp  Arg Arg Pro Val Ala  Tyr Leu Ser
    1505                1510                1515

Lys Lys  Leu Asp Pro Val Ala  Ala Gly Trp Pro Pro  Cys Leu Arg
    1520                1525                1530

Met Val  Ala Ala Ile Ala Val  Leu Thr Lys Asp Ala  Gly Lys Leu
    1535                1540                1545

Thr Met  Gly Gln Pro Leu Val  Ile Leu Ala Pro His  Ala Val Glu
    1550                1555                1560

Ala Leu  Val Lys Gln Pro Pro  Asp Arg Trp Leu Ser  Asn Ala Arg
    1565                1570                1575

Met Thr  His Tyr Gln Ala Leu  Leu Leu Asp Thr Asp  Arg Val Gln
    1580                1585                1590

Phe Gly  Pro Val Val Ala Leu  Asn Pro Ala Thr Leu  Leu Pro Leu
    1595                1600                1605

Pro Glu  Glu Gly Leu Gln His  Asn Cys Leu Asp Ile  Leu Ala Glu
    1610                1615                1620
```

Ala His Gly Thr Arg Pro Asp Leu Thr Asp Gln Pro Leu Pro Asp
1625 1630 1635

Ala Asp His Thr Trp Tyr Thr Asp Gly Ser Ser Leu Leu Gln Glu
1640 1645 1650

Gly Gln Arg Lys Ala Gly Ala Ala Val Thr Thr Glu Thr Glu Val
1655 1660 1665

Ile Trp Ala Lys Ala Leu Pro Ala Gly Thr Ser Ala Gln Arg Ala
1670 1675 1680

Glu Leu Ile Ala Leu Thr Gln Ala Leu Lys Met Ala Glu Gly Lys
1685 1690 1695

Lys Leu Asn Val Tyr Thr Asp Ser Arg Tyr Ala Phe Ala Thr Ala
1700 1705 1710

His Ile His Gly Glu Ile Tyr Arg Arg Arg Gly Trp Leu Thr Ser
1715 1720 1725

Glu Gly Lys Glu Ile Lys Asn Lys Asp Glu Ile Leu Ala Leu Leu
1730 1735 1740

Lys Ala Leu Phe Leu Pro Lys Arg Leu Ser Ile Ile His Cys Pro
1745 1750 1755

Gly His Gln Lys Gly His Ser Ala Glu Ala Arg Gly Asn Arg Met
1760 1765 1770

Ala Asp Gln Ala Ala Arg Lys Ala Ala Ile Thr Glu Thr Pro Asp
1775 1780 1785

Thr Ser Thr Leu Leu Ile Glu Asn Ser Ser Pro Ser Gly Gly Ser
1790 1795 1800

Lys Arg Thr Ala Asp Gly Ser Glu Lys Arg Thr Ala Asp Ser Gln
1805 1810 1815

His Ser Thr Pro Pro Lys Thr Lys Arg Lys Val Glu Phe Glu Pro
1820 1825 1830

Lys Lys Lys Arg Lys Val
1835

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Pro Lys Lys Lys Arg Lys Val
1 5

<210> SEQ ID NO 5
<211> LENGTH: 18
<212> TYPE: PRT
<213> ORGANISM: Artificial Sequence
<220> FEATURE:
<223> OTHER INFORMATION: Synthetic

<400> SEQUENCE: 5

Lys Arg Thr Ala Asp Gly Ser Glu Phe Glu Ser Pro Lys Lys Lys Arg
1 5 10 15

Lys Val

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Lys Arg Thr Ala Asp Ser Ser His Ser Thr Pro Pro Lys Thr Lys Arg
1 5 10 15

Lys Val

<210> SEQ ID NO 7
<211> LENGTH: 18
<212> TYPE: PRT
<213> ORGANISM: Artificial Sequence
<220> FEATURE:
<223> OTHER INFORMATION: Synthetic

<400> SEQUENCE: 7

Lys Arg Pro Ala Ala Thr Lys Lys Ala Gly Gln Ala Lys Lys Lys Lys
1 5 10 15

Leu Asp

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Pro Ala Ala Lys Arg Val Lys Leu Asp
1 5

<210> SEQ ID NO 9
<211> LENGTH: 76
<212> TYPE: DNA
<213> ORGANISM: Artificial Sequence
<220> FEATURE:
<223> OTHER INFORMATION: Synthetic

<400> SEQUENCE: 9
gttttagagc tagaaatagc aagttaaaat aaggctagtc cgttatcaac ttgaaaaagt 60
gggaccgagt cggtcc 76

<210> SEQ ID NO 10
<211> LENGTH: 76
<212> TYPE: DNA
<213> ORGANISM: Artificial Sequence
<220> FEATURE:
<223> OTHER INFORMATION: Synthetic

<400> SEQUENCE: 10
gttttagtac tctggaaaca gaatctacta aaacaaggca aaatgccgtg tttatctcgt 60
caacttgttg gcgaga 76

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
caccttcagc ttggcggtct 20

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
tacgagggca ctcaaaccgc caagctgaag 30

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ggtcaccttc agcttggcgg t 21

<210> SEQ ID NO 14
<211> LENGTH: 34
<212> TYPE: DNA
<213> ORGANISM: Artificial Sequence
<220> FEATURE:
<223> OTHER INFORMATION: Synthetic

<400> SEQUENCE: 14
tacgagggca cccagactgc caagctgaag gtga 34

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
aagttcagcg tgtccggctt 20

<210> SEQ ID NO 16
<211> LENGTH: 36
<212> TYPE: DNA
<213> ORGANISM: Artificial Sequence
<220> FEATURE:
<223> OTHER INFORMATION: Synthetic

<400> SEQUENCE: 16
gtcagcttgc cgtaggtggc atcgccctcg ccttcg 36

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
tgaacttcag ggtcagcttg cc 22

<210> SEQ ID NO 18
<211> LENGTH: 65
<212> TYPE: DNA
<213> ORGANISM: Artificial Sequence
<220> FEATURE:
<223> OTHER INFORMATION: Synthetic

<400> SEQUENCE: 18
acaagttcag cgtgtccggc gagggcgagg gcgatgccac gtacggcaag ctgaccctga 60
agttc 65

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
gcggagaggg cacccccga 19

<210> SEQ ID NO 20
<211> LENGTH: 36
<212> TYPE: DNA
<213> ORGANISM: Artificial Sequence
<220> FEATURE:
<223> OTHER INFORMATION: Synthetic

<400> SEQUENCE: 20
gttggtcatg cgaccctgct cgggggtgcc ctctcc 36

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ggtcatgcga ccctgctcgg a 21

<210> SEQ ID NO 22
<211> LENGTH: 31
<212> TYPE: DNA
<213> ORGANISM: Artificial Sequence
<220> FEATURE:
<223> OTHER INFORMATION: Synthetic

<400> SEQUENCE: 22
cggagagggc acccccgagc agggtcgcat g 31

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gagtccgagc agaagaagaa 20

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
atgggagcac ttcttcttct gctc 24

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
cagaagctgg aggaggaagg gc 22

<210> SEQ ID NO 26
<211> LENGTH: 31
<212> TYPE: DNA
<213> ORGANISM: Artificial Sequence
<220> FEATURE:
<223> OTHER INFORMATION: Synthetic

<400> SEQUENCE: 26
tgctcggaat cagacccttc ctcctccagc t 31

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gagtccgagc agaagaagaa 20

<210> SEQ ID NO 28
<211> LENGTH: 26
<212> TYPE: DNA
<213> ORGANISM: Artificial Sequence
<220> FEATURE:
<223> OTHER INFORMATION: Synthetic

<400> SEQUENCE: 28
atgtgatggg agttcttctt ctgctc 26

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
cagaagctgg aggaggaagg gc 22

<210> SEQ ID NO 30
<211> LENGTH: 31
<212> TYPE: DNA
<213> ORGANISM: Artificial Sequence
<220> FEATURE:
<223> OTHER INFORMATION: Synthetic

<400> SEQUENCE: 30
ttctgctcgg actcagcttc ctcctccagc t 31

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gagtccgagc agaagaagaa 20

<210> SEQ ID NO 32
<211> LENGTH: 35
<212> TYPE: DNA
<213> ORGANISM: Artificial Sequence
<220> FEATURE:
<223> OTHER INFORMATION: Synthetic

<400> SEQUENCE: 32
gagcagaaga agaaaagctt gggctcccat cacat 35

<210> SEQ ID NO 33
<211> LENGTH: 22
<212> TYPE: DNA
<213> ORGANISM: Artificial Sequence
<220> FEATURE:
<223> OTHER INFORMATION: Synthetic

<400> SEQUENCE: 33
cagaagctgg aggaggaagg gc 22

<210> SEQ ID NO 34
<211> LENGTH: 37
<212> TYPE: DNA
<213> ORGANISM: Artificial Sequence
<220> FEATURE:
<223> OTHER INFORMATION: Synthetic

<400> SEQUENCE: 34
tgctcggact caggccaagc ttcttcctcc tccagct 37

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
agatgactat ctttaatgtc 20

<210> SEQ ID NO 36
<211> LENGTH: 45
<212> TYPE: DNA
<213> ORGANISM: Artificial Sequence
<220> FEATURE:
<223> OTHER INFORMATION: Synthetic

<400> SEQUENCE: 36
attacacctg cagctctcat tttccttata ttaaagatag tcatc 45

<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
aagatgacta tctttaatgt ct 22

<210> SEQ ID NO 38
<211> LENGTH: 34

<212> TYPE: DNA
<213> ORGANISM: Artificial Sequence
<220> FEATURE:
<223> OTHER INFORMATION: Synthetic

<400> SEQUENCE: 38
agctctcatt ttccatacat taaagatagt catc 34

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
tcccctccag gccgtgcata 20

<210> SEQ ID NO 40
<211> LENGTH: 40
<212> TYPE: DNA
<213> ORGANISM: Artificial Sequence
<220> FEATURE:
<223> OTHER INFORMATION: Synthetic

<400> SEQUENCE: 40
tcttgtcgat ggtcagcaca gctttatgca cggcctggag 40

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
cagcttcagt ccctttctcg t 21

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
atcgacaaga aagggactga agct 24

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
tcccctccag gccgtgcata 20

<210> SEQ ID NO 44
<211> LENGTH: 40
<212> TYPE: DNA
<213> ORGANISM: Artificial Sequence
<220> FEATURE:
<223> OTHER INFORMATION: Synthetic

<400> SEQUENCE: 44
tctcgtcgat ggtcagcaca gctttatgca cggcctggag 40

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
agggttgccc ttgccactca 20

<210> SEQ ID NO 46
<211> LENGTH: 26
<212> TYPE: DNA
<213> ORGANISM: Artificial Sequence
<220> FEATURE:
<223> OTHER INFORMATION: Synthetic

<400> SEQUENCE: 46
gctcctttcc tgagtggcaa gggcaa 26

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
agggttgccc ttgccactca 20

<210> SEQ ID NO 48
<211> LENGTH: 26
<212> TYPE: DNA
<213> ORGANISM: Artificial Sequence
<220> FEATURE:
<223> OTHER INFORMATION: Synthetic

<400> SEQUENCE: 48
acagctcctt tgagtggcaa gggcaa 26

<210> SEQ ID NO 49
<211> LENGTH: 21
<212> TYPE: DNA
<213> ORGANISM: Artificial Sequence
<220> FEATURE:
<223> OTHER INFORMATION: Synthetic

<400> SEQUENCE: 49
gcgcttcaag gtgcacatgg a 21

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
gctgtcccct cagttcatgt a 21

<210> SEQ ID NO 51
<211> LENGTH: 23
<212> TYPE: DNA
<213> ORGANISM: Artificial Sequence
<220> FEATURE:
<223> OTHER INFORMATION: Synthetic

<400> SEQUENCE: 51
gatggagggc tccgtgaacg gcc 23

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
gttcgcctgg gacatcctgt ccc 23

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gtaggtcagg gtggtcacga 20

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
gctcctcgcc cttgctcacc a 21

<210> SEQ ID NO 55
<211> LENGTH: 22
<212> TYPE: DNA
<213> ORGANISM: Artificial Sequence
<220> FEATURE:
<223> OTHER INFORMATION: Synthetic

<400> SEQUENCE: 55
gcaagggcga ggagctgttc ac 22

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
gtgaccaccc tgacctacgg cg 22

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
gagaagccgt agcccatcac g 21

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
gatcttcatg gcgggcatgg 20

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
gatcaccggc accctgaacg gcg 23

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
gcagccccta cctgctgagc ca 22

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
gttgcccacc ctagtcattg g 21

<210> SEQ ID NO 62
<211> LENGTH: 21
<212> TYPE: DNA
<213> ORGANISM: Artificial Sequence
<220> FEATURE:
<223> OTHER INFORMATION: Synthetic

<400> SEQUENCE: 62
ggccgtttgt actttgtcct c 21

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
gcctgggcca gggagggagg ggc 23

<210> SEQ ID NO 64
<211> LENGTH: 22
<212> TYPE: DNA
<213> ORGANISM: Artificial Sequence
<220> FEATURE:
<223> OTHER INFORMATION: Synthetic

<400> SEQUENCE: 64
gtggttgccc accctagtca tt 22

<210> SEQ ID NO 65
<211> LENGTH: 21
<212> TYPE: DNA
<213> ORGANISM: Artificial Sequence
<220> FEATURE:
<223> OTHER INFORMATION: Synthetic

<400> SEQUENCE: 65
gttgcccacc ctagtcattg g 21

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
ggccgtttgt actttgtcct c 21

<210> SEQ ID NO 67
<211> LENGTH: 23
<212> TYPE: DNA
<213> ORGANISM: Artificial Sequence
<220> FEATURE:
<223> OTHER INFORMATION: Synthetic

<400> SEQUENCE: 67
gcctgggcca gggagggagg ggc 23

<210> SEQ ID NO 68
<211> LENGTH: 22
<212> TYPE: DNA
<213> ORGANISM: Artificial Sequence
<220> FEATURE:
<223> OTHER INFORMATION: Synthetic

<400> SEQUENCE: 68
gtggttgccc accctagtca tt 22

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
gttgcccacc ctagtcattg g 21

<210> SEQ ID NO 70
<211> LENGTH: 21
<212> TYPE: DNA
<213> ORGANISM: Artificial Sequence
<220> FEATURE:
<223> OTHER INFORMATION: Synthetic

<400> SEQUENCE: 70
ggccgtttgt actttgtcct c 21

<210> SEQ ID NO 71

<211> LENGTH: 23
<212> TYPE: DNA
<213> ORGANISM: Artificial Sequence
<220> FEATURE:
<223> OTHER INFORMATION: Synthetic

<400> SEQUENCE: 71
gcctgggcca gggagggagg ggc 23

<210> SEQ ID NO 72
<211> LENGTH: 22
<212> TYPE: DNA
<213> ORGANISM: Artificial Sequence
<220> FEATURE:
<223> OTHER INFORMATION: Synthetic

<400> SEQUENCE: 72
gtggttgccc accctagtca tt 22

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
gctgtgtttg cgtctctccc 20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
gacaagtgtg atcacttggg 20

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
gcaggacggt cacctttggg g 21

<210> SEQ ID NO 76
<211> LENGTH: 23
<212> TYPE: DNA
<213> ORGANISM: Artificial Sequence
<220> FEATURE:
<223> OTHER INFORMATION: Synthetic

<400> SEQUENCE: 76
gcatctttac cagatctcaa aaa 23

<210> SEQ ID NO 77
<211> LENGTH: 23
<212> TYPE: DNA
<213> ORGANISM: Artificial Sequence
<220> FEATURE:
<223> OTHER INFORMATION: Synthetic

<400> SEQUENCE: 77
gtggctgtgt ttgcgtctct ccc 23

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78 ggggggata gacatgggta 20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
gacctcgggg gggatagaca 20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
gggtttgttg aacttgacct 20

<210> SEQ ID NO 81
<211> LENGTH: 21
<212> TYPE: DNA
<213> ORGANISM: Artificial Sequence
<220> FEATURE:
<223> OTHER INFORMATION: Synthetic

<400> SEQUENCE: 81
gttcaatcat taagaagaca a 21

<210> SEQ ID NO 82
<211> LENGTH: 23
<212> TYPE: DNA
<213> ORGANISM: Artificial Sequence
<220> FEATURE:
<223> OTHER INFORMATION: Synthetic

<400> SEQUENCE: 82
gcacgtgagc cttgctcgag gcc 23

<210> SEQ ID NO 83
<211> LENGTH: 23
<212> TYPE: DNA
<213> ORGANISM: Artificial Sequence
<220> FEATURE:
<223> OTHER INFORMATION: Synthetic

<400> SEQUENCE: 83
gcccatgtct atcccccccg agg 23

<210> SEQ ID NO 84
<211> LENGTH: 20
<212> TYPE: DNA

<213> ORGANISM: Artificial Sequence
<220> FEATURE:
<223> OTHER INFORMATION: Synthetic

<400> SEQUENCE: 84
gggtttgttg aacttgacct 20

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
ggaaaagctg ctgtcagcca c 21

<210> SEQ ID NO 86
<211> LENGTH: 45
<212> TYPE: DNA
<213> ORGANISM: Artificial Sequence
<220> FEATURE:
<223> OTHER INFORMATION: Synthetic

<400> SEQUENCE: 86
gggccgaccc tacgagggca cctagaccgc caagctgaag gtgac 45

<210> SEQ ID NO 87
<211> LENGTH: 130
<212> TYPE: DNA
<213> ORGANISM: Artificial Sequence
<220> FEATURE:
<223> OTHER INFORMATION: Synthetic

<400> SEQUENCE: 87
gcggagaggg cacccccgag guuuuagagc uagaaauagc aaguuaaaau aaggcuaguc 60
cguuaucaac uugaaaaagu ggcaccgagu cgguccguug gucaugcgac ccugcucggg 120
ggugcccucu 130

<210> SEQ ID NO 88
<211> LENGTH: 79
<212> TYPE: DNA
<213> ORGANISM: Artificial Sequence
<220> FEATURE:
<223> OTHER INFORMATION: Synthetic

<400> SEQUENCE: 88
ggtgggcggc ggagagggca cccccgaggg gccccaaatc acctgcctcg tgggagacaa 60
aatacccgtt ccgagcagg 79

<210> SEQ ID NO 89
<211> LENGTH: 127
<212> TYPE: DNA
<213> ORGANISM: Artificial Sequence
<220> FEATURE:
<223> OTHER INFORMATION: Synthetic

<400> SEQUENCE: 89
gcggagaggg cacccccgag guuuuagagc uagaaauagc uuaaaauaag gcuaguccgu 60
uaucaacuug aaaaaguggc accgagucgg uccguugguc augcgacccu gcucgggggu 120
gcccucu 127

<210> SEQ ID NO 90
<211> LENGTH: 67
<212> TYPE: DNA
<213> ORGANISM: Artificial Sequence
<220> FEATURE:
<223> OTHER INFORMATION: Synthetic

<400> SEQUENCE: 90
ccacaagttc agcgtgtccg gctttggcga gacaaatcac ctgcctcgtg gaatacggta 60
aacctac 67

<210> SEQ ID NO 91
<211> LENGTH: 145
<212> TYPE: DNA
<213> ORGANISM: Artificial Sequence
<220> FEATURE:
<223> OTHER INFORMATION: Synthetic

<400> SEQUENCE: 91
aaguucagcg uguccggcuu guuuuagagc uagaaauagc aaguuaaaau aaggcuaguc 60
cguuaucaac uugaaaaagu ggcaccgagu cgguccguca gcuugccgua gguggcaucg 120
cccucgccuu cgccggacac gcuga 145

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
agaugacuau cuuuaauguc 20

<210> SEQ ID NO 93
<211> LENGTH: 69
<212> TYPE: DNA
<213> ORGANISM: Artificial Sequence
<220> FEATURE:
<223> OTHER INFORMATION: Synthetic

<400> SEQUENCE: 93
cattttccat acagtcagta tcaattctgg aagaatttcc agacattaaa gatagtcatc 60
ttggggctg 69

<210> SEQ ID NO 94
<211> LENGTH: 69
<212> TYPE: DNA
<213> ORGANISM: Artificial Sequence
<220> FEATURE:
<223> OTHER INFORMATION: Synthetic

<400> SEQUENCE: 94
cagccccaag atgactatct ttaatctctg gaaattcttc cagaattgat actgactgta 60
tcgaaaagt 69

<210> SEQ ID NO 95
<211> LENGTH: 45
<212> TYPE: DNA
<213> ORGANISM: Artificial Sequence
<220> FEATURE:
<223> OTHER INFORMATION: Synthetic

<400> SEQUENCE: 95
attacaccug cagcucucau uuuccuuaua uuaaagauag ucauc 45

<210> SEQ ID NO 96
<211> LENGTH: 69
<212> TYPE: DNA
<213> ORGANISM: Artificial Sequence
<220> FEATURE:
<223> OTHER INFORMATION: Synthetic

<400> SEQUENCE: 96
cattttccat acagtcagta tcaattctgg aagaatttcc agacattaaa gatagtcatc 60
ttggggctg 69

<210> SEQ ID NO 97
<211> LENGTH: 28
<212> TYPE: DNA
<213> ORGANISM: Artificial Sequence
<220> FEATURE:
<223> OTHER INFORMATION: Synthetic

<400> SEQUENCE: 97
cuacugauag aaauuauauu ccuuuuac 28

<210> SEQ ID NO 98
<211> LENGTH: 106
<212> TYPE: DNA
<213> ORGANISM: Artificial Sequence
<220> FEATURE:
<223> OTHER INFORMATION: Synthetic

<400> SEQUENCE: 98
caaaaagaag gtcttcatta cacctgcagc tctcattttc catacagtca gtatcaattc 60
tggaagaatt tccagacatt aaagatagtc atcttggggc tggtcc 106

<210> SEQ ID NO 99
<211> LENGTH: 74
<212> TYPE: DNA
<213> ORGANISM: Artificial Sequence
<220> FEATURE:
<223> OTHER INFORMATION: Synthetic

<400> SEQUENCE: 99
caaaaagaag gtcttcatta cacctgcagc tctcattttc cttatattaa agatagtcat 60
cttggggctg gtcc 74

<210> SEQ ID NO 100
<211> LENGTH: 74
<212> TYPE: DNA
<213> ORGANISM: Artificial Sequence
<220> FEATURE:
<223> OTHER INFORMATION: Synthetic

<400> SEQUENCE: 100
caaaaagaag gtcttcatta cacctgcagc tctcattttc cagacattaa agatagtcat 60
cttggggctg gtcc 74

<210> SEQ ID NO 101
<211> LENGTH: 74
<212> TYPE: DNA
<213> ORGANISM: Artificial Sequence
<220> FEATURE:
<223> OTHER INFORMATION: Synthetic

<400> SEQUENCE: 101
caaaaagaag gtcttcatta cacctgcagc tctcattttc cttatagtaa agatagtcat 60
cttggggctg gtcc 74

<210> SEQ ID NO 102
<211> LENGTH: 73
<212> TYPE: DNA
<213> ORGANISM: Artificial Sequence
<220> FEATURE:
<223> OTHER INFORMATION: Synthetic

<400> SEQUENCE: 102
caaaaagaag gtcttcatta cacctgcagc tctcattttc cttatataaa gatagtcatc 60
ttggggctgg tcc 73

<210> SEQ ID NO 103
<211> LENGTH: 88
<212> TYPE: DNA
<213> ORGANISM: Artificial Sequence
<220> FEATURE:
<223> OTHER INFORMATION: Synthetic

<400> SEQUENCE: 103
caaaaagaag gtcttcatta cacctgcagc tctcatcaat tctggaagaa tttccagaca 60
ttaaagatag tcatcttggg gctggtcc 88

<210> SEQ ID NO 104
<211> LENGTH: 103
<212> TYPE: DNA
<213> ORGANISM: Artificial Sequence
<220> FEATURE:
<223> OTHER INFORMATION: Synthetic

<400> SEQUENCE: 104
caaaaagaag gtcttcatta cacctgcagc tctcattttc catacagtca gtatcaattc 60
tggaagaatt tccagacaaa gatagtcatc ttggggctgg tcc 103

<210> SEQ ID NO 105
<211> LENGTH: 107
<212> TYPE: DNA
<213> ORGANISM: Artificial Sequence
<220> FEATURE:
<223> OTHER INFORMATION: Synthetic

<400> SEQUENCE: 105
caaaaagaag gtcttcatta cacctgcagc tctcattttc catacagtca gtatcaattc 60
tggaagaatt tccagaccat taaagatagt catcttgggg ctggtcc 107

<210> SEQ ID NO 106
<211> LENGTH: 71
<212> TYPE: DNA
<213> ORGANISM: Artificial Sequence
<220> FEATURE:
<223> OTHER INFORMATION: Synthetic

<400> SEQUENCE: 106
caaaaagaag gtcttcatta cacctgcagc tctcattttg acattaaaga tagtcatctt 60
ggggctggtc c 71

<210> SEQ ID NO 107
<211> LENGTH: 98
<212> TYPE: DNA

<213> ORGANISM: Artificial Sequence
<220> FEATURE:
<223> OTHER INFORMATION: Synthetic

<400> SEQUENCE: 107
caaaaagaag gtcttcatta cacctgcagc tctcatttgt cagtatcaat tctggaagaa 60
tttccagaca ttaaagatag tcatcttggg gctggtcc 98

<210> SEQ ID NO 108
<211> LENGTH: 74
<212> TYPE: DNA
<213> ORGANISM: Artificial Sequence
<220> FEATURE:
<223> OTHER INFORMATION: Synthetic

<400> SEQUENCE: 108
caaaaagaag gtcttcatta cacctgcagc tctcattttc catacattaa agatagtcat 60
cttggggctg gtcc 74

<210> SEQ ID NO 109
<211> LENGTH: 95
<212> TYPE: DNA
<213> ORGANISM: Artificial Sequence
<220> FEATURE:
<223> OTHER INFORMATION: Synthetic

<400> SEQUENCE: 109
caaaaagaag gtcttcatta cacctgcagc tctcattttc catacagtca gtatcaattc 60
tggaagaatt tccagactca tcttggggct ggtcc 95

<210> SEQ ID NO 110
<211> LENGTH: 89
<212> TYPE: DNA
<213> ORGANISM: Artificial Sequence
<220> FEATURE:
<223> OTHER INFORMATION: Synthetic

<400> SEQUENCE: 110
caaaaagaag gtcttcatta cacctgcagc tctcattttc catacagtca gtatcaattc 60
tggaagaata gtcatcttgg ggctggtcc 89

<210> SEQ ID NO 111
<211> LENGTH: 108
<212> TYPE: DNA
<213> ORGANISM: Artificial Sequence
<220> FEATURE:
<223> OTHER INFORMATION: Synthetic

<400> SEQUENCE: 111
ctctcccctc caggccgtgc ataaggctgt gctgaccatc gacaagaaag ggactgaagc 60
tgctggggcc atgtttttag aggccatacc catgtctatc ccccccga 108

<210> SEQ ID NO 112
<211> LENGTH: 108
<212> TYPE: DNA
<213> ORGANISM: Artificial Sequence
<220> FEATURE:
<223> OTHER INFORMATION: Synthetic

<400> SEQUENCE: 112
ctctcccctc caggccgtgc ataaagctgt gctgaccatc gacgagaaag ggactgaagc 60
tgctggggcc atgtttttag aggccatacc catgtctatc ccccccga 108

<210> SEQ ID NO 113
<211> LENGTH: 96
<212> TYPE: DNA
<213> ORGANISM: Artificial Sequence
<220> FEATURE:
<223> OTHER INFORMATION: Synthetic

<400> SEQUENCE: 113
ctctcccctc caggccgtgc tgaccatcga caagaaaggg actgaagctg ctggggccat 60
gtttttagag gccataccca tgtctatccc ccccga 96

<210> SEQ ID NO 114
<211> LENGTH: 96
<212> TYPE: DNA
<213> ORGANISM: Artificial Sequence
<220> FEATURE:
<223> OTHER INFORMATION: Synthetic

<400> SEQUENCE: 114
ctctcccctc caggctgtgc tgaccatcga caagaaaggg actgaagctg ctggggccat 60
gtttttagag gccataccca tgtctatccc ccccga 96

<210> SEQ ID NO 115
<211> LENGTH: 88
<212> TYPE: DNA
<213> ORGANISM: Artificial Sequence
<220> FEATURE:
<223> OTHER INFORMATION: Synthetic

<400> SEQUENCE: 115
ctctcccctc caggccgtgc ataaggctgt gctgaccatc gacgagagcc atgtttttag 60
aggccatacc catgtctatc ccccccga 88

<210> SEQ ID NO 116
<211> LENGTH: 71
<212> TYPE: DNA
<213> ORGANISM: Artificial Sequence
<220> FEATURE:
<223> OTHER INFORMATION: Synthetic

<400> SEQUENCE: 116
ctctcccctc cagggactga agctgctggg gccatgtttt tagaggccat acccatgtct 60
atcccccccg a 71

<210> SEQ ID NO 117
<211> LENGTH: 98
<212> TYPE: DNA
<213> ORGANISM: Artificial Sequence
<220> FEATURE:
<223> OTHER INFORMATION: Synthetic

<400> SEQUENCE: 117
ctctcccctc caggccgtgt gctgaccatc gacaagaaag ggactgaagc tgctggggcc 60
atgtttttag aggccatacc catgtctatc ccccccga 98

<210> SEQ ID NO 118
<211> LENGTH: 28
<212> TYPE: DNA
<213> ORGANISM: Artificial Sequence
<220> FEATURE:
<223> OTHER INFORMATION: Synthetic

<400> SEQUENCE: 118
ctctcccctc caggccgtgc ccccccga 28

<210> SEQ ID NO 119
<211> LENGTH: 39
<212> TYPE: DNA
<213> ORGANISM: Artificial Sequence
<220> FEATURE:
<223> OTHER INFORMATION: Synthetic

<400> SEQUENCE: 119
ctctcccctc caggccatac ccatgtctat cccccccga 39

<210> SEQ ID NO 120
<211> LENGTH: 109
<212> TYPE: DNA
<213> ORGANISM: Artificial Sequence
<220> FEATURE:
<223> OTHER INFORMATION: Synthetic

<400> SEQUENCE: 120
ctctcccctc caggccgtgc cataaagctg tgctgaccat cgacaagaaa gggactgaag 60
ctgctggggc catgttttta gaggccatac ccatgtctat cccccccga 109

<210> SEQ ID NO 121
<211> LENGTH: 108
<212> TYPE: DNA
<213> ORGANISM: Artificial Sequence
<220> FEATURE:
<223> OTHER INFORMATION: Synthetic

<400> SEQUENCE: 121
ctctcccctc caggccgtgc ataaggctgt gctgagcatc gacaagaaag ggactgaagc 60
tgctggggcc atgtttttag aggccatacc catgtctatc ccccccga 108

<210> SEQ ID NO 122
<211> LENGTH: 108
<212> TYPE: DNA
<213> ORGANISM: Artificial Sequence
<220> FEATURE:
<223> OTHER INFORMATION: Synthetic

<400> SEQUENCE: 122
ctctcccctc caggccgtgc ataaggctgt gctgagcatc gacgagaaag ggactgaagc 60
tgctggggcc atgtttttag aggccatacc catgtctatc ccccccga 108

<210> SEQ ID NO 123
<211> LENGTH: 108
<212> TYPE: DNA
<213> ORGANISM: Artificial Sequence
<220> FEATURE:
<223> OTHER INFORMATION: Synthetic

<400> SEQUENCE: 123
ctctcccctc caggccgtgc ataaagctgt gctgagcatc gacaagaaag ggactgaagc 60
tgctggggcc atgtttttag aggccatacc catgtctatc ccccccga 108

<210> SEQ ID NO 124
<211> LENGTH: 48
<212> TYPE: DNA
<213> ORGANISM: Artificial Sequence
<220> FEATURE:
<223> OTHER INFORMATION: Synthetic

<400> SEQUENCE: 124
tggtgccacc accacagctc cttccctgag tggcaagggc aaccctga 48

<210> SEQ ID NO 125
<211> LENGTH: 122
<212> TYPE: DNA
<213> ORGANISM: Artificial Sequence
<220> FEATURE:
<223> OTHER INFORMATION: Synthetic

<400> SEQUENCE: 125
aggguugccc uugccacuca guuuuagagc uagaaauagc aaguuaaaau aaggcuaguc 60
cguuaucaac uugaaaaagu ggcaccgagu cggugcgcuc cuuuccugag uggcaagggc 120
aa 122

<210> SEQ ID NO 126
<211> LENGTH: 36
<212> TYPE: DNA
<213> ORGANISM: Artificial Sequence
<220> FEATURE:
<223> OTHER INFORMATION: Synthetic

<400> SEQUENCE: 126
tgccaccacc acagctcctt ccctgagtgg caaggg 36

<210> SEQ ID NO 127
<211> LENGTH: 26
<212> TYPE: DNA
<213> ORGANISM: Artificial Sequence
<220> FEATURE:
<223> OTHER INFORMATION: Synthetic

<400> SEQUENCE: 127
gctccttccc tgagtggcaa gggcaa 26

<210> SEQ ID NO 128
<211> LENGTH: 23
<212> TYPE: DNA
<213> ORGANISM: Artificial Sequence
<220> FEATURE:
<223> OTHER INFORMATION: Synthetic

<400> SEQUENCE: 128
aacgggaacg gugagucucc ucg 23

<210> SEQ ID NO 129
<211> LENGTH: 96
<212> TYPE: DNA
<213> ORGANISM: Artificial Sequence
<220> FEATURE:
<223> OTHER INFORMATION: Synthetic

<400> SEQUENCE: 129
ggccgtgcat aaggctgtgc tgaccatcga caagaaaggg actgaagctg ctggggccat 60
gtttttagag gccataccca tgtctatccc ccccga 96

<210> SEQ ID NO 130
<211> LENGTH: 96
<212> TYPE: DNA
<213> ORGANISM: Artificial Sequence
<220> FEATURE:
<223> OTHER INFORMATION: Synthetic

<400> SEQUENCE: 130
ggccgtgcat aaagctgtgc tgaccatcga cgagaaaggg actgaagctg ctggggccat 60
gtttttagag gccataccca tgtctatccc ccccga 96

<210> SEQ ID NO 131
<211> LENGTH: 96
<212> TYPE: DNA
<213> ORGANISM: Artificial Sequence
<220> FEATURE:
<223> OTHER INFORMATION: Synthetic

<400> SEQUENCE: 131
ggccgtgcat aaagctgtgc tgaccatcga caagaaaggg actgaagctg ctggggccat 60
gtttttagag gccataccca tgtctatccc ccccga 96

<210> SEQ ID NO 132
<211> LENGTH: 96
<212> TYPE: DNA
<213> ORGANISM: Artificial Sequence
<220> FEATURE:
<223> OTHER INFORMATION: Synthetic

<400> SEQUENCE: 132
ggccgtgcat aaagctgtgc tgaccatcga ctagaaaggg actgaagctg ctggggccat 60
gtttttagag gccataccca tgtctatccc ccccga 96

<210> SEQ ID NO 133
<211> LENGTH: 96
<212> TYPE: DNA
<213> ORGANISM: Artificial Sequence
<220> FEATURE:
<223> OTHER INFORMATION: Synthetic

<400> SEQUENCE: 133
ggccgtgcat aaagctgtgc tgaccattga tgagaaaggg actgaagctg ctggggccat 60
gtttttagag gccataccca tgtctatccc ccccga 96

<210> SEQ ID NO 134
<211> LENGTH: 96
<212> TYPE: DNA
<213> ORGANISM: Artificial Sequence
<220> FEATURE:
<223> OTHER INFORMATION: Synthetic

<400> SEQUENCE: 134
ggccgtgcat aaagctgtgc tgaccatcga caagaaagtg actgaagctg ctggggccat 60
gtttttagag gccataccca tgtctatccc ccccga 96

<210> SEQ ID NO 135
<211> LENGTH: 84
<212> TYPE: DNA
<213> ORGANISM: Artificial Sequence
<220> FEATURE:
<223> OTHER INFORMATION: Synthetic

<400> SEQUENCE: 135
ggccgtgctg accatcgaca agaaagggac tgaagctgct ggggccatgt ttttagaggc 60
catacccatg tctatccccc ccga 84

<210> SEQ ID NO 136
<211> LENGTH: 16

<212> TYPE: DNA
<213> ORGANISM: Artificial Sequence
<220> FEATURE:
<223> OTHER INFORMATION: Synthetic

<400> SEQUENCE: 136
ggccgtgccc ccccga 16

<210> SEQ ID NO 137
<211> LENGTH: 18
<212> TYPE: DNA
<213> ORGANISM: Artificial Sequence
<220> FEATURE:
<223> OTHER INFORMATION: Synthetic

<400> SEQUENCE: 137
ggccgtggat tgaacaaa 18

<210> SEQ ID NO 138
<211> LENGTH: 95
<212> TYPE: DNA
<213> ORGANISM: Artificial Sequence
<220> FEATURE:
<223> OTHER INFORMATION: Synthetic

<400> SEQUENCE: 138
ggccgtgcta aggctgtgct gaccatcgac aagaaaggga ctgaagctgc tggggccatg 60
tttttagagg ccatacccat gtctatcccc cccga 95

<210> SEQ ID NO 139
<211> LENGTH: 98
<212> TYPE: DNA
<213> ORGANISM: Artificial Sequence
<220> FEATURE:
<223> OTHER INFORMATION: Synthetic

<400> SEQUENCE: 139
ggccgtgcat aaggctgtgc tgaccatcga caagaaaggg actgaagctg ctggggccat 60
gtttttagag gccataccca tgtctatccc ccccgagg 98

<210> SEQ ID NO 140
<211> LENGTH: 98
<212> TYPE: DNA
<213> ORGANISM: Artificial Sequence
<220> FEATURE:
<223> OTHER INFORMATION: Synthetic

<400> SEQUENCE: 140
ggccgtgcat aaagctgtgc tgaccatcga cgagaaaggg actgaagctg ctggggccat 60
gtttttagag gccataccca tgtctatccc ccccgagg 98

<210> SEQ ID NO 141
<211> LENGTH: 98
<212> TYPE: DNA
<213> ORGANISM: Artificial Sequence
<220> FEATURE:
<223> OTHER INFORMATION: Synthetic

<400> SEQUENCE: 141
ggccgtgcat aaagctgtgc tgaccatcga caagaaaggg actgaagctg ctggggccat 60
gtttttagag gccataccca tgtctatccc ccccgagg 98

<210> SEQ ID NO 142

<211> LENGTH: 98
<212> TYPE: DNA
<213> ORGANISM: Artificial Sequence
<220> FEATURE:
<223> OTHER INFORMATION: Synthetic

<400> SEQUENCE: 142
ggccgtgcat aaagctgtgc tgaccatcga ctagaaaggg actgaagctg ctggggccat 60
gtttttagag gccataccca tgtctatccc ccccgagg 98

<210> SEQ ID NO 143
<211> LENGTH: 98
<212> TYPE: DNA
<213> ORGANISM: Artificial Sequence
<220> FEATURE:
<223> OTHER INFORMATION: Synthetic

<400> SEQUENCE: 143
ggccgtgcat aaagctgtgc tgaccattga tgagaaaggg actgaagctg ctggggccat 60
gtttttagag gccataccca tgtctatccc ccccgagg 98

<210> SEQ ID NO 144
<211> LENGTH: 98
<212> TYPE: DNA
<213> ORGANISM: Artificial Sequence
<220> FEATURE:
<223> OTHER INFORMATION: Synthetic

<400> SEQUENCE: 144
ggccgtgcat aaagctgtgc tgaccatcga taagaaagtg actgaagctg ctggggccat 60
gtttttagag gccataccca tgtctatccc ccccgagg 98

<210> SEQ ID NO 145
<211> LENGTH: 97
<212> TYPE: DNA
<213> ORGANISM: Artificial Sequence
<220> FEATURE:
<223> OTHER INFORMATION: Synthetic

<400> SEQUENCE: 145
ggccgtgcta aggctgtgct gaccatcgac aagaaaggga ctgaagctgc tggggccatg 60
tttttagagg ccatacccat gtctatcccc cccgagg 97

<210> SEQ ID NO 146
<211> LENGTH: 86
<212> TYPE: DNA
<213> ORGANISM: Artificial Sequence
<220> FEATURE:
<223> OTHER INFORMATION: Synthetic

<400> SEQUENCE: 146
ggccgtgctg accatcgaca agaaagggac tgaagctgct ggggccatgt ttttagaggc 60
catacccatg tctatccccc ccgagg 86

<210> SEQ ID NO 147
<211> LENGTH: 47
<212> TYPE: DNA
<213> ORGANISM: Artificial Sequence
<220> FEATURE:
<223> OTHER INFORMATION: Synthetic

<400> SEQUENCE: 147
ggccgtgcat aaggctgtgc tgaccatcga caagaaaggg actgaag 47

<210> SEQ ID NO 148
<211> LENGTH: 29
<212> TYPE: DNA
<213> ORGANISM: Artificial Sequence
<220> FEATURE:
<223> OTHER INFORMATION: Synthetic

<400> SEQUENCE: 148
ggccataccc atgtctatcc cccccgagg 29

<210> SEQ ID NO 149
<211> LENGTH: 66
<212> TYPE: DNA
<213> ORGANISM: Artificial Sequence
<220> FEATURE:
<223> OTHER INFORMATION: Synthetic

<400> SEQUENCE: 149
ggccgtgcat aaagctgtgc tgaccatcga cgagaaaggg actgaagctg ctggggccat 60
gttttt 66

<210> SEQ ID NO 150
<211> LENGTH: 31
<212> TYPE: DNA
<213> ORGANISM: Artificial Sequence
<220> FEATURE:
<223> OTHER INFORMATION: Synthetic

<400> SEQUENCE: 150
gaggccatac ccatgtctat cccccccgag g 31

<210> SEQ ID NO 151
<211> LENGTH: 19
<212> TYPE: DNA
<213> ORGANISM: Artificial Sequence
<220> FEATURE:
<223> OTHER INFORMATION: Synthetic

<400> SEQUENCE: 151
ggccgtgccc cccccgagg 19

<210> SEQ ID NO 152
<211> LENGTH: 6
<212> TYPE: DNA
<213> ORGANISM: Artificial Sequence
<220> FEATURE:
<223> OTHER INFORMATION: Synthetic

<400> SEQUENCE: 152 gcgagg 6

<210> SEQ ID NO 153
<211> LENGTH: 16
<212> TYPE: DNA
<213> ORGANISM: Artificial Sequence
<220> FEATURE:
<223> OTHER INFORMATION: Synthetic

<400> SEQUENCE: 153
tctatccccc ccgagg 16

<210> SEQ ID NO 154
<211> LENGTH: 7
<212> TYPE: DNA

<213> ORGANISM: Artificial Sequence
<220> FEATURE:
<223> OTHER INFORMATION: Synthetic

<400> SEQUENCE: 154 ggccgtg 7

<210> SEQ ID NO 155
<211> LENGTH: 7
<212> TYPE: DNA
<213> ORGANISM: Artificial Sequence
<220> FEATURE:
<223> OTHER INFORMATION: Synthetic

<400> SEQUENCE: 155 ggccgtg 7

<210> SEQ ID NO 156
<211> LENGTH: 98
<212> TYPE: DNA
<213> ORGANISM: Artificial Sequence
<220> FEATURE:
<223> OTHER INFORMATION: Synthetic

<400> SEQUENCE: 156
ggccgtgcat aaagctgtgc tgaccatcga cgagagaggg actgaagctg ctggggccat 60
gtttttagag gccataccca tgtctatccc ccccgagg 98

<210> SEQ ID NO 157
<211> LENGTH: 98
<212> TYPE: DNA
<213> ORGANISM: Artificial Sequence
<220> FEATURE:
<223> OTHER INFORMATION: Synthetic

<400> SEQUENCE: 157
ggccgtgcat aaagctgtgc tgaccatcga cgagaggggg actgaagctg ctggggccat 60
gtttttagag gccataccca tgtctatccc ccccgagg 98

<210> SEQ ID NO 158
<211> LENGTH: 104
<212> TYPE: DNA
<213> ORGANISM: Artificial Sequence
<220> FEATURE:
<223> OTHER INFORMATION: Synthetic

<400> SEQUENCE: 158
gaaaagctgc tgtcagccac tggcagcagc agtcttactt ggattctgga atccattctg 60
gtgccaccac cacagctcct tccctgagtg gcaagggcaa ccct 104

<210> SEQ ID NO 159
<211> LENGTH: 101
<212> TYPE: DNA
<213> ORGANISM: Artificial Sequence
<220> FEATURE:
<223> OTHER INFORMATION: Synthetic

<400> SEQUENCE: 159
gaaaagctgc tgtcagccac tggcagcagc agtcttactt ggattctgga atccattctg 60
gtgccaccac cacagctcct ctgagtggca agggcaaccc t 101

<210> SEQ ID NO 160
<211> LENGTH: 67

-continued

<212> TYPE: DNA
<213> ORGANISM: Artificial Sequence
<220> FEATURE:
<223> OTHER INFORMATION: Synthetic

<400> SEQUENCE: 160
acttggattc tggaatccat tctggtgcca ccaccacagc tcctccctga gtggcaaggg 60
caaccct 67

<210> SEQ ID NO 161
<211> LENGTH: 33
<212> TYPE: DNA
<213> ORGANISM: Artificial Sequence
<220> FEATURE:
<223> OTHER INFORMATION: Synthetic

<400> SEQUENCE: 161
gaaaagctgc tgtcagccac tggcagcagc agt 33

<210> SEQ ID NO 162
<211> LENGTH: 69
<212> TYPE: DNA
<213> ORGANISM: Artificial Sequence
<220> FEATURE:
<223> OTHER INFORMATION: Synthetic

<400> SEQUENCE: 162
gaaaagctgc tgtcagccac tggcagcagc agtcttactt ggattctgga atccattctg 60
gtgccacca 69

<210> SEQ ID NO 163
<211> LENGTH: 78
<212> TYPE: DNA
<213> ORGANISM: Artificial Sequence
<220> FEATURE:
<223> OTHER INFORMATION: Synthetic

<400> SEQUENCE: 163
gaaaagctgc tgtcagccac tggcagcagc agtcttactt ggattctgga atccattctg 60
gtgccaccac cacagctc 78